(12) United States Patent
Sappenfield

(10) Patent No.: US 9,057,325 B2
(45) Date of Patent: Jun. 16, 2015

(54) ROTARY UNITS, ROTARY MECHANISMS, AND RELATED APPLICATIONS

(71) Applicant: Christopher C. Sappenfield, San Diego, CA (US)

(72) Inventor: Christopher C. Sappenfield, San Diego, CA (US)

( * ) Notice: Subject to any disclaimer, the term of this patent is extended or adjusted under 35 U.S.C. 154(b) by 0 days.

(21) Appl. No.: 14/341,804

(22) Filed: Jul. 26, 2014

(65) Prior Publication Data

US 2014/0331684 A1 Nov. 13, 2014

Related U.S. Application Data

(63) Continuation of application No. 13/832,575, filed on Mar. 15, 2013, now Pat. No. 8,834,315, which is a continuation-in-part of application No. 13/423,413, filed on Mar. 19, 2012, now Pat. No. 8,672,799, which (Continued)

(51) Int. Cl.
| | |
|---|---|
| *F02K 3/02* | (2006.01) |
| *F02C 3/04* | (2006.01) |
| *F16H 1/28* | (2006.01) |
| *F16H 37/08* | (2006.01) |
| *A61C 17/26* | (2006.01) |

(52) U.S. Cl.
CPC .. *F02C 3/04* (2013.01); *F16H 1/28* (2013.01); *F16H 37/0813* (2013.01); *A61C 17/26* (2013.01)

(58) Field of Classification Search
None
See application file for complete search history.

(56) References Cited

U.S. PATENT DOCUMENTS

| 75,676 | A | | 3/1868 | Goodwin | |
|---|---|---|---|---|---|
| 845,103 | A | | 2/1907 | Ljungstrom | |
| 1,059,450 | A | | 4/1913 | Foote | |
| 1,489,817 | A | * | 4/1924 | Campbell | 416/128 |
| 1,887,429 | A | * | 11/1932 | Price | 416/129 |
| 2,583,872 | A | * | 1/1952 | Newcomb | 475/332 |
| 2,851,905 | A | | 9/1958 | Clark | |
| 2,905,451 | A | * | 9/1959 | Thomas et al. | 366/244 |

(Continued)

FOREIGN PATENT DOCUMENTS

| CN | 2619094 | 6/2004 |
|---|---|---|
| JP | 05332413 | 12/1993 |

(Continued)

OTHER PUBLICATIONS

U.S. Appl. No. 61/104,748.

(Continued)

*Primary Examiner* — Dirk Wright
(74) *Attorney, Agent, or Firm* — Christopher C. Sappenfield

(57) ABSTRACT

The invention relates to rotary units and rotary mechanisms that are suitable for use in numerous applications. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. In some embodiments, engines include rotary mechanisms and are used in, for example, ground vehicles, marine vehicles, aircraft, or devices.

20 Claims, 33 Drawing Sheets

Related U.S. Application Data is a continuation-in-part of application No. 13/219,683, filed on Aug. 28, 2011, now Pat. No. 8,715,133, which is a continuation-in-part of application No. 13/184,332, filed on Jul. 15, 2011, now Pat. No. 8,668,618, which is a continuation-in-part of application No. 12/577,326, filed on Oct. 12, 2009, now Pat. No. 8,152,679, which is a continuation of application No. PCT/US2009/060386, filed on Oct. 12, 2009.

(60) Provisional application No. 61/104,748, filed on Oct. 12, 2008, provisional application No. 61/365,290, filed on Jul. 16, 2010, provisional application No. 61/376,725, filed on Aug. 25, 2010, provisional application No. 61/646,348, filed on May 13, 2012, provisional application No. 61/640,530, filed on Apr. 30, 2012.

(56) References Cited

U.S. PATENT DOCUMENTS

| | | | | |
|---|---|---|---|---|
| 2,950,634 | A | 8/1960 | Clark | |
| 3,088,414 | A * | 5/1963 | Ozgur | 415/68 |
| 3,222,533 | A * | 12/1965 | MacKay | 290/55 |
| 3,507,113 | A * | 4/1970 | Hagemeister et al. | 60/39.163 |
| 3,892,278 | A | 7/1975 | Smith et al. | |
| 3,913,415 | A | 10/1975 | Herr | |
| 4,044,841 | A | 8/1977 | Smith et al. | |
| 4,132,131 | A | 1/1979 | DeBruyne | |
| 4,159,624 | A | 7/1979 | Gruner | |
| 4,334,440 | A | 6/1982 | Fonck | |
| 4,365,525 | A | 12/1982 | Imazaike | |
| 4,464,095 | A | 8/1984 | Iida | |
| 4,535,653 | A | 8/1985 | Coburn | |
| 4,611,504 | A | 9/1986 | Rundle | |
| 4,627,310 | A | 12/1986 | Coburn | |
| 4,683,897 | A | 8/1987 | McBride | |
| 4,732,053 | A | 3/1988 | Gleasman | |
| 4,763,031 | A | 8/1988 | Wang | |
| 4,825,723 | A * | 5/1989 | Martin | 475/332 |
| 4,825,727 | A | 5/1989 | Komuro | |
| 4,896,567 | A | 1/1990 | Zhou et al. | |
| 4,926,715 | A | 5/1990 | Hirt et al. | |
| 4,964,844 | A * | 10/1990 | Bagnall | 475/295 |
| 5,014,428 | A | 5/1991 | Yamashita | |
| 5,426,806 | A | 6/1995 | Johnson et al. | |
| 5,595,147 | A | 1/1997 | Feuling | |
| 5,679,089 | A | 10/1997 | Levedahl | |
| 5,724,867 | A | 3/1998 | Jordan | |
| 5,870,790 | A | 2/1999 | Root | |
| 6,032,313 | A | 3/2000 | Tsang | |
| 6,176,804 | B1 | 1/2001 | Kekki et al. | |
| 6,179,503 | B1 | 1/2001 | Taghavi-Khanghah | |
| 6,213,224 | B1 | 4/2001 | Furuta | |
| 6,222,293 | B1 | 4/2001 | Ikeda et al. | |
| 6,357,118 | B1 | 3/2002 | Eichhorn et al. | |
| 6,379,276 | B1 | 4/2002 | Cheng | |
| 6,418,810 | B1 | 7/2002 | Kerr | |
| 6,492,743 | B1 | 12/2002 | Appa | |
| 6,626,792 | B2 | 9/2003 | Vranish | |
| 6,669,594 | B2 | 12/2003 | Kerr | |
| 6,672,538 | B2 | 1/2004 | Millea et al. | |
| 6,732,603 | B1 | 5/2004 | Hsu et al. | |
| 6,799,579 | B2 | 10/2004 | Joseph | |
| 6,829,457 | B2 | 12/2004 | Ryuzaki et al. | |
| 7,021,851 | B1 | 4/2006 | King | |
| 7,022,042 | B2 | 4/2006 | Fleytman | |
| 7,063,173 | B2 | 6/2006 | Herla | |
| 7,108,629 | B2 | 9/2006 | Hiraiwa | |
| 7,118,340 | B2 | 10/2006 | D'Anna | |
| 7,153,004 | B2 | 12/2006 | Galli | |
| 7,181,799 | B2 | 2/2007 | Gavney | |
| 7,182,708 | B2 | 2/2007 | Winzeler | |
| 7,296,495 | B2 * | 11/2007 | Quinn | 74/640 |
| 7,413,025 | B2 | 8/2008 | Provost | |
| 7,784,731 | B2 | 8/2010 | Lin | |
| 7,967,740 | B2 | 6/2011 | Mertens | |
| 7,993,067 | B2 | 8/2011 | Hall et al. | |
| 8,042,217 | B2 | 10/2011 | Sorrentino | |
| 8,046,861 | B2 | 11/2011 | Joseph | |
| 8,056,175 | B2 | 11/2011 | Kunita et al. | |
| 8,087,843 | B2 | 1/2012 | Ottaviani et al. | |
| 8,152,679 | B2 | 4/2012 | Sappenfield | |
| 8,250,694 | B2 | 8/2012 | Gatzemeyer | |
| 8,264,096 | B2 * | 9/2012 | Micu | 290/55 |
| 8,276,231 | B2 | 10/2012 | Gavney | |
| 8,277,358 | B2 | 10/2012 | Gasparrini | |
| 8,302,238 | B2 | 11/2012 | Biro | |
| 8,316,496 | B2 | 11/2012 | Al-Qaffas | |
| 8,358,029 | B2 | 1/2013 | Burkart | |
| 8,662,781 | B2 | 3/2014 | Sappenfield | |
| 8,668,618 | B2 | 3/2014 | Sappenfield | |
| 8,668,619 | B2 | 3/2014 | Sappenfield | |
| 8,672,798 | B2 | 3/2014 | Sappenfield | |
| 8,672,799 | B2 | 3/2014 | Sappenfield | |
| 8,684,883 | B2 | 4/2014 | Sappenfield | |
| 8,715,133 | B2 | 5/2014 | Sappenfield | |
| 8,742,608 | B2 * | 6/2014 | Micu | 290/44 |
| 8,814,505 | B2 * | 8/2014 | Bellis | 415/124.1 |
| 8,834,315 | B2 | 9/2014 | Sappenfield | |
| 2003/0113133 | A1 | 6/2003 | Ryuzaki | |
| 2003/0220169 | A1 | 11/2003 | Norman | |
| 2006/0103246 | A1 | 5/2006 | Umeda et al. | |
| 2007/0249460 | A1 | 10/2007 | Schulz et al. | |
| 2008/0070739 | A1 | 3/2008 | Nakamura et al. | |
| 2008/0134513 | A1 | 6/2008 | Oh | |
| 2008/0205970 | A1 | 8/2008 | LaFlamme et al. | |
| 2008/0233815 | A1 | 9/2008 | Nakamura et al. | |
| 2009/0136285 | A1 | 5/2009 | Hall et al. | |
| 2010/0041504 | A1 | 2/2010 | Palmer | |
| 2010/0089200 | A1 | 4/2010 | Sappenfield | |
| 2010/0175214 | A1 | 7/2010 | Payet | |
| 2010/0272500 | A1 | 10/2010 | Martin et al. | |
| 2011/0232013 | A1 | 9/2011 | Sappenfield | |
| 2011/0290052 | A1 | 12/2011 | Sappenfield | |
| 2011/0308351 | A1 | 12/2011 | Sappenfield | |
| 2012/0010039 | A1 | 1/2012 | Sappenfield | |
| 2012/0010040 | A1 | 1/2012 | Sappenfield | |
| 2012/0180586 | A1 | 7/2012 | Sappenfield | |
| 2012/0196719 | A1 | 8/2012 | Sappenfield | |
| 2012/0202641 | A1 | 8/2012 | Sappenfield | |
| 2013/0214627 | A1 | 8/2013 | Sappenfield | |
| 2014/0066246 | A1 | 3/2014 | Sappenfield | |

FOREIGN PATENT DOCUMENTS

| | | |
|---|---|---|
| WO | WO0011372 | 3/2000 |
| WO | WO2010042934 | 4/2010 |

OTHER PUBLICATIONS

U.S. Appl. No. 61/365,290.
U.S. Appl. No. 61/376,725.
U.S. Appl. No. 61/640,530.
Notice of Abandonment mailed Mar. 14, 2014 for U.S. Appl. No. 13/442,850.
Examiner Interview Summary mailed Dec. 30, 2011 for U.S. Appl. No. 12/577,326.
Notice of Allowance mailed Feb. 24, 2012 for U.S. Appl. No. 12/577,326.
Office Action mailed Jun. 7, 2012 for Canadian Patent Application No. 2,740,358 filed Oct. 12, 2009.
European Search Opinion and Supplementary European Search Report for Application No. EP2009820037.1, mailed on Aug. 14, 2012.
U.S. Appl. No. 61/646,348.
International Search Report for International (PCT) Patent Application No. PCT/US2009/060386, mailed Nov. 25, 2009.
Written Opinion for International (PCT) Patent Application No. PCT/US2009/060386, mailed Nov. 25, 2009.

(56) References Cited

OTHER PUBLICATIONS

International Preliminary Report on Patentability for international (PCT) Patent Application No. PCT/US2009/060386, mailed Apr. 21, 2011.
Office Action mailed Nov. 21, 2011 for U.S. Appl. No. 12/577,326.
Notice of Abandonment mailed Dec. 10, 2013 for Canadian Patent Application No. 2,740,358 filed Oct. 12, 2009.
Co-pending U.S. Appl. No. 14/187,252, filed Feb. 22, 2014.
Co-pending U.S. Appl. No. 14/302,408, filed Jun. 11, 2014.
Co-pending U.S. Appl. No. 14/339,382, filed Jul. 23, 2014.
Co-pending U.S. Appl. No. 14/327,519, flied Jul. 9, 2014.
Co-pending U.S. Appl. No. 14/187,302, filed Feb. 23, 2014.
Further Processing Decision for Application No. EP2009820037.1, mailed on Jul. 16, 2013.
Office Action mailed Jul. 12, 2013 for U.S. Appl. No. 13/219,683, filed Aug. 28, 2011 (including PTO-892).
Office Action mailed Nov. 12, 2013 for U.S. Appl. No. 13/219,683, filed Aug. 28, 2011.
Office Action mailed Jul. 8, 2013 for U.S. Appl. No. 13/184,332, filed Jul. 15, 2011 (including PTO-892).
Office Action mailed Oct. 18, 2013 for U.S. Appl. No. 13/184,332, flied Jul. 15, 2011.
Office Action mailed Aug. 14, 2013 for U.S. Appl. No. 13/423,413, filed Mar. 19, 2012 (including PTO-892).
Office Action mailed Oct. 18, 2013 for U.S. Appl. No. 13/218,145, filed Aug. 25, 2011.
Office Action mailed Jul. 1, 2013 for U.S. Appl. No. 13/218,145, filed Aug. 25, 2011 (including PTO-892).
Office Action mailed Sep. 4, 2013 for Chinese Patent Application No. 200980152835.6 filed Oct. 12, 2009 (with translation).
Examiner Interview Summary mailed Dec. 16, 2013 for U.S. Appl. No. 13/221,890.
Office Action mailed Apr. 17, 2013 for U.S. Appl. No. 13/442,850, filed Apr. 9, 2012 (including PTO-892).
Office Action mailed Sep. 9, 2013 for U.S. Appl. No. 13/442,850, filed Apr. 9, 2012 (including PTO-892).
Office Action mailed Jan. 30, 2013 for Canadian Patent Application No. 2,737,322 filed Apr. 14, 2011.
Office Action mailed Oct. 3, 2013 for Canadian Patent Application No. 2,737,322 filed Apr. 14, 2011.
Office Action mailed May 6, 2013 for U.S. Appl. No. 13/221,890, filed Aug. 30, 2011 (including PTO-892).
Office Action mailed Aug. 22, 2013 for U.S. Appl. No. 13/221,890, filed Aug. 30, 2011.
Office Action mailed Jul. 22, 2013 for U.S. Appl. No. 13/451,468, filed Apr. 19, 2012 (including PTO-892).
Notice of Allowance mailed Jan. 31, 2014 for U.S. Appl. No. 13/451,468, filed Apr. 19, 2012.
Examiner Interview Summary mailed Jan. 8, 2014 for U.S. Appl. No. 13/219,683.
Notice of Allowance mailed Jan. 7, 2014 for U.S. Appl. No. 13/184,332, filed Jul. 15, 2011.
Notice of Allowance mailed Jan. 6, 2014 for U.S. Appl. No. 13/221,890, filed Aug. 30, 2011.
Notice of Allowance mailed Jan. 9, 2014 for U.S. Appl. No. 13/423,413, filed Mar. 19, 2012.
Notice of Allowance mailed Dec. 24, 2013 for U.S. Appl. No. 13/072,656, filed Mar. 25, 2011.
Notice of Allowance mailed Jan. 7, 2014 for U.S. Appl. No. 13/218,145, filed Aug. 25, 2011.
Office Action mailed Feb. 19, 2014 for U.S. Appl. No. 13/219,683, filed Aug. 28, 2011.
Examiner Interview Summary mailed Feb. 27, 2014 for U.S. Appl. No. 13/219,683.
Notice of Allowance mailed Mar. 4, 2014 for U.S. Appl. No. 13/219,683.
European Examination Report mailed on Feb. 27, 2014 for Application No. EP2009820037.1 filed Dec. 5, 2011.
Office Action mailed Mar. 5, 2014 for Chinese Patent Application No. 200980152835.6 filed Oct. 12, 2009 (with translation).
Co-pending U.S. Appl. No. 14/176,119, filed Feb. 9, 2014.
Notice of Allowance mailed Jan. 31, 2014 for U.S. Appl. No. 13/451,468.
Office Action mailed Jun. 11, 2014 for Chinese Patent Application No. 200980152835.6 field Oct. 12, 2009 (with translation).
Notice of Allowance mailed Jun. 11, 2014 for U.S. Appl. No. 13/832,575 (including PTO-892).
Notice of Allowance mailed Jun. 19, 2014 for CA Application No. 2737322.
Notice of Allowance mailed Nov. 24, 2014 for U.S. Appl. No. 14/187,302.
Office Action mailed Nov. 20, 2014 for U.S. Appl. No. 14/187,252, filed Feb. 22, 2014.
Office Action mailed Apr. 16, 2015 for U.S. Appl. No. 13/832,520, filed Mar. 15, 2013.

\* cited by examiner

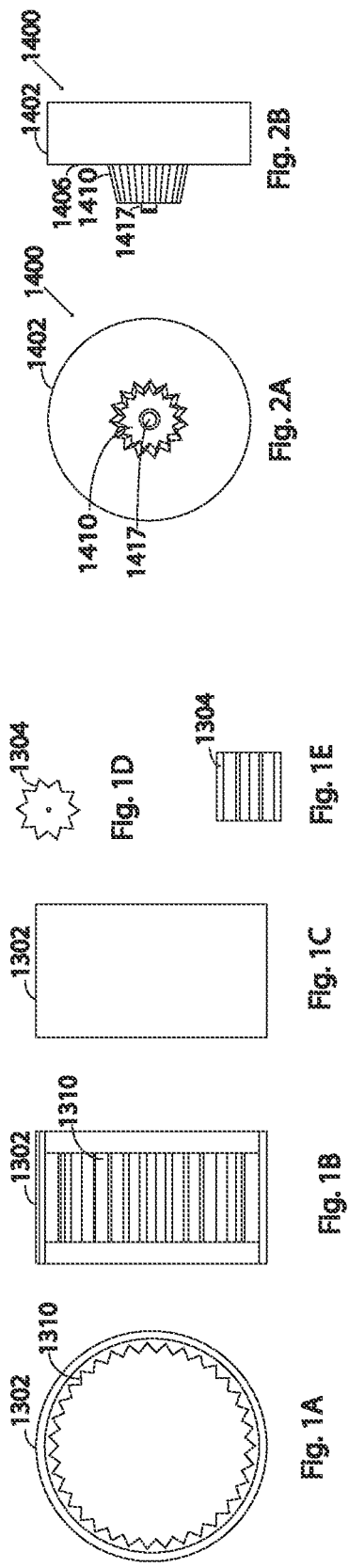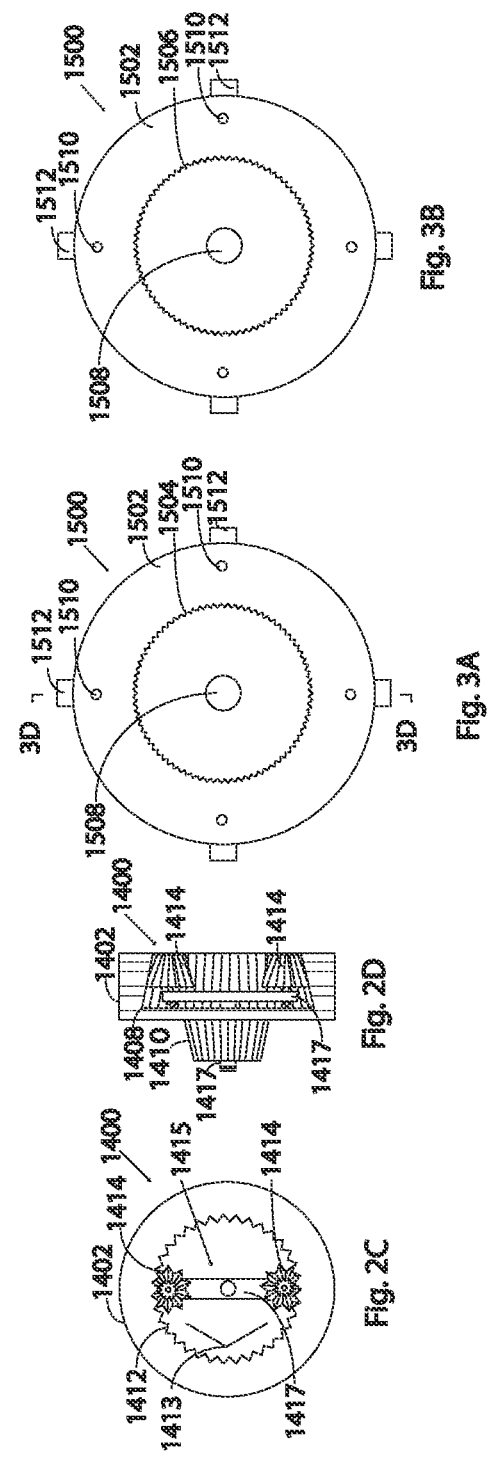

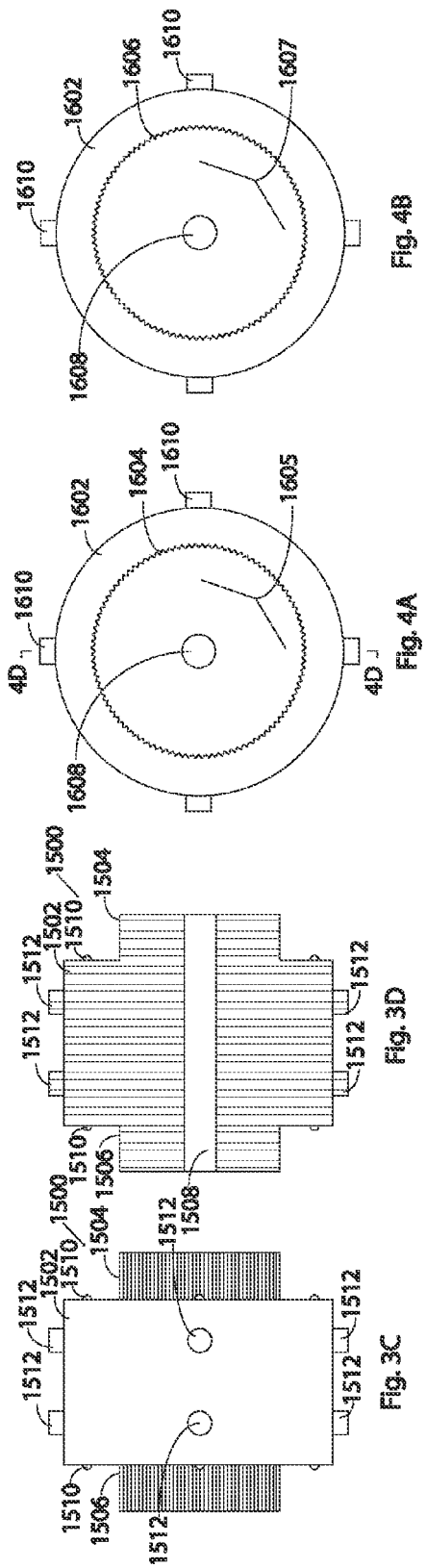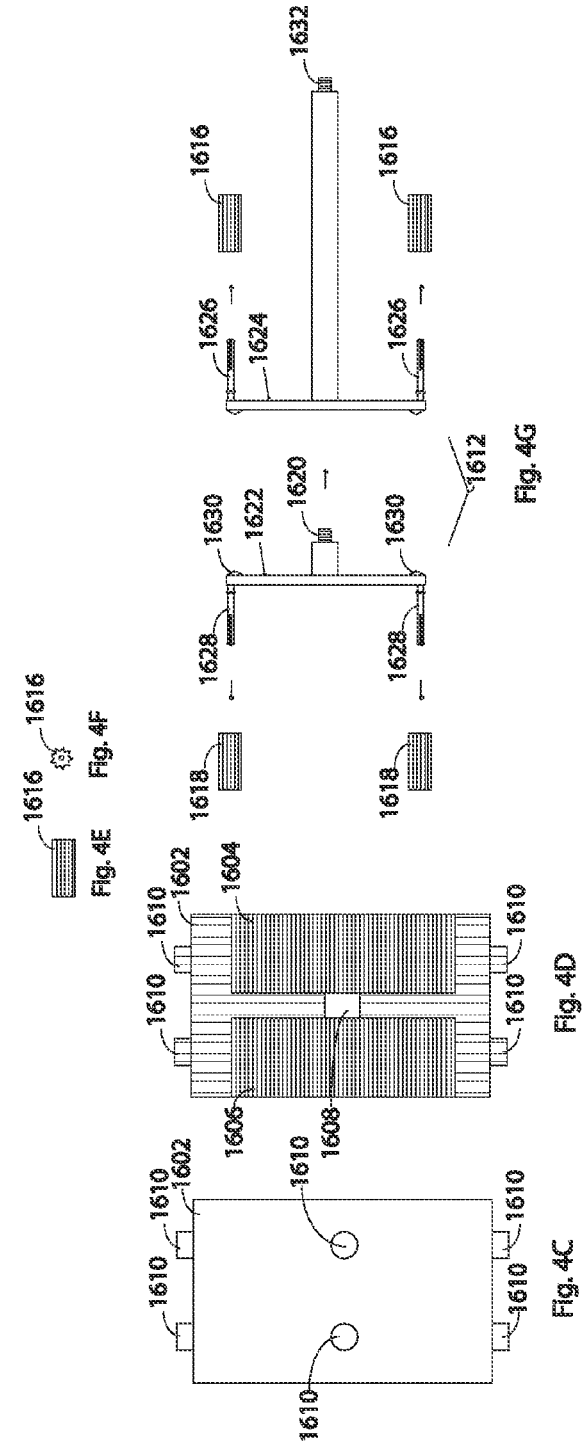

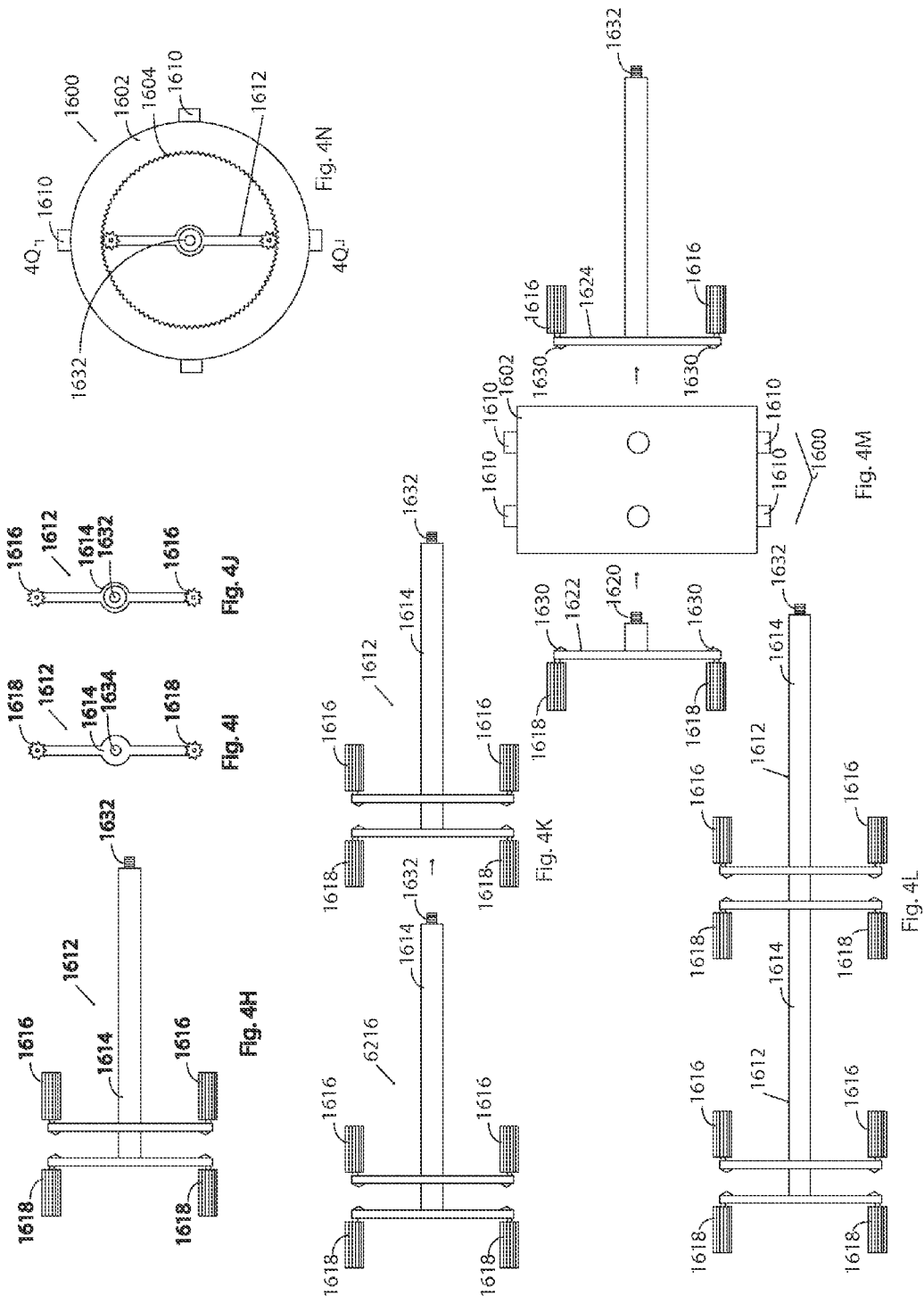

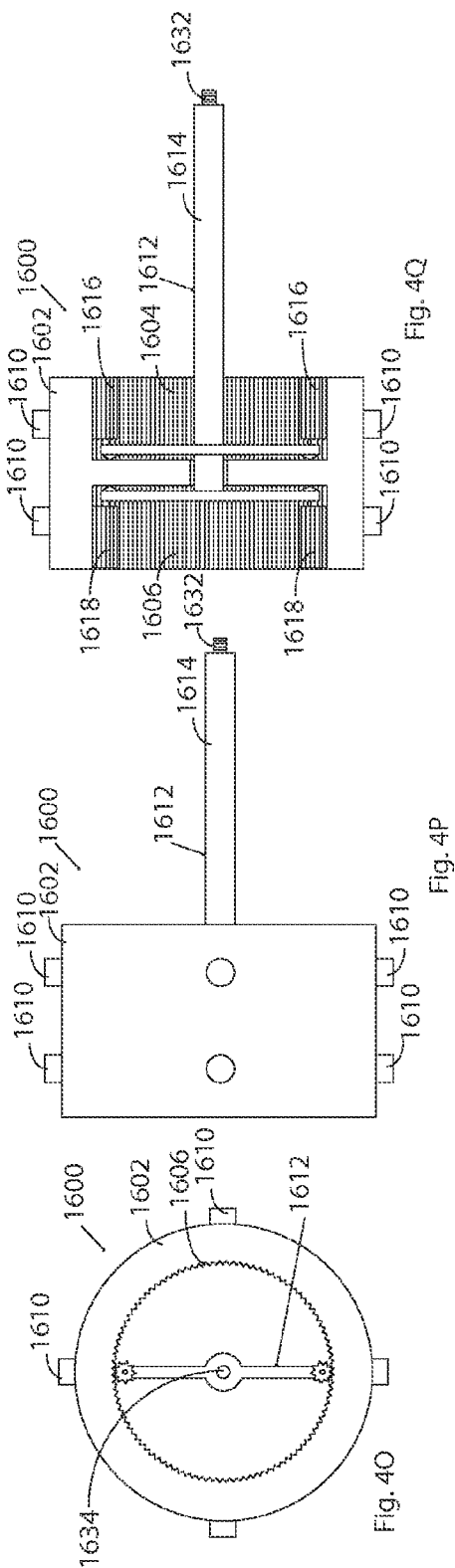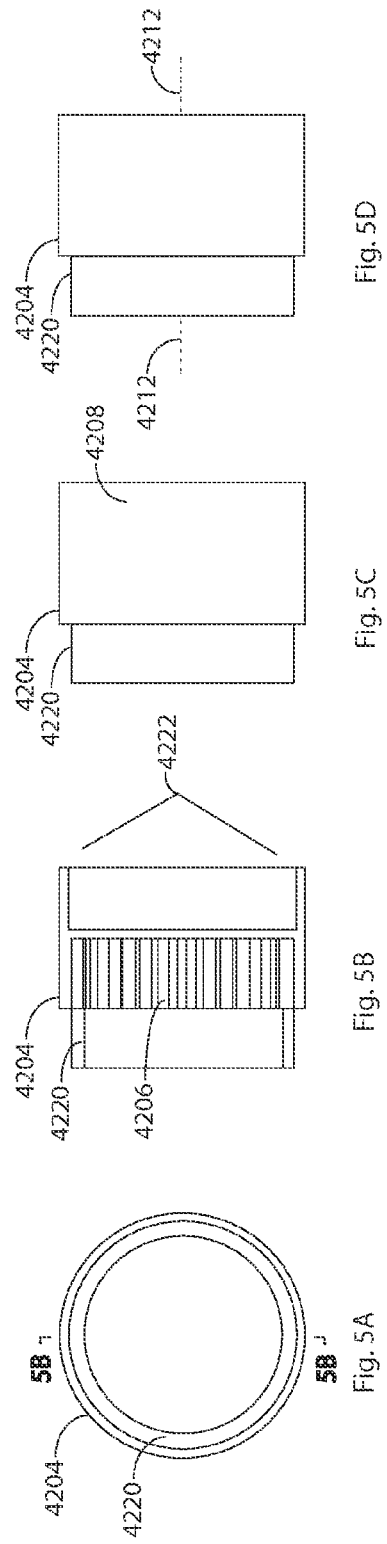

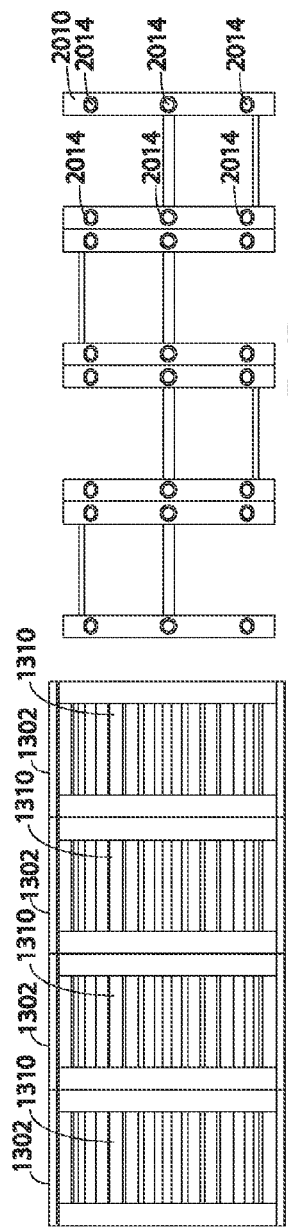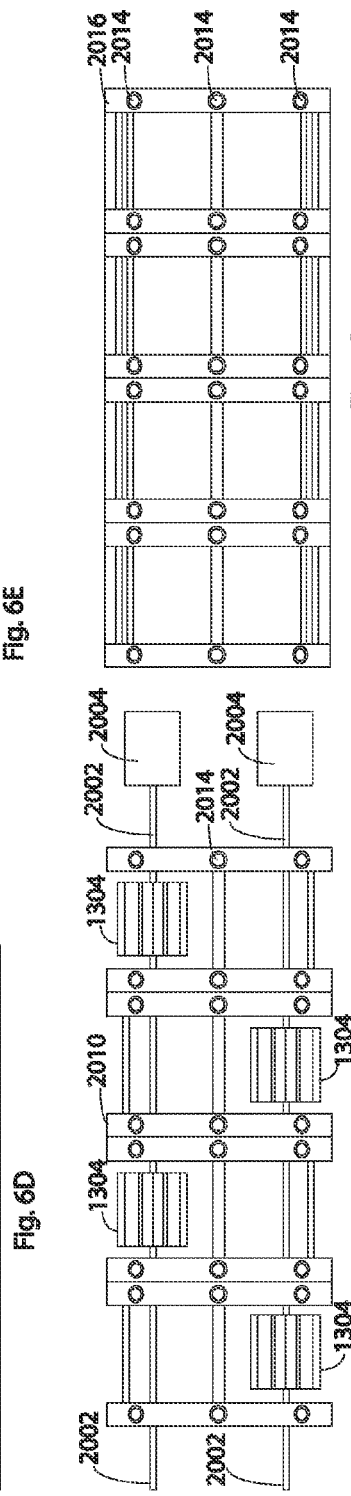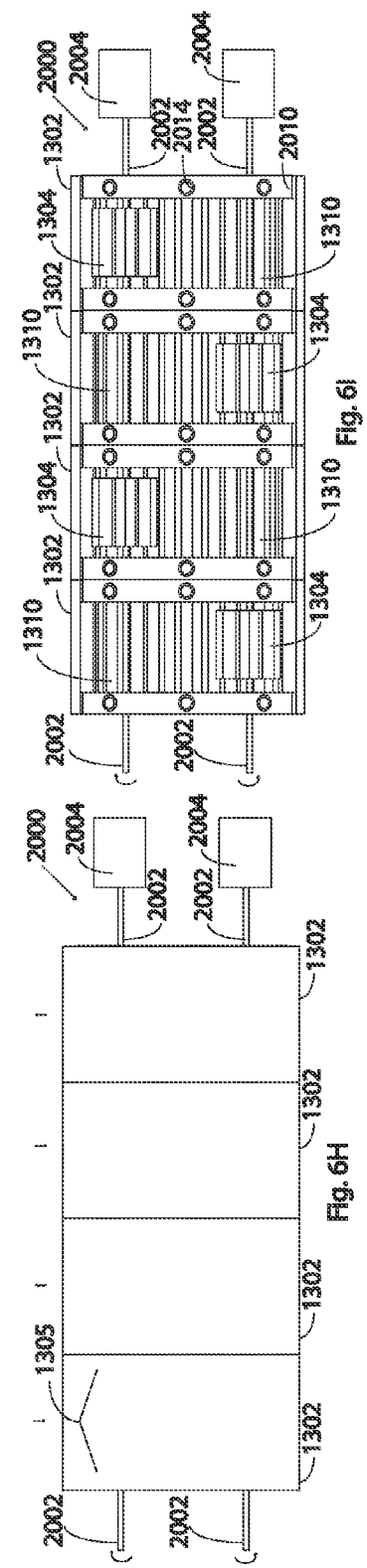

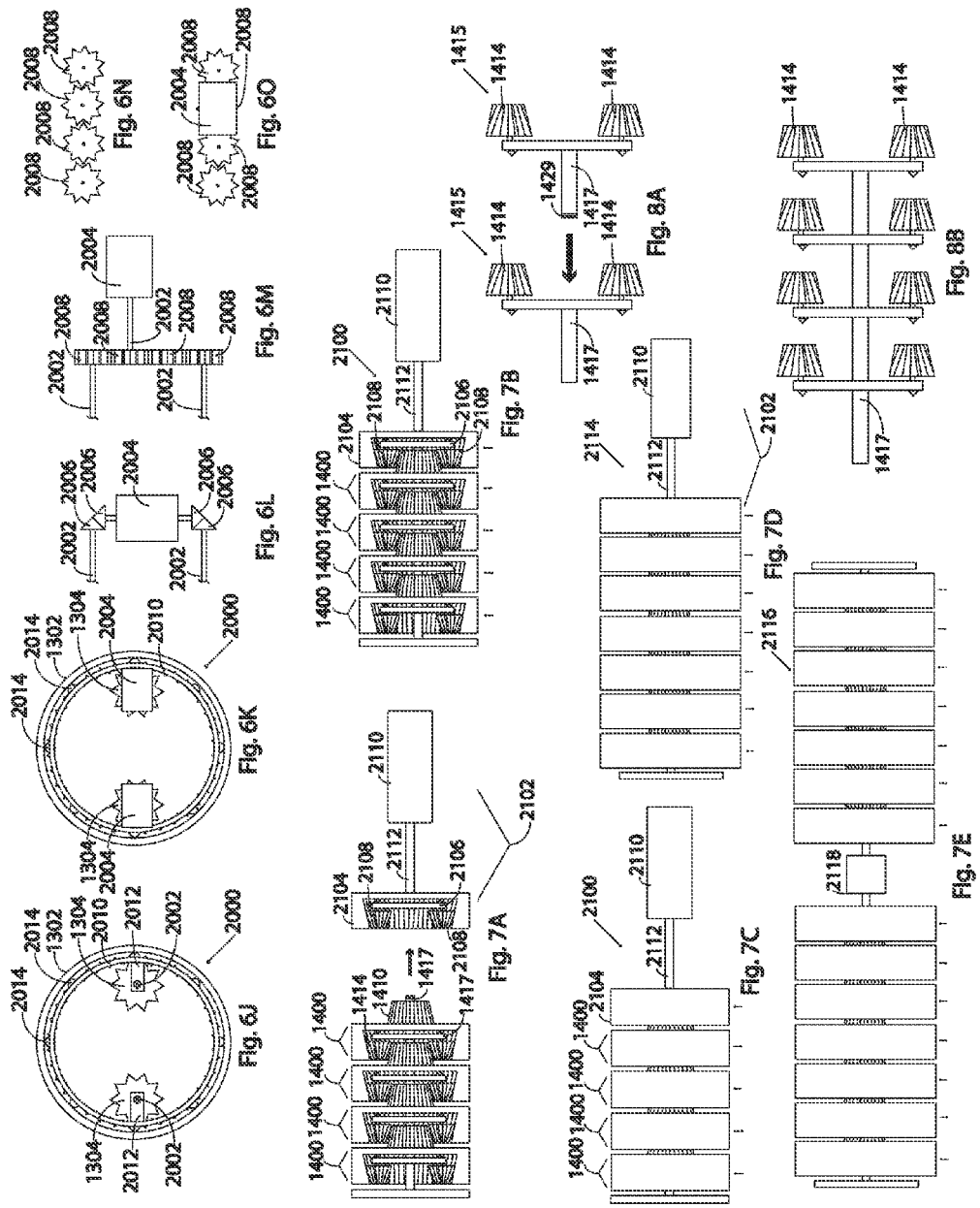

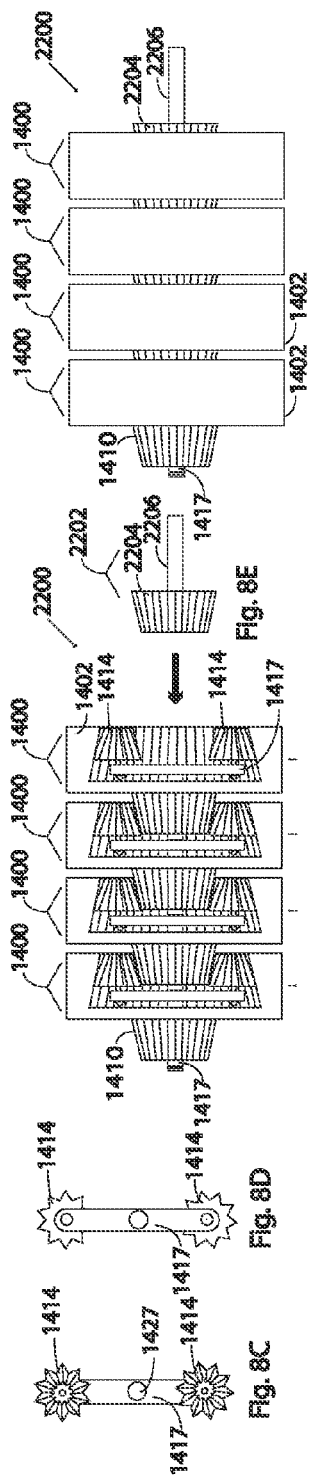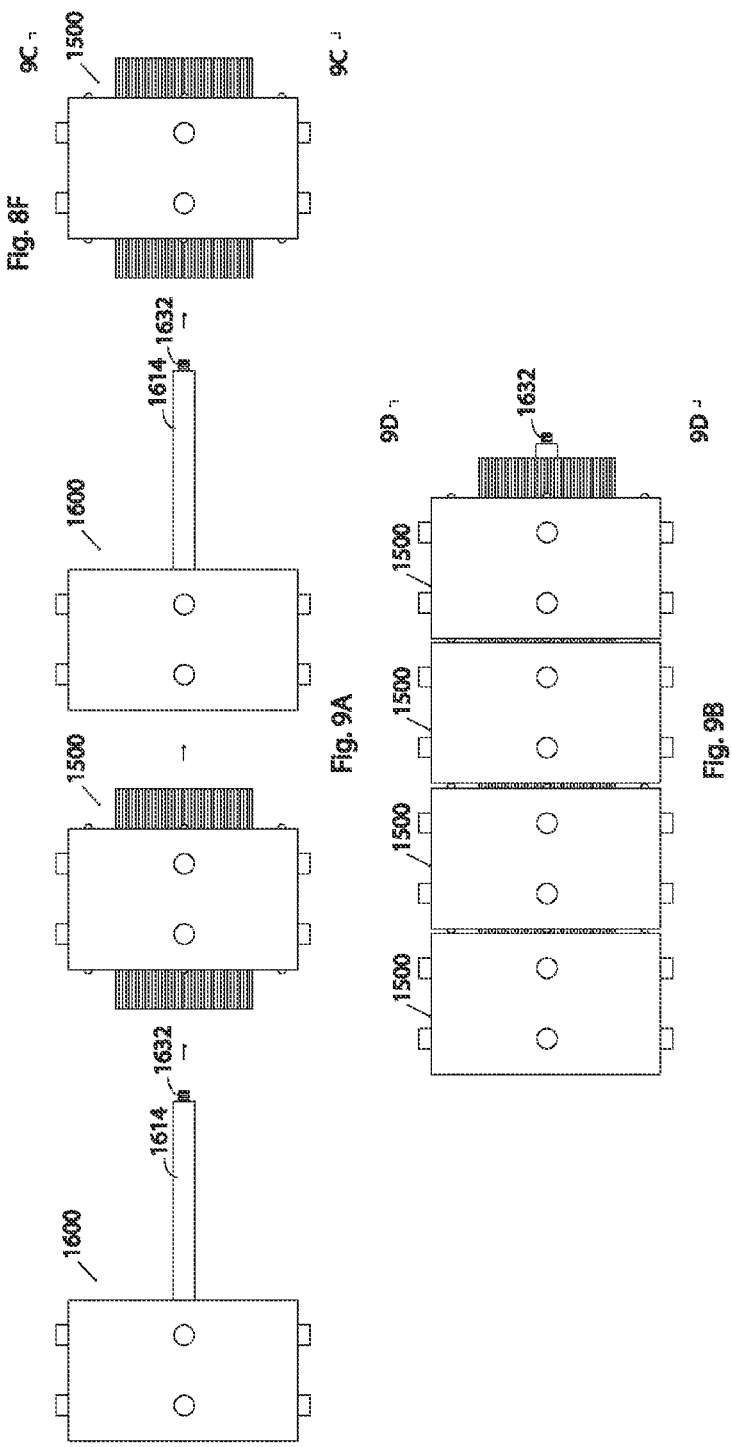

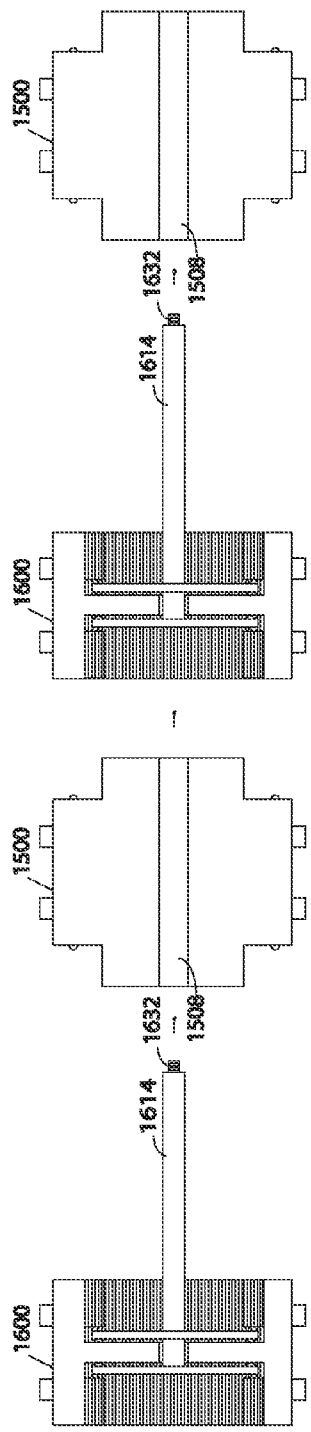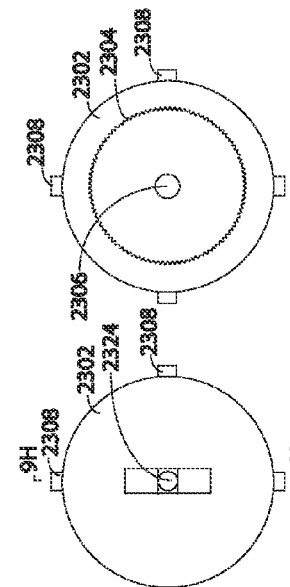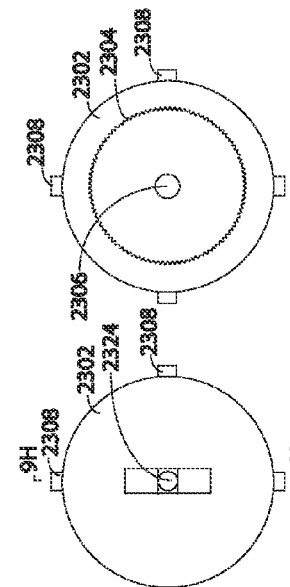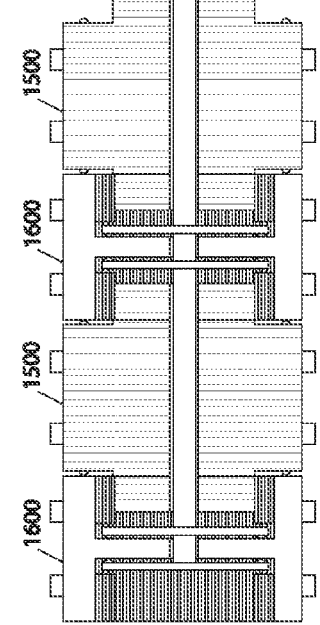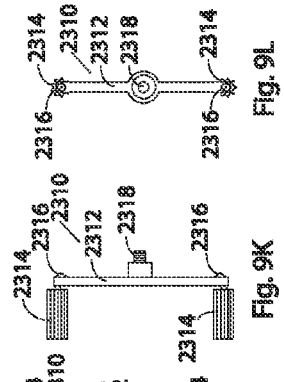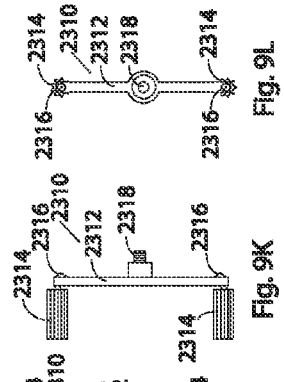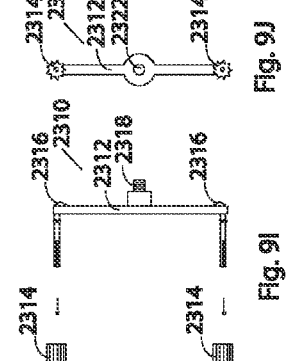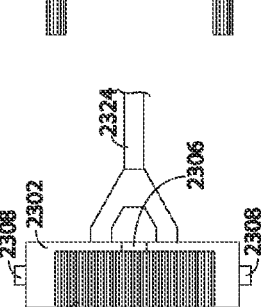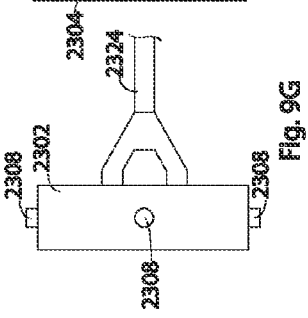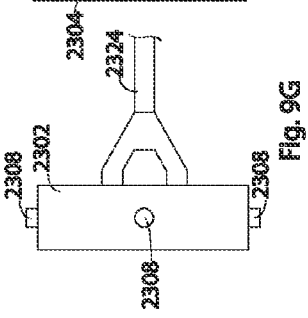

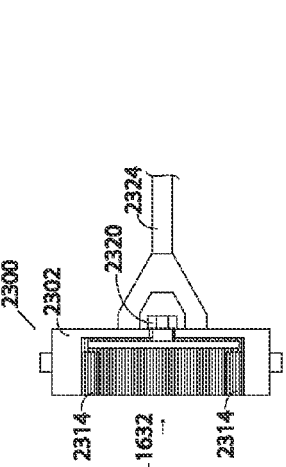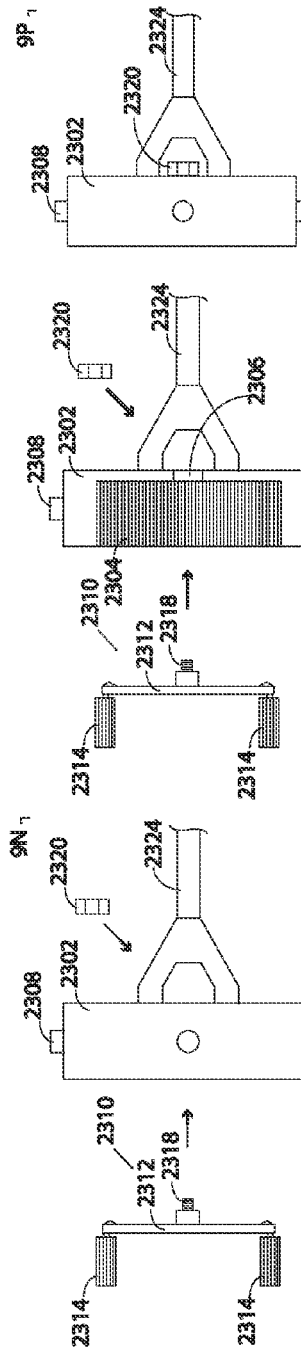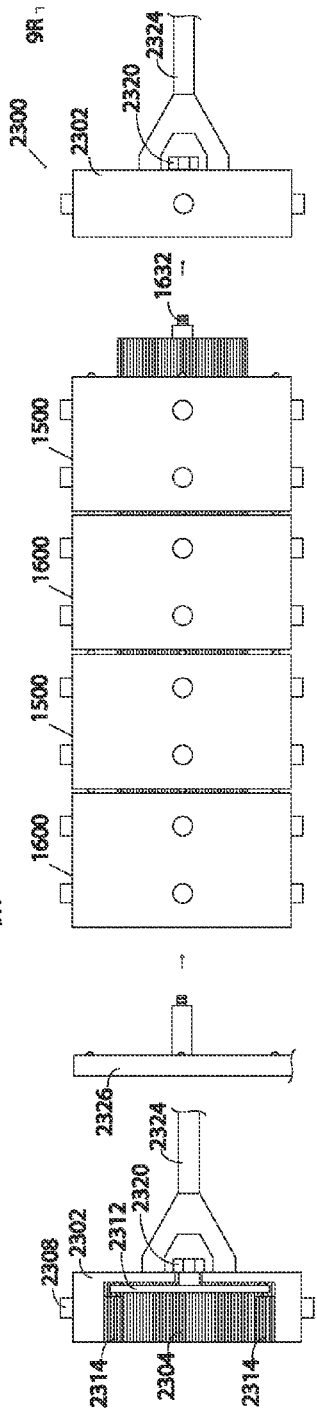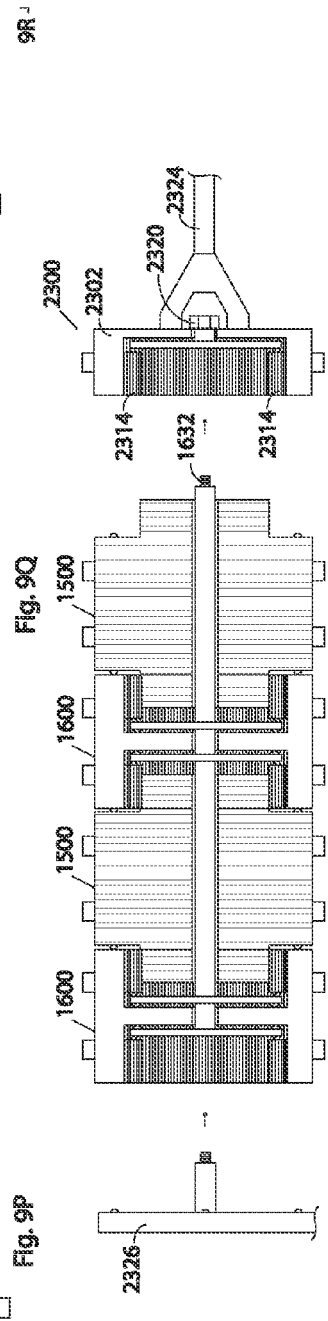

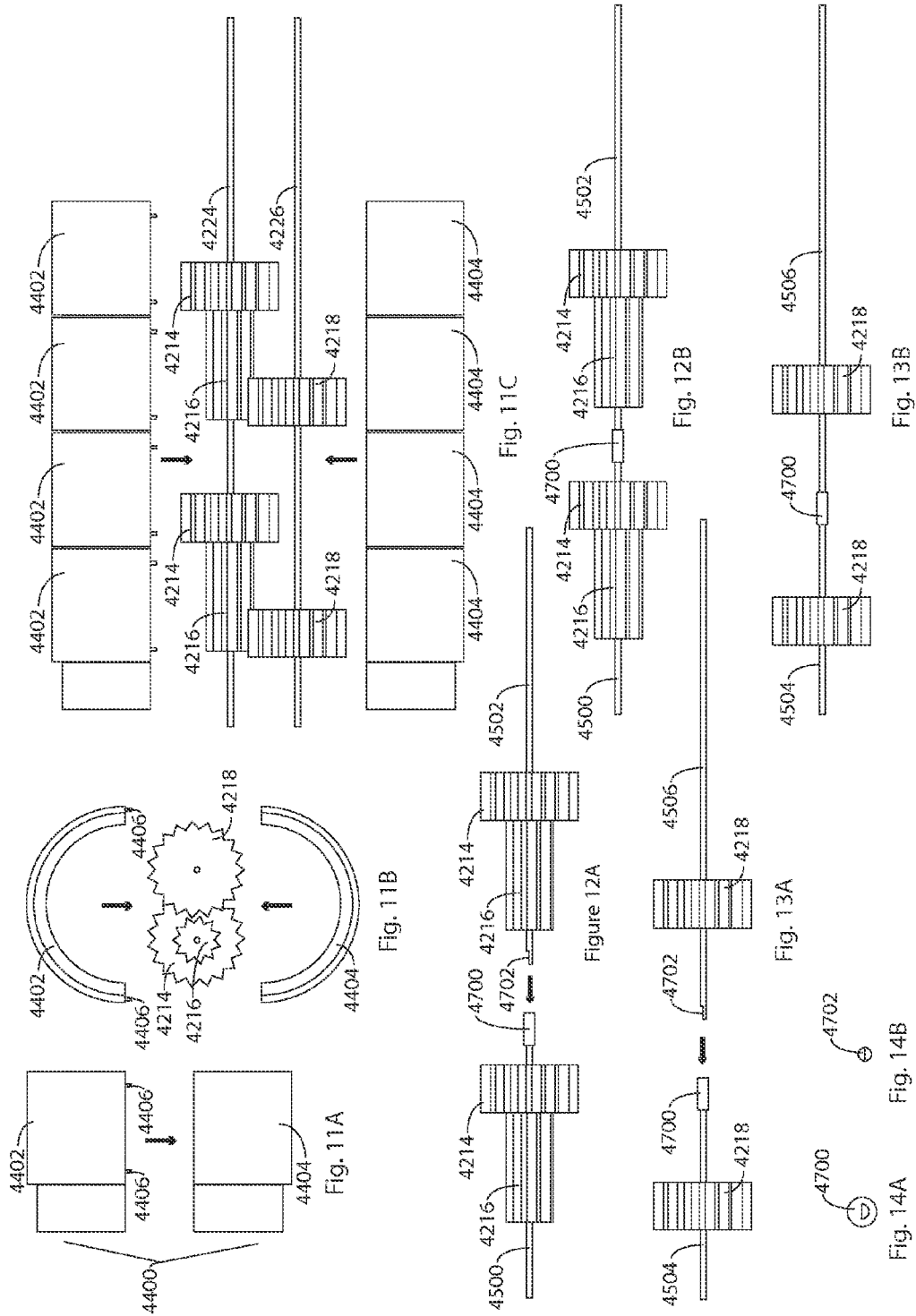

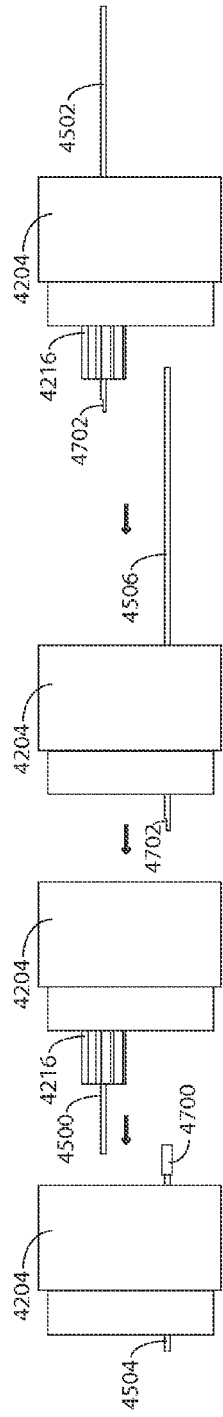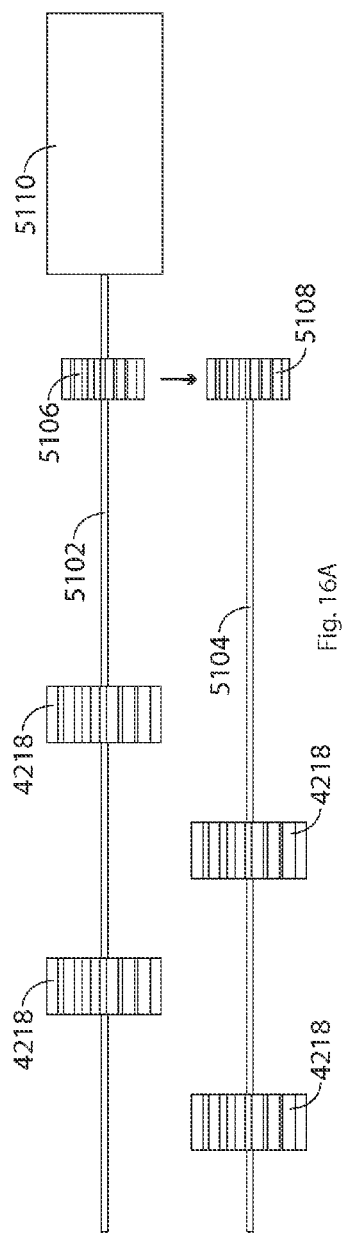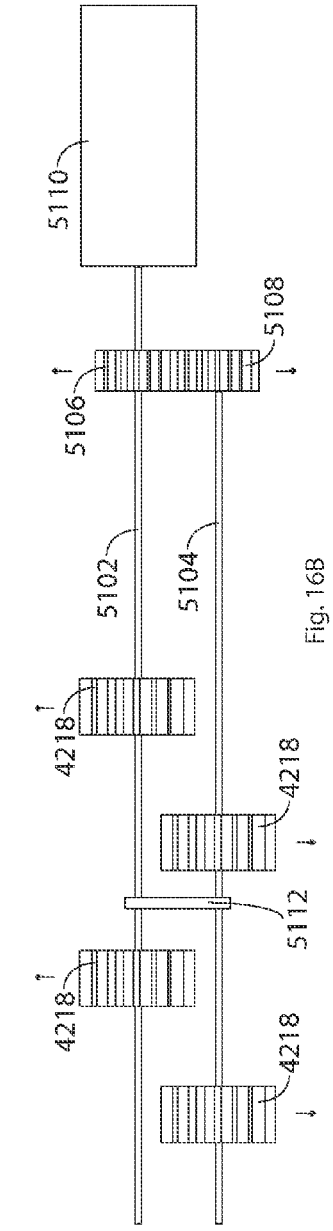

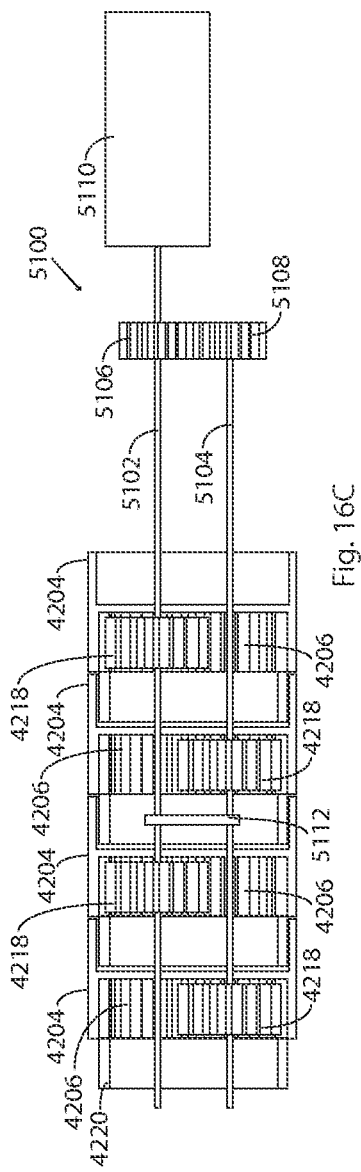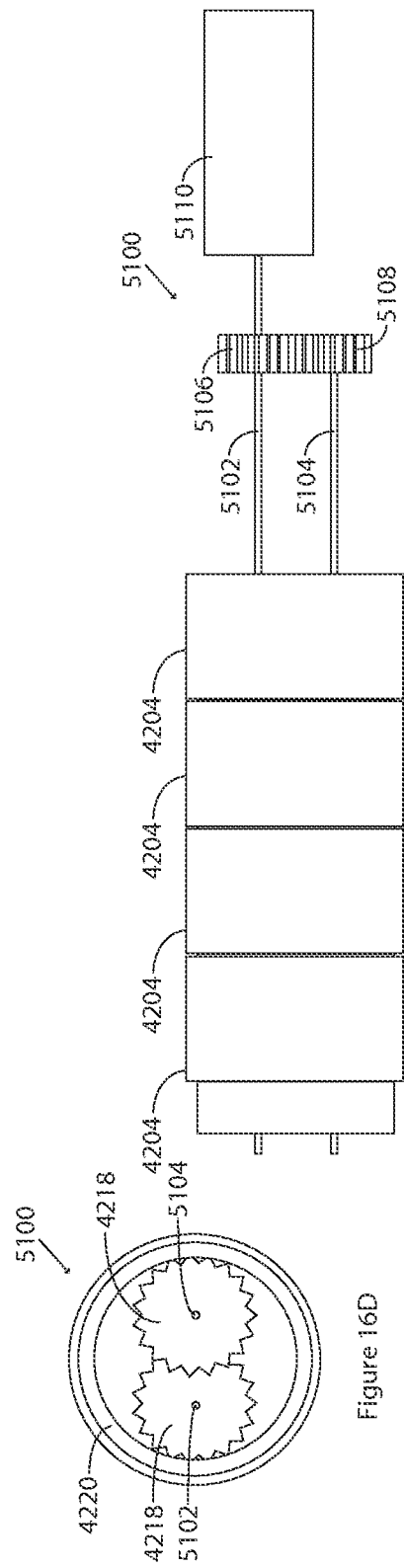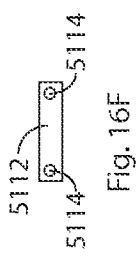

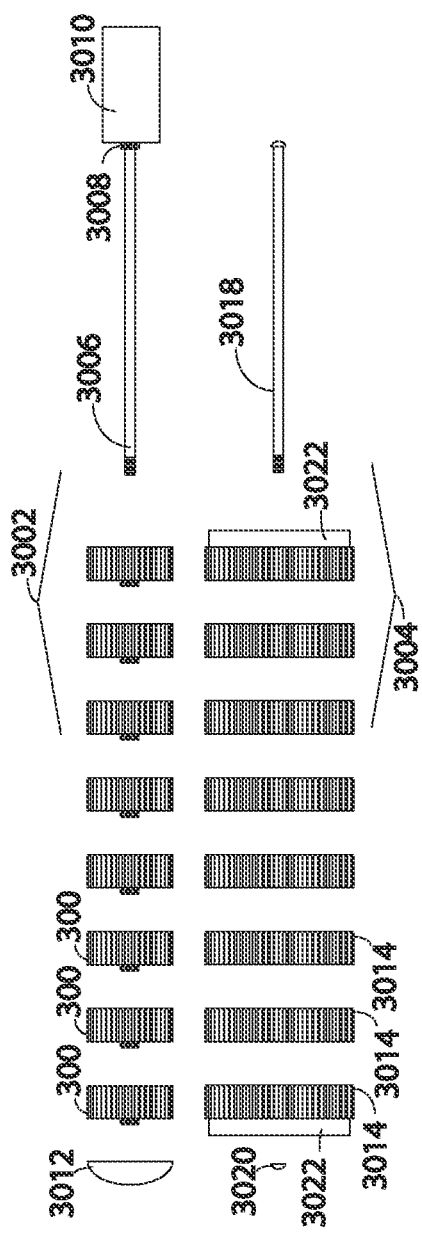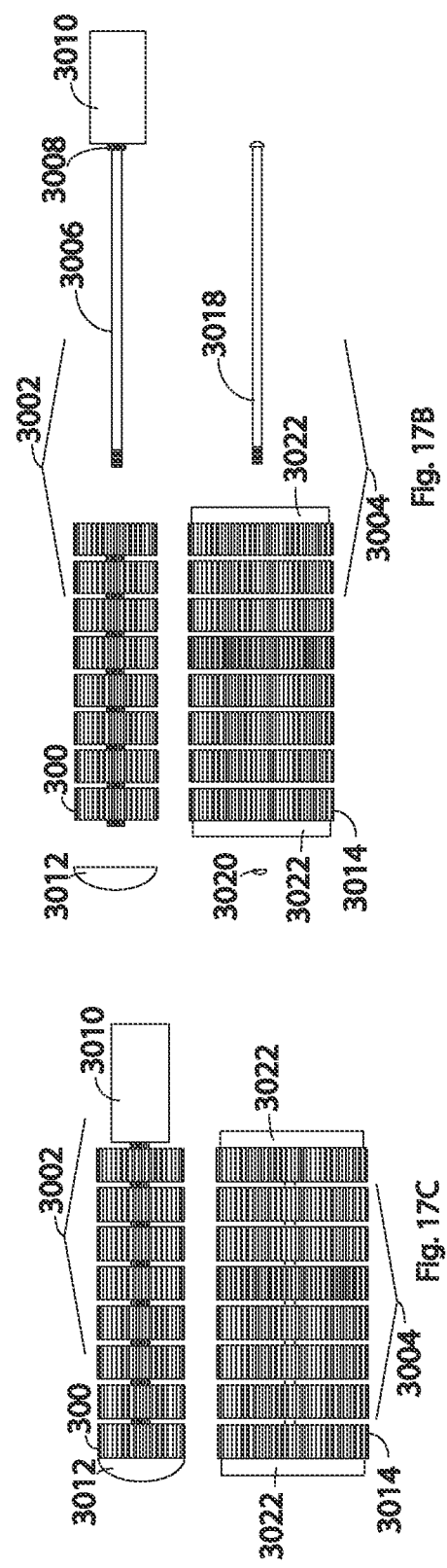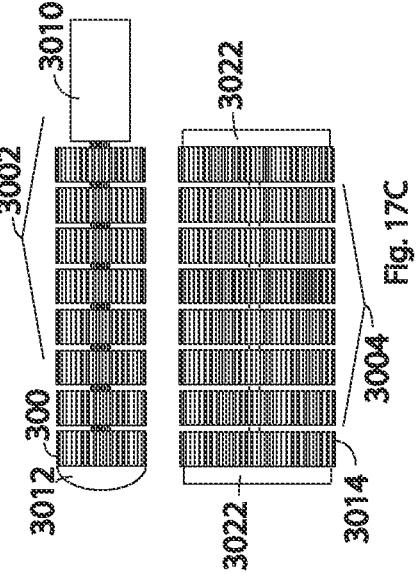

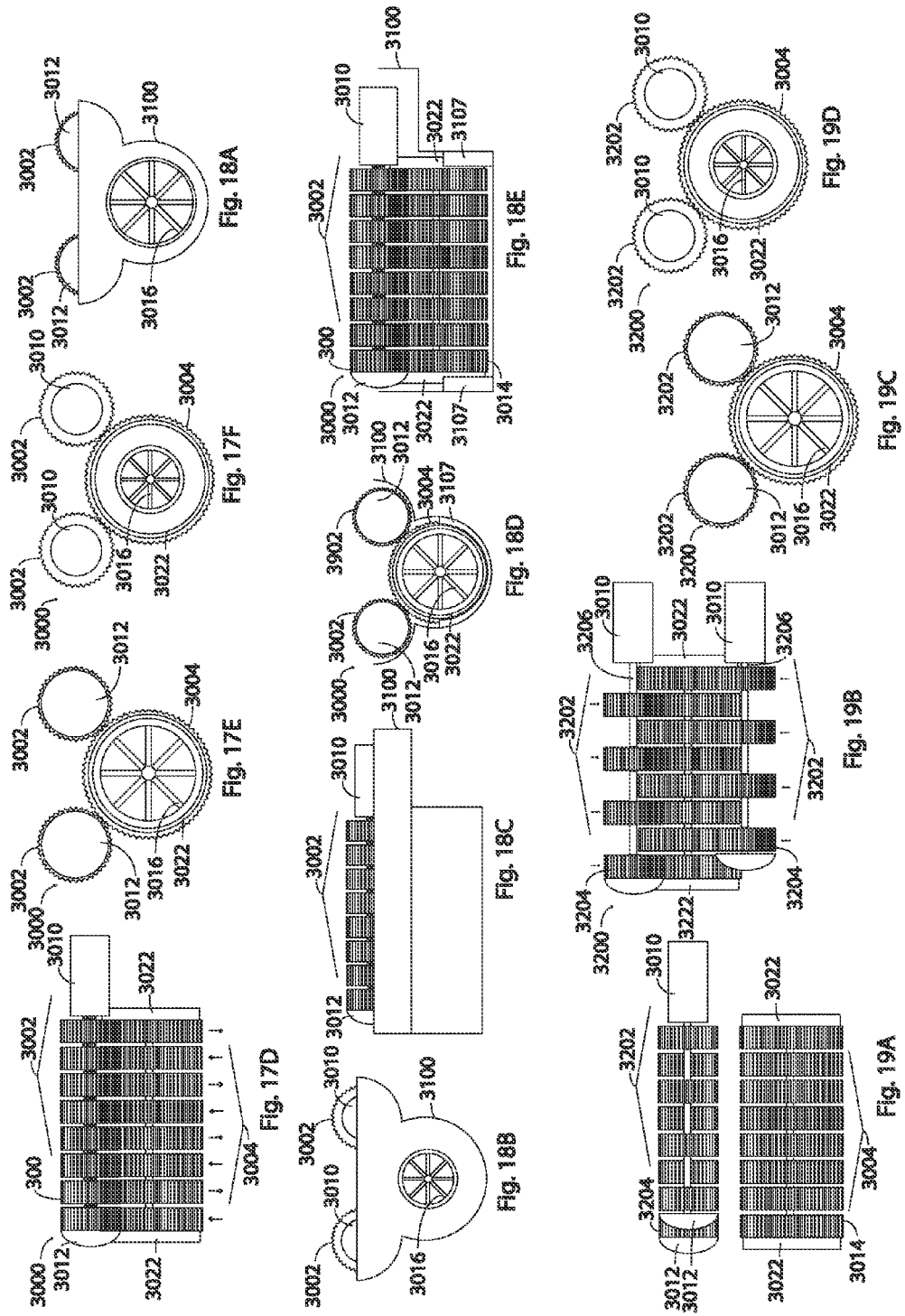

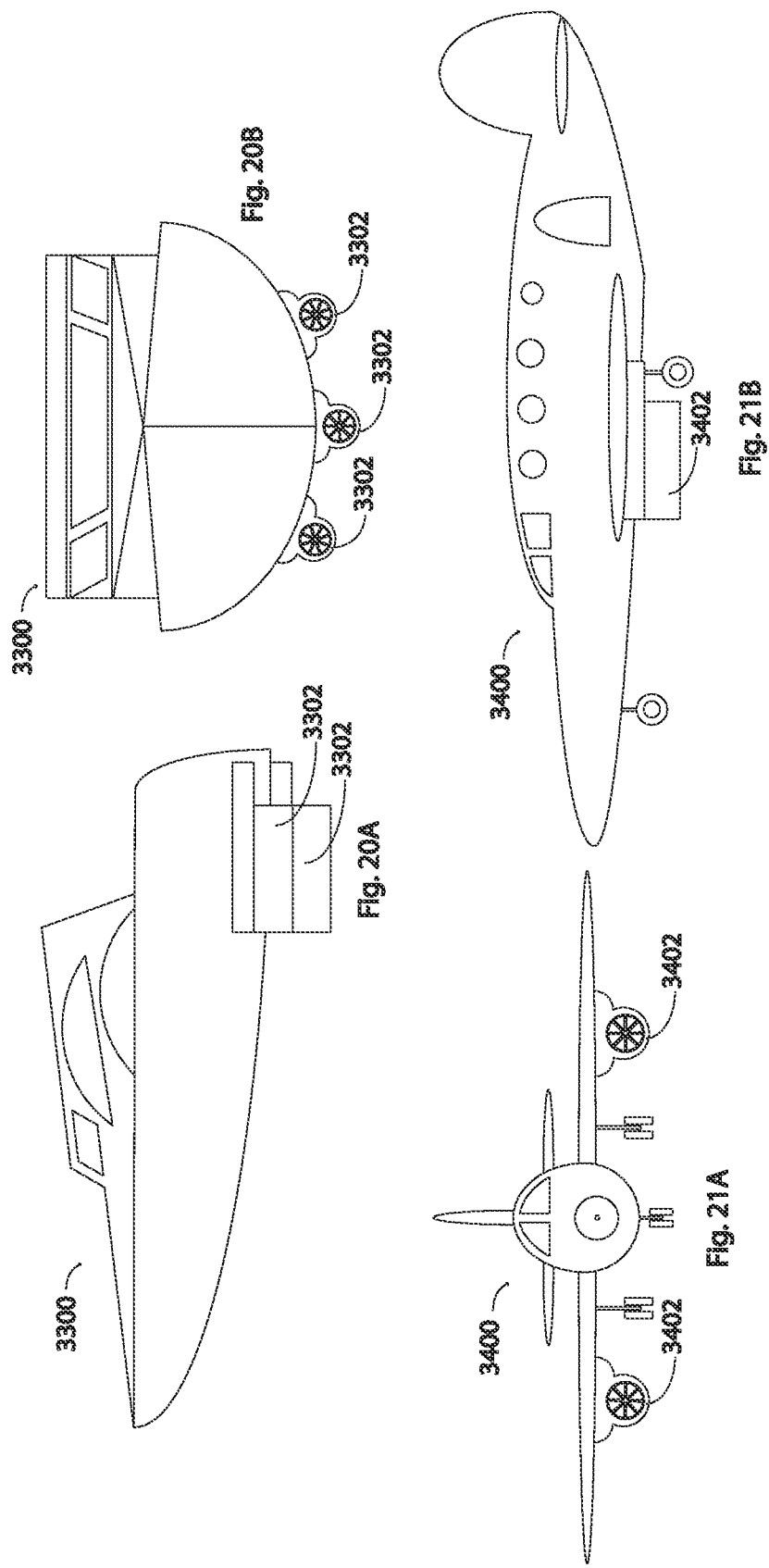

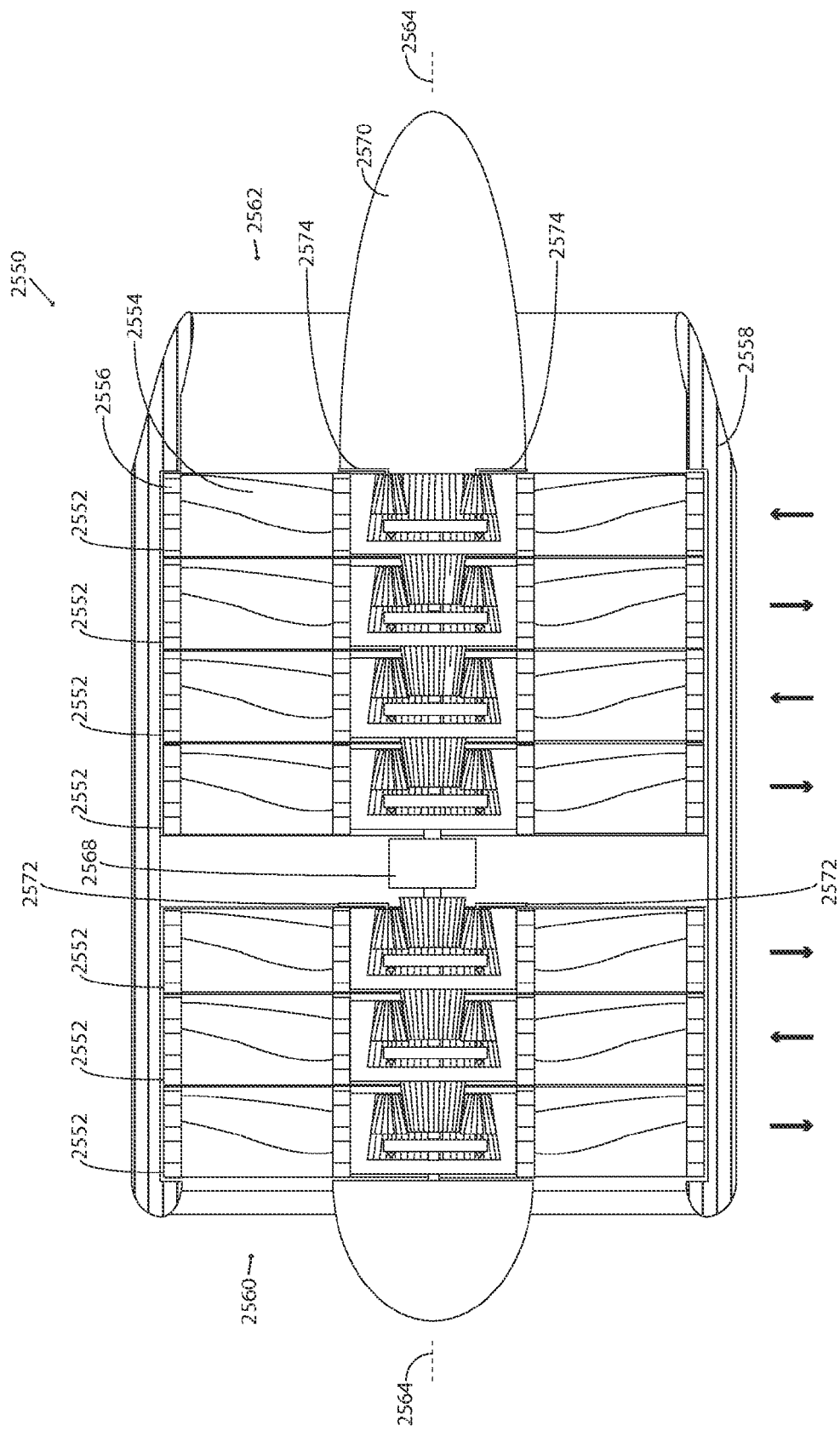

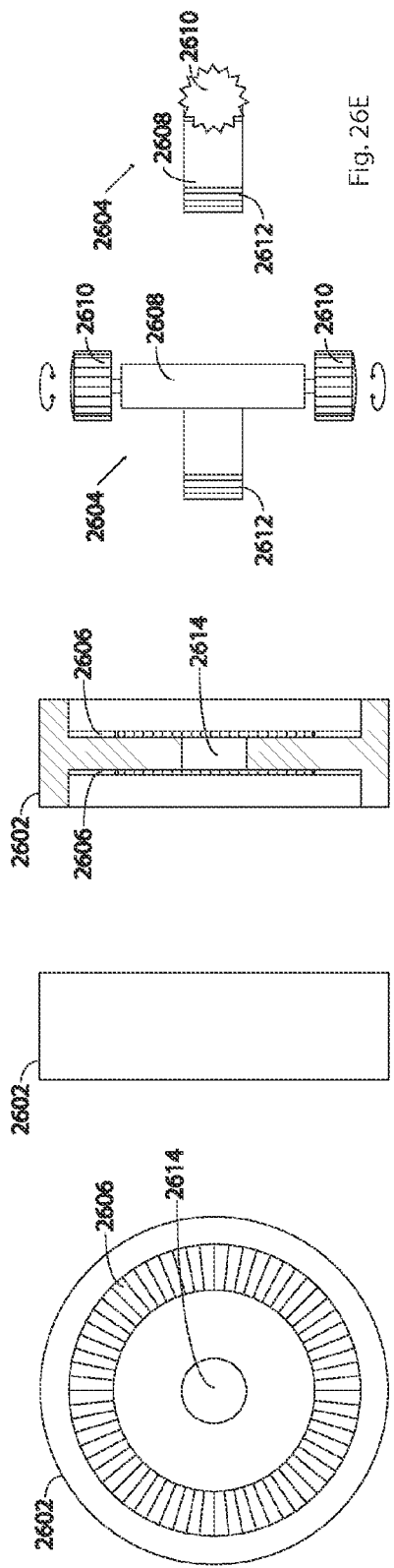
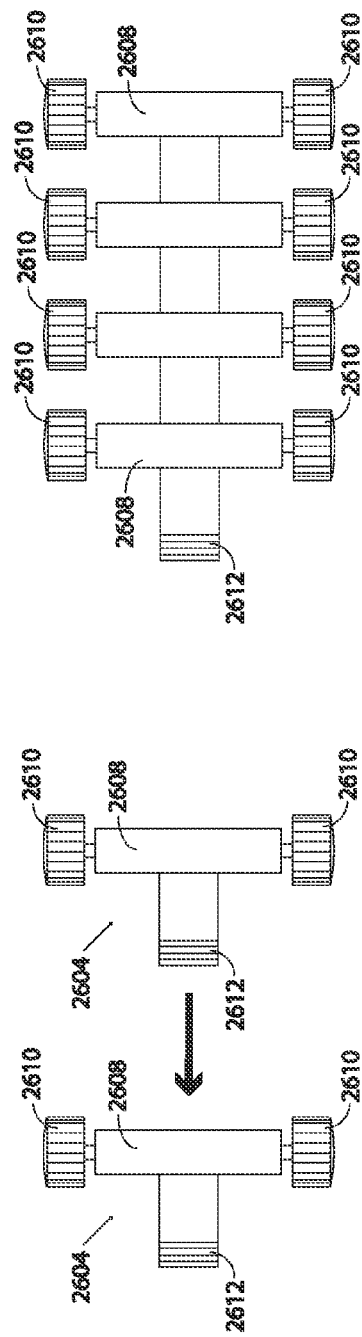

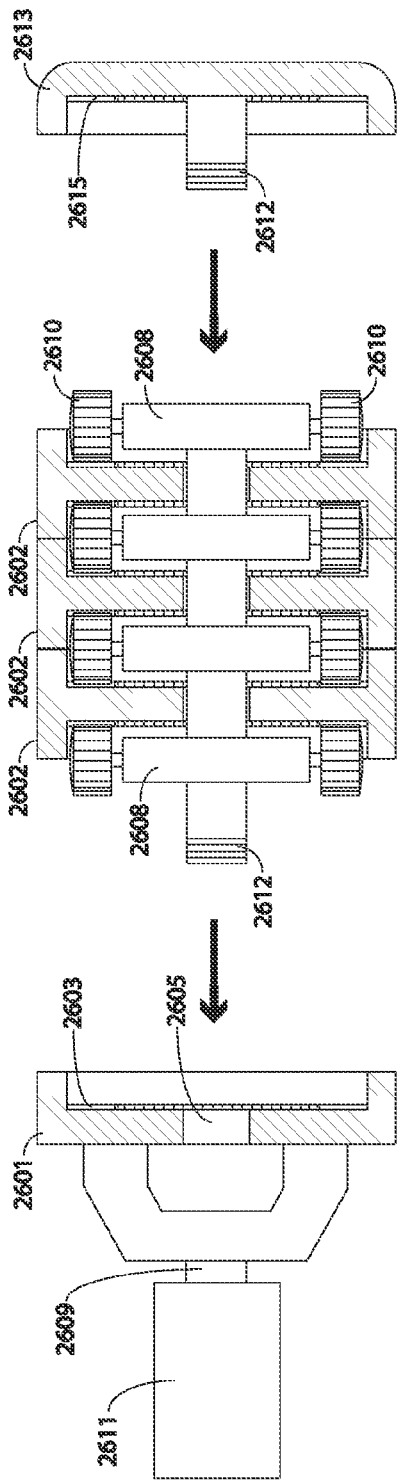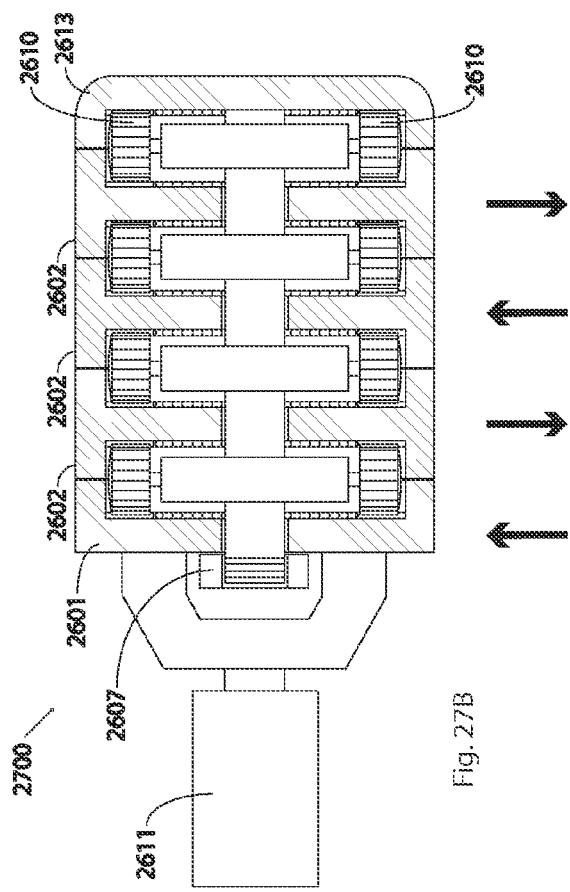

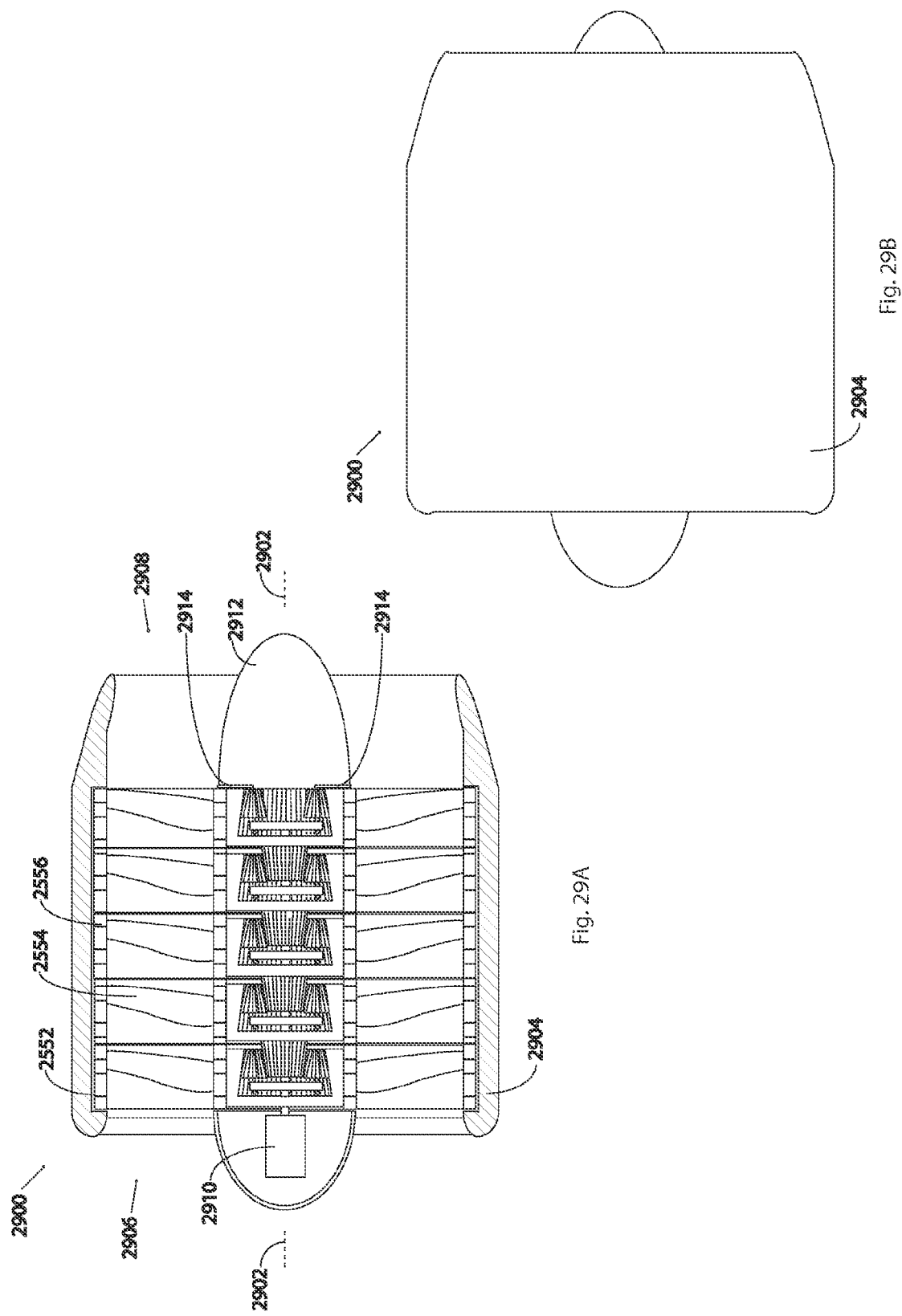

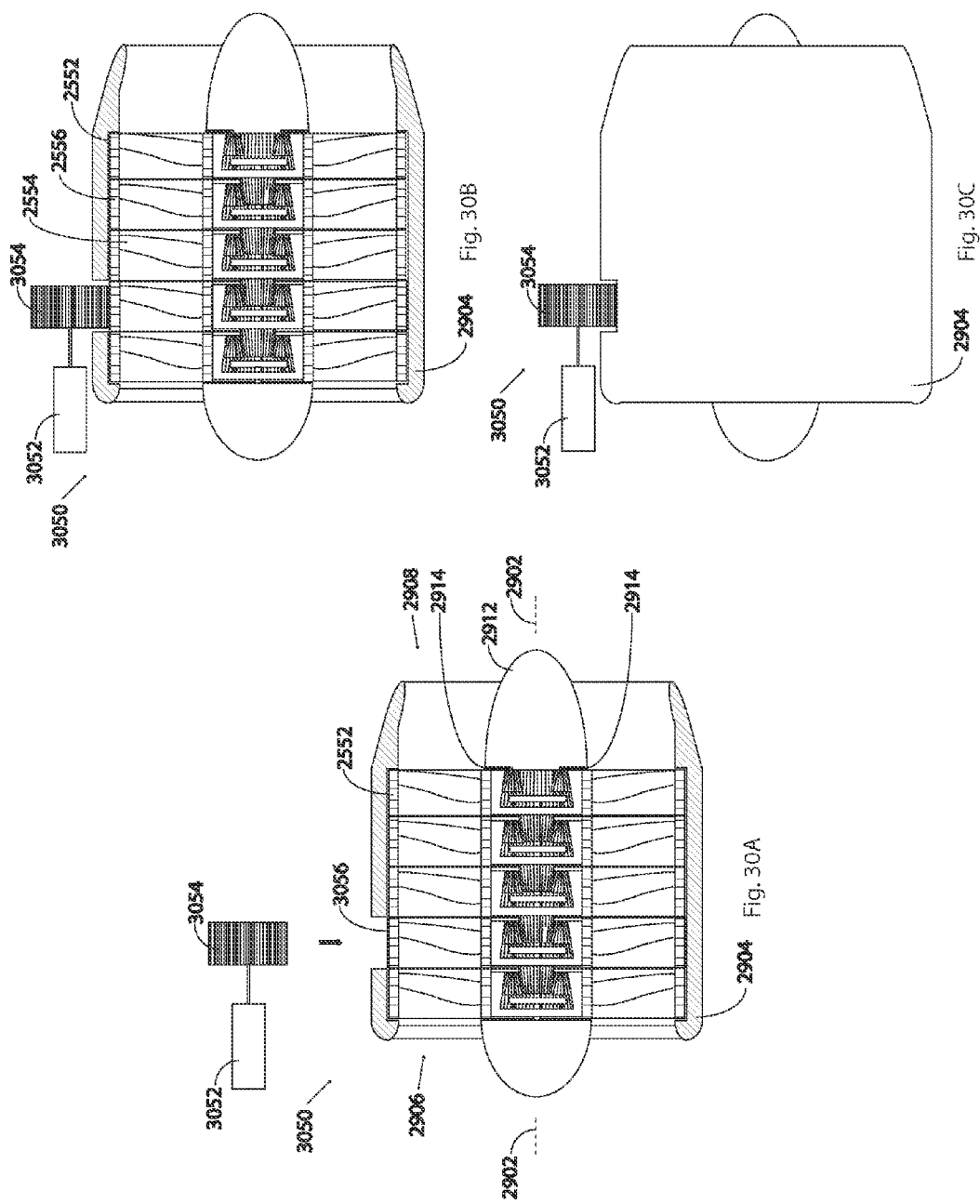

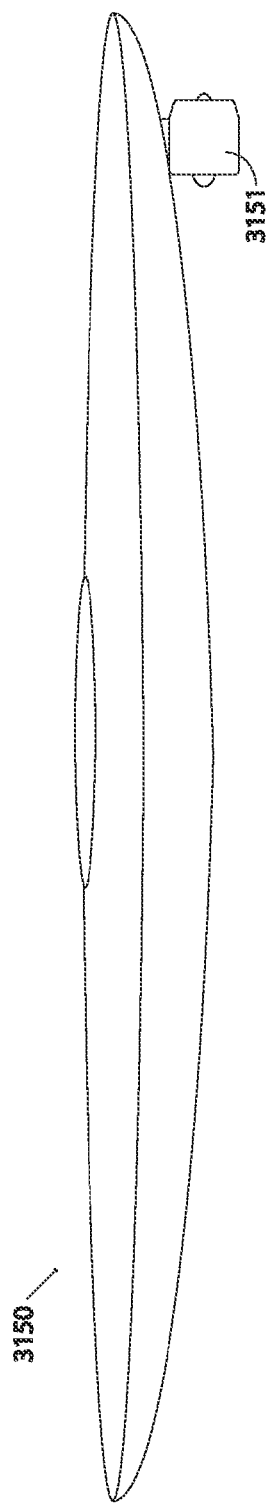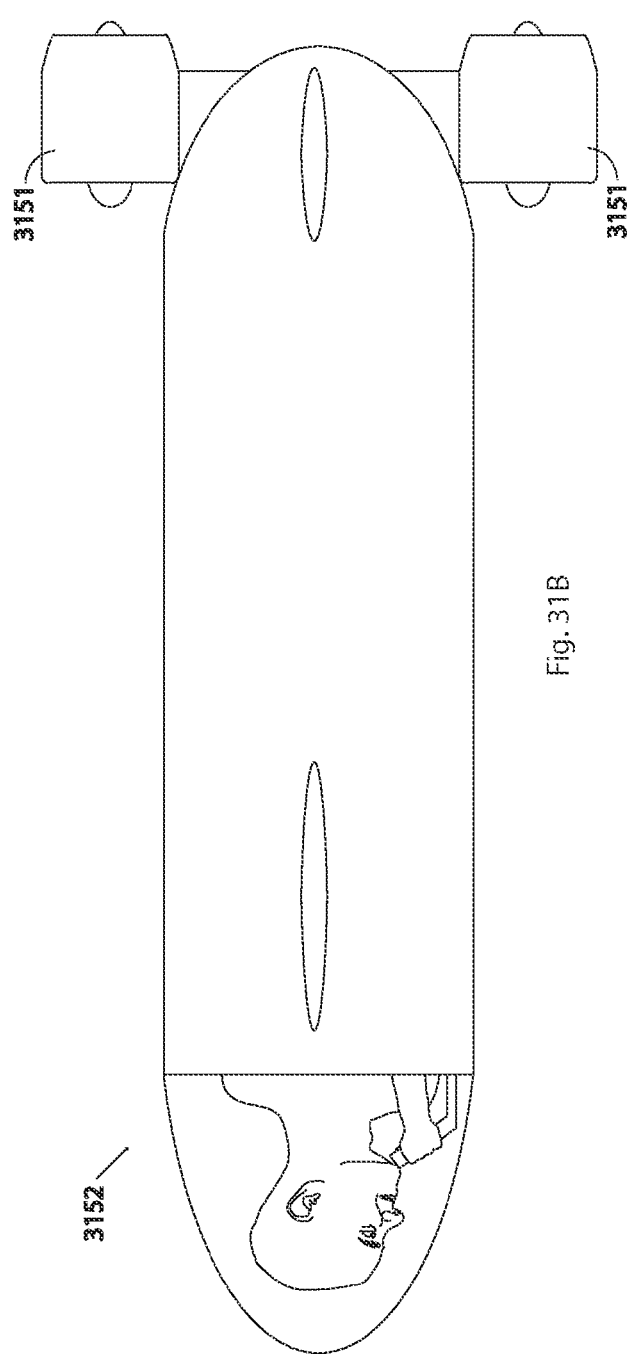
Fig. 31A
Fig. 31B

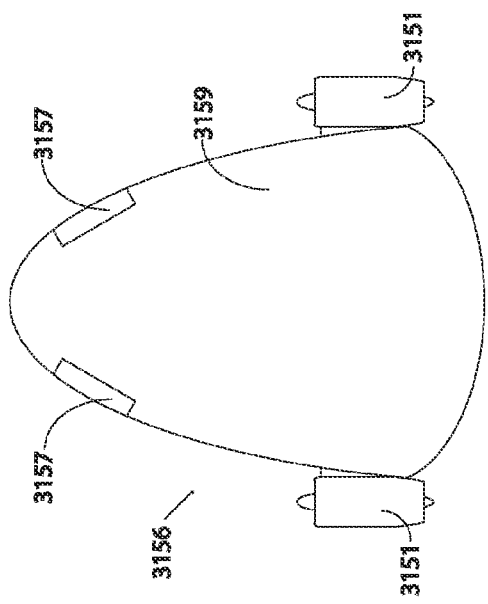
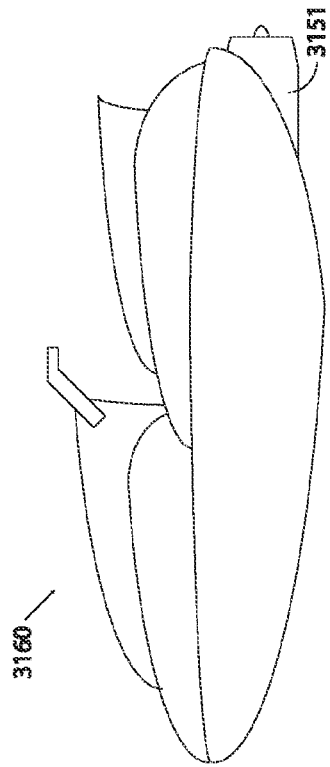
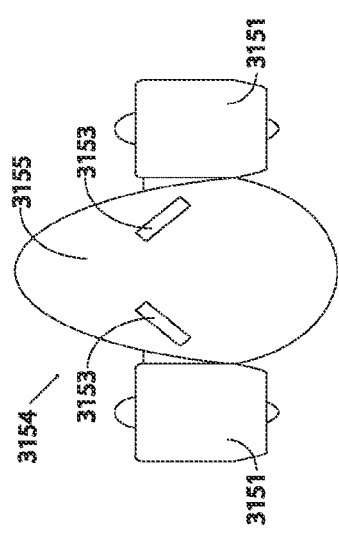
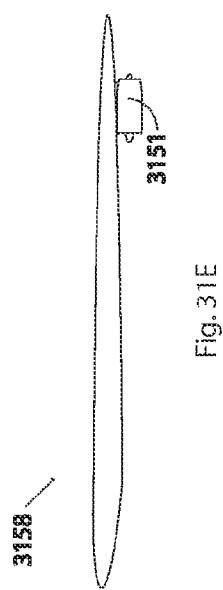

ROTARY UNITS, ROTARY MECHANISMS, AND RELATED APPLICATIONS

CROSS-REFERENCE TO RELATED APPLICATIONS

This application is a continuation of, and claims the benefit of priority from, U.S. Non-Provisional patent application Ser. No. 13/832,575, filed Mar. 15, 2013, which is a continuation-in-part of, and claims the benefit of priority from, U.S. Non-Provisional patent application Ser. No. 13/423,413, filed Mar. 19, 2012 (now U.S. Pat. No. 8,672,799, issued Mar. 18, 2014), which is a continuation-in-part of, and claims the benefit of priority from U.S. Non-Provisional patent application Ser. No. 13/219,683, filed Aug. 28, 2011 (now U.S. Pat. No. 8,715,133, issued May 6, 2014), which is a continuation-in-part of, and claims the benefit of priority from U.S. Non-Provisional patent application Ser. No. 13/184,332, filed Jul. 15, 2011 (now U.S. Pat. No. 8,668,618, issued Mar. 11, 2014), which is a continuation-in-part of, and claims the benefit of priority from U.S. Provisional Patent Application Nos. 61/365,290, filed Jul. 16, 2010 and 61/376,725, filed Aug. 25, 2010, which are each incorporated by reference in their entirety. U.S. Non-Provisional patent application Ser. No. 13/184,332, filed Jul. 15, 2011 (now U.S. Pat. No. 8,668,618, issued Mar. 11, 2014) is also continuation-in-part of, and claims the benefit of priority from, U.S. Non-Provisional patent application Ser. No. 12/577,326, filed Oct. 12, 2009 (now U.S. Pat. No. 8,152,679, issued Apr. 10, 2012), which claims the benefit of priority from U.S. Provisional Patent Application No. 61/104,748, filed on Oct. 12, 2008 and is a continuation of, and claims the benefit of International Patent Application No. PCT/US09/60386, filed on Oct. 12, 2009, which are each incorporated by reference in their entirety. U.S. Non-Provisional patent application Ser. No. 13/832,575, filed Mar. 15, 2013, also claims the benefit of priority from U.S. Provisional Patent Application Nos. 61/646,348, filed May 13, 2012 and 61/640,530, filed Apr. 30, 2012, which are each incorporated by reference in their entirety.

FIELD OF THE INVENTION

The invention relates generally to mechanical, electrical, or electromechanical devices, and provides rotary units, rotary mechanisms, methods, and related devices and other applications that are useful for a wide variety of purposes, including as engines.

BACKGROUND OF THE INVENTION

Jet engines are reaction engines that discharge fast moving jets which generate thrust by jet propulsion in accordance with Newton's laws of motion. In these propulsion systems, fluid enters the system at speed $V_0$ with a mass flow of $dm/dt$ and exits at speed $V_e$. Mass is added to the outflow at a rate $dm_f/dt$. Examples of jet engines include turbojets, turbofans, rockets, ramjets, pulse jets, and propeller-driven systems.

Marine propulsion is the mechanism or system used to generate thrust to move a ship, a boat, or other marine vehicle across and/or through water. While paddles and sails are still used on some smaller boats, most modern ships and other marine vehicles are propelled by mechanical systems consisting a motor or engine turning a propeller, or in jet drives, an impeller. Steam engines were the first mechanical engines used in marine propulsion, but have mostly been replaced by two-stroke or four-stroke diesel engines, outboard motors, and gas turbine engines on faster ships. Nuclear reactors producing steam are used to propel warships and icebreakers, and there have been attempts to utilize them to power commercial vessels. Electric motors have been used on submarines and electric boats and have been proposed for energy-efficient propulsion. Recent development in liquified natural gas (LNG) fueled engines are gaining recognition for their low emissions and cost advantages.

SUMMARY OF THE INVENTION

In one aspect, the invention provides a rotary mechanism that includes at least first, second, and third rotational components, wherein at least one of the rotational components comprises at least a first implement selected from the group consisting of: a first propeller, a first impeller, a first fan assembly, a first fan, a first blade, a first compressor, a first booster, a first combustor, a first rotor, a first turbine, a first nozzle, a first duct, a first generator, a first motor, a first gear component, and a first component thereof. The rotary mechanism also includes at least first and second counter-rotational mechanisms, wherein the first counter-rotational mechanism operably engages at least the first and second rotational components, and wherein the second counter-rotational mechanism operably engages at least the second and third rotational components. In addition, the rotary mechanism also includes at least one drive mechanism component or a portion thereof that operably engages one or more of the rotational components and/or one or more of the counter-rotational mechanisms, which drive mechanism component or portion thereof is configured at least to effect rotation of the rotational components and the counter-rotational mechanisms such that the first and third rotational components rotate in a first direction and the second rotational component rotates in a second direction. In some embodiments, an engine includes the rotary mechanism. In certain embodiments, a ground vehicle, a marine vehicle, an aircraft, or a device includes (e.g., is operably connected to) the rotary mechanism. In certain embodiments, boat (e.g., a power boat, a yacht, a sail boat, or the like), a ship, canoe, kayak, hydrofoil, submarine, submersible, a hand-held marine propulsion device (e.g., a diving propulsion device, etc.), a surf board, a wind surfing board, a boogie board, a paddle board, a personal watercraft, a water ski, a wake board, or the like includes (e.g., is operably connected to) the rotary mechanism.

In some embodiments, each rotational component comprises one or more implements. In certain embodiments, the rotary mechanism includes more than three rotational components and/or more than two counter-rotational mechanisms. In some embodiments, at least one of the rotational components is configured to rotate at least partially around a rotational axis and comprises at least one surface that is configured to rotate substantially non-perpendicular the rotational axis, which surface comprises the first implement. In certain embodiments, the rotational components are configured to rotate substantially non-concentrically relative to one another.

In certain embodiments, the drive mechanism component or portion thereof comprises at least one shaft component that operably engages one or more of the rotational components and/or one or more of the counter-rotational mechanisms. In some embodiments, the drive mechanism component or portion thereof comprises at least one gear component.

In some embodiments, the first implement rotates at least proximal to at least a second implement selected from the group consisting of: a second propeller, a second impeller, a second fan assembly, a second fan, a second blade, a second compressor, a second booster, a second combustor, a second rotor, a second turbine, a second nozzle, a second duct, a second generator, a second motor, a second gear component, and a second component thereof. In some embodiments, the first implement operably engages the second implement. In certain embodiments, at least one other component comprises the second implement. In some of these embodiments, for example, the other component comprises at least one propulsion unit.

In another aspect, the invention provides a rotary mechanism that includes at least first and second rotational components and at least a first counter-rotational mechanism that operably engages at least the first and second rotational components, wherein the first and second rotational components are configured to rotate substantially non-concentrically relative to one another at least partially around a rotational axis, and wherein at least one surface of the first and/or second rotational component comprises at least a first implement selected from the group consisting of: a first propeller, a first impeller, a first fan assembly, a first fan, a first blade, a first compressor, a first booster, a first combustor, a first rotor, a first turbine, a first nozzle, a first duct, a first generator, a first motor, a first gear component, and a first component thereof. The rotary mechanism also includes at least one drive mechanism component or portion thereof that operably engages one or more of the rotational components and/or the first counter-rotational mechanism such that when the first rotational component rotates in a first direction, the second rotational component rotates in a second direction, and the first implement rotates at least proximal to at least a second implement selected from the group consisting of: a second propeller, a second impeller, a second fan assembly, a second fan, a second blade, a second compressor, a second booster, a second combustor, a second rotor, a second turbine, a second nozzle, a second duct, a second generator, a second motor, a second gear component, and a second component thereof. In some embodiments, an engine includes the rotary mechanism. In certain embodiments, a ground vehicle, a marine vehicle, an aircraft, or a device includes (e.g., is operably connected to) the rotary mechanism.

In some embodiments, the surfaces of the first and second rotational components that comprise the first implement are configured to rotate substantially non-concentrically relative to one another at least partially around the rotational axis. In some embodiments, the first rotational component comprises the first implement and the second rotational component comprises the second implement. In certain embodiments, when the first rotational component rotates in the first direction and the second rotational component rotates in the second direction, the first implement operably engages the second implement. In some embodiments, the rotary mechanism includes more than two rotational components and/or more than one counter-rotational mechanism. In some embodiments, at least one of the rotational components is configured to rotate at least partially around a rotational axis and comprises at least one surface that is configured to rotate substantially non-perpendicular to the rotational axis, which surface comprises the implement. In some embodiments, the rotational components are configured to rotate substantially non-concentrically relative to one another.

In certain embodiments, at least one other component comprises the second implement. In some of these embodiments, the other component comprises at least one propulsion unit.

In some embodiments, rotary mechanisms include at least two rotary units that each comprises: at least one rotational component that comprises at least one sun gear component and at least one ring gear component, and at least one gear structure that comprises at least one support component and at least one planetary gear component rotatably coupled to the support component, and wherein the planetary gear component is configured to operably engage the ring gear component, wherein the sun gear component of at least a first rotary unit operably engages the planetary gear component of at least a second rotary unit such that when the rotational component of the first rotary unit rotates in the first direction, the rotational component of the second rotary unit rotates in the second direction. In some of these embodiments, the gear structure of the first rotary unit is operably connected to the gear structure of the second rotary unit such that the support components are substantially fixedly positioned relative to one another at least when the rotational component of the first rotary unit rotates in the first direction, the rotational component of the second rotary unit rotates in the second direction.

In certain embodiments, rotary mechanisms include at least a first rotary unit that comprises at least one rotational component that comprises at least first and second sun gear components, at least a second rotary unit that comprises at least one rotational component that comprises at least first and second ring gear components, and at least a first planetary gear component that is configured to operably engage the second sun gear component of the first rotary unit and the first ring gear component of the second rotary unit such that when the rotational component of the first rotary unit rotates in the first direction, the rotational component of the second rotary unit rotates in the second direction. In some of these embodiments, rotary mechanisms include at least one gear structure that comprises at least one support component, wherein the first planetary gear component is rotatably coupled to the support component, which support component is substantially fixedly positioned when the rotational component of the first rotary unit rotates in the first direction, the rotational component of the second rotary unit rotates in the second direction.

In some embodiments, rotary mechanisms include at least two rotary units that each comprises: at least one rotational component that comprises at least one ring gear component, and at least one second gear component configured to operably engage the ring gear component. In some of these embodiments, rotary mechanisms include one or more alignment components that align at least the rotational components relative to one another when the rotational components rotate. In some of these embodiments, the drive mechanism component or portion thereof operably engages at least the second gear components of at least first and second rotary units, which drive mechanism component or portion thereof is configured to effect rotation of the second gear components such that the rotational component of the first rotary unit rotates in a first direction and the rotational component of the second rotary unit rotates in a second direction. In certain of these embodiments, the drive mechanism component or portion thereof comprises at least two shaft components, wherein at least a first shaft component operably engages at least the second gear component of the first rotary unit and at least a second shaft component operably engages at least the second gear component of the second rotary unit. In some of these embodiments, the first and second shaft components each comprises at least one drive gear component that operably engage one another.

In certain embodiments, rotary mechanisms include at least two rotational components that each comprises at least one ring gear component, and at least one counter-rotational mechanism that comprises at least a first gear component that operably engages the ring gear component of at least a first rotational component, at least a second gear component that operably engages the ring gear component of at least a second rotational component, and at least a third gear component that operably engages at least the second gear component such that when the first gear component rotates in the first direction, the first rotational component rotates in the first direction and the second gear component and the second rotational component rotate in the second direction. In some of these embodiments, rotary mechanisms include one or more alignment components that align at least the first and second rotational components relative to one another when the rotational components rotate. In some of these embodiments, the drive mechanism component or portion thereof operably engages at least the first gear component, which drive mechanism component or portion thereof is configured to effect rotation of at least the first gear component. In some of these embodiments, the drive mechanism component or portion thereof operably engages the third gear component. In some of these embodiments, the drive mechanism component or portion thereof comprises at least one shaft component that operably engages at least the first gear component.

In some embodiments, rotary mechanisms include at least a first rotary unit that comprises at least one rotational component that comprises at least two ring gear components and at least a second rotary unit that comprises at least one rotational component that comprises at least two ring gear components. In these embodiments, rotary mechanisms also typically include at least a first planetary gear component that is configured to operably engage at least one of the ring gear components of the first rotary unit and at least one of the ring gear components of the second rotary unit such that when the rotational component of the first rotary unit rotates in the first direction, the rotational component of the second rotary unit rotates in the second direction. In some of these embodiments, rotary mechanisms include at least one gear structure that comprises at least one support component, wherein the first planetary gear component is rotatably coupled to the support component, which support component is substantially fixedly positioned when the rotational component of the first rotary unit rotates in the first direction, the rotational component of the second rotary unit rotates in the second direction.

In another aspect, the invention provides an engine that includes at least one rotary mechanism that comprises at least first and second rotational components and at least a first counter-rotational mechanism that operably engages at least the first and second rotational components, wherein the first and second rotational components are configured to rotate substantially non-concentrically relative to one another around a first rotational axis, and wherein the first and/or second rotational component comprises at least a first gear component. The engine also include at least one propulsion mechanism that comprises at least a first propulsion unit that is configured to rotate around a second rotational axis, wherein the first propulsion unit comprises at least a second gear component that operably engages the first gear component, and wherein the first propulsion unit comprises at least one implement selected from the group consisting of: a propeller, an impeller, a fan assembly, a fan, a blade, a compressor, a booster, a combustor, a rotor, a turbine, a nozzle, a duct, a generator, a motor, a gear component, and a component thereof. In addition, the engine also includes at least one drive mechanism component or portion thereof that operably engages one or more of the rotational components, the first counter-rotational mechanism, and/or the propulsion mechanism such that when the first rotational component rotates in a first direction, the second rotational component rotates in a second direction, and the first propulsion unit rotates in the first and/or second direction. In some embodiments, a ground vehicle, a marine vehicle, an aircraft, a device, or the like includes the engine.

In some embodiments, the first and second rotational axes are positioned substantially parallel to one another. In certain embodiments, the first and/or second rotational component comprises at least one exterior surface that comprises the first gear component. In some embodiments, the drive mechanism component or portion thereof comprises at least one gear component that operably engages at least one gear component of at least one propulsion unit. In certain embodiments, the engine includes at least one motor and/or generator that operably engage the rotary mechanism, the propulsion mechanism, and/or the drive mechanism component or portion thereof.

In some embodiments, the first propulsion unit comprises at least one interior surface and at least one exterior surface, wherein the interior surface comprises at least a portion of the implement and wherein the exterior surface comprises the second gear component. In some embodiments, the propulsion mechanism comprises at least one shaft component. In certain embodiments, the propulsion mechanism comprises two or more propulsion units, wherein neighboring pairs of propulsion units are configured to rotate in substantially opposite directions relative to one another around the second rotational axis. In some embodiments, the propulsion mechanism comprises two or more propulsion units that comprise different implements or portions thereof. In certain embodiments, the propulsion mechanism comprises two or more propulsion units that each comprises at least a portion of the implement. In some embodiments, the propulsion mechanism comprises at least one compressor, at least one combustor, and at least one turbine.

In another aspect, the invention provides an engine that includes at least one rotary mechanism that comprises at least first and second rotational components and at least a first counter-rotational mechanism that operably engages at least the first and second rotational components, wherein the first and second rotational components are configured to rotate substantially non-concentrically relative to one another around a first rotational axis, and wherein one or more of the rotational components comprise at least one compressor, at least one turbine, and/or at least a portion thereof. The engine also includes at least one drive mechanism component or portion thereof that operably engages one or more of the rotational components and/or the first counter-rotational mechanism such that when the first rotational component rotates in a first direction, the second rotational component rotates in a second direction. In addition, the engine also includes at least one combustor in communication with the compressor and/or the turbine.

In certain embodiments, the engine includes at least one nacelle component that contains at least a portion of the rotary mechanism, the drive mechanism component or portion thereof, and/or the combustor. In some embodiments, one or more of the rotational components comprise the combustor or a portion thereof. In certain embodiments, the engine includes a propeller, an impeller, a fan assembly, a fan, a blade, a rotor, a booster, a nozzle, a duct, a generator, a motor, a gear component, and/or a component thereof. In some embodiments, one or more of the rotational components comprise a propeller, an impeller, a fan assembly, a fan, a blade, a booster, a nozzle, a duct, a generator, a motor, a gear component, and/or a component thereof.

In another aspect, the invention provides a rotary unit that includes at least a first rotational component that comprises at least one surface that comprises at least a first implement selected from the group consisting of: a first propeller, a first impeller, a first fan assembly, a first fan, a first blade, a first compressor, a first booster, a first combustor, a first rotor, a first turbine, a first nozzle, a first duct, a first generator, a first motor, a first gear component, and a first component thereof, and at least a second gear component that is configured to operably engage one or more other gear components of at least second and third rotational components when the first rotational component is disposed proximal to the second and third rotational components such that when the first rotational component rotates in a first direction, the second and third rotational components rotate in a second direction. In some embodiments, the surface of the first rotational component that comprises the first implement is configured to rotate substantially non-concentrically relative to the second and/or third rotational component. In some embodiments, a rotary mechanism includes the rotary unit. In certain embodiments, an engine includes the rotary unit. In some embodiments, a ground vehicle, a marine vehicle, an aircraft, a device, or the like includes the rotary mechanism.

In another aspect, the invention provides a method of assembling a rotary mechanism. The method includes placing at least a first counter-rotational mechanism into operable engagement with at least first and second rotational components, wherein the first and second rotational components are configured to rotate substantially non-concentrically relative to one another around a rotational axis, and wherein at least one surface of the first and/or second rotational component comprises at least a first implement selected from the group consisting of: a first propeller, a first impeller, a first fan assembly, a first fan, a first blade, a first compressor, a first booster, a first combustor, a first rotor, a first turbine, a first nozzle, a first duct, a first generator, a first motor, a first gear component, and a first component thereof. The method also includes placing at least one drive mechanism component or portion thereof into operable engagement with one or more of the rotational components and/or the first counter-rotational mechanism such that when the first rotational component rotates in a first direction, the second rotational component rotates in a second direction, and the first implement rotates at least proximal to at least a second implement selected from the group consisting of: a second propeller, a second impeller, a second fan assembly, a second fan, a second blade, a second compressor, a second booster, a second combustor, a second rotor, a second turbine, a second nozzle, a second duct, a second generator, a second motor, a second gear component, and a second component thereof, thereby assembling the rotary mechanism. In some embodiments, the method includes placing at least one other component into operable engagement with one or more of the rotational components, which other component comprises the second implement. In some of these embodiments, the other component comprises at least one propulsion unit.

In another aspect, the invention provides a method of rotating rotational components. The method includes (a) providing at least one rotary mechanism that comprises: at least first, second, and third rotational components, wherein at least one of the rotational components comprises at least one implement selected from the group consisting of: a propeller, an impeller, a fan assembly, a fan, a blade, a compressor, a booster, a combustor, a rotor, a turbine, a nozzle, a duct, a generator, a motor, a gear component, and a component thereof, and at least first and second counter-rotational mechanisms, wherein the first counter-rotational mechanism operably engages at least the first and second rotational components, and wherein the second counter-rotational mechanism operably engages at least the second and third rotational components. The method also includes (b) rotating the rotational components and the counter-rotational mechanisms such that the first and third rotational components rotate in a first direction and the second rotational component rotates in a second direction, thereby rotating rotational components. In some embodiments, the rotary mechanism comprises at least one drive mechanism component or a portion thereof that operably engages one or more of the rotational components and/or one or more of the counter-rotational mechanisms, and (b) comprises using the drive mechanism component or portion thereof to effect rotation of the rotational components and the counter-rotational mechanisms. In certain embodiments, one or more of the rotational components comprises at least one gear component that operably engages at least one gear component of at least one propulsion component and (b) comprises rotating the propulsion component.

BRIEF DESCRIPTION OF THE DRAWINGS

The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 1A schematically illustrates a rotational component of a rotary unit from a front side view according to one embodiment of the invention. FIG. 1B schematically shows a sectional view of the rotational component of FIG. 1A. FIG. 1C schematically depicts the rotational component of FIG. 1A from a side view. FIG. 1D schematically shows a gear component used in the rotary unit referred to with respect to FIG. 1A from a front side view. FIG. 1E schematically illustrates the gear component of FIG. 1D from a side view.

FIG. 2A schematically illustrates a rotary unit from a front side view according to one embodiment of the invention. FIG. 2B schematically depicts the rotary unit of FIG. 2A from a side view. FIG. 2C schematically shows the rotary unit of FIG. 2A from a rear side view. FIG. 2D schematically shows a sectional view of the gear structure of FIG. 2A.

FIG. 3A schematically illustrates a rotary unit from a front side view according to one embodiment of the invention. FIG. 3B schematically shows the rotary unit of FIG. 3A from a rear side view. FIG. 3C schematically depicts the rotary unit of FIG. 3A from a side view. FIG. 3D schematically shows schematically shows a sectional view of the rotary unit of FIG. 3A.

FIG. 4A schematically illustrates a rotary unit from a front side view according to one embodiment of the invention. FIG. 4B schematically shows the rotary unit of FIG. 4A from a rear side view. FIG. 4C schematically depicts the rotary unit of FIG. 4A from a side view. FIG. 4D schematically shows schematically shows a sectional view of the rotary unit of FIG. 4A. FIG. 4E schematically illustrates a planetary gear component from a front side view according to one embodiment of the invention. FIG. 4F schematically illustrates the planetary gear component of FIG. 4E from a side view. FIG. 4G schematically shows an exploded side view of a gear structure according to one embodiment of the invention. FIG. 4H schematically depicts the gear structure of FIG. 4G from a side view. FIG. 4I schematically shows the gear structure of FIG. 4H from a rear side view. FIG. 4J schematically shows the gear structure of FIG. 4H from a front side view. FIG. 4K schematically illustrates a gear structure prior to assembly with another gear structure from a side view according to one embodiment of the invention. FIG. 4L schematically shows an assembly that includes two gear structures from a side view according to one embodiment of the invention. FIG. 4M schematically shows an exploded view of the rotary unit of FIG. 4A with the gear structure of FIG. 4G from a side view according to one embodiment of the invention. FIG. 4N schematically shows the rotary unit of FIG. 4A with the gear structure of FIG. 4G from a front side view. FIG. 4O schematically shows the rotary unit of FIG. 4A with the gear structure of FIG. 4G from a rear side view. FIG. 4P schematically shows the rotary unit of FIG. 4A with the gear structure of FIG. 4G from a side view. FIG. 4Q schematically shows a sectional view of the rotary unit of FIG. 4A with the gear structure of FIG. 4G.

FIGS. 5 A-G schematically illustrate rotary units or components thereof from various views according to one exemplary embodiment of the invention. FIG. 5A schematically shows a rotational component from a front side view according to one embodiment of the invention. FIG. 5B schematically shows the rotational component from FIG. 5A from a side sectional view. FIG. 5C schematically depicts the rotational component from FIG. 5A from a side view. FIG. 5D schematically depicts the rotational component from FIG. 5A from a side view with a surface including implements.

FIG. 6D schematically shows the portion of the rotary mechanism of FIG. 6B from a sectional view. FIG. 6E schematically depicts the positioning component of FIG. 6A from a side view. FIG. 6F schematically shows the positioning component of FIG. 6A with a drive mechanism from a side view. FIG. 6G schematically illustrates a positioning component of a rotary mechanism from a side view according to one embodiment of the invention. FIG. 6H schematically illustrates a rotary mechanism that includes the rotational component of FIG. 1A from a side view according to one embodiment of the invention. FIG. 6I schematically shows the rotary mechanism of FIG. 6H from a sectional view. FIG. 6J schematically shows the rotary mechanism of FIG. 6H from a front side view. FIG. 6K schematically shows the rotary mechanism of FIG. 6H from a rear side view. FIG. 6L schematically depicts a portion of a drive mechanism from a side view according to one embodiment of the invention. FIG. 6M schematically depicts a portion of a drive mechanism from a side view according to one embodiment of the invention. FIG. 6N schematically depicts the portion of the drive mechanism of FIG. 6M without a motor from a side view. FIG. 6O schematically depicts the portion of the drive mechanism of FIG. 6M from a side view.

FIG. 7A schematically illustrates a rotary mechanism that includes the rotary unit of FIG. 2A from a sectional view prior to assembly according to one embodiment of the invention. FIG. 7B schematically depicts the rotary mechanism of FIG. 7A from a sectional view following assembly. FIG. 7C schematically shows the rotary of FIG. 7A from a side view. FIG. 7D schematically illustrates a rotary mechanism that includes the rotary unit of FIG. 2A from a side view according to one embodiment of the invention. FIG. 7E schematically illustrates a rotary mechanism that includes the rotary unit of FIG. 2A from a side view according to one embodiment of the invention.

FIG. 8A schematically illustrates a gear structure from the rotary unit of FIG. 2A prior to assembly with another gear structure from a side view according to one embodiment of the invention. FIG. 8B schematically shows an assembly of multiple gear structures from a side view according to one embodiment of the invention. FIG. 8C schematically depicts the gear structure assembly of FIG. 8B from a rear side view. FIG. 8D schematically depicts the gear structure assembly of FIG. 8B from a front side view. FIG. 8E schematically shows a rotary mechanism that includes the gear structure assembly of FIG. 8B from a sectional view according to one embodiment of the invention. FIG. 8F schematically shows a rotary mechanism that includes the gear structure assembly of FIG. 8B from a side view according to one embodiment of the invention.

FIG. 9A schematically depicts a rotational mechanism from an exploded side view according to one embodiment of the invention. FIG. 9B schematically depicts the rotational mechanism from FIG. 9A from a side view. FIG. 9C schematically depicts the rotational mechanism from FIG. 9A from an exploded sectional view. FIG. 9D schematically depicts the rotational mechanism from FIG. 9A from a sectional side view. FIG. 9E schematically shows a portion of a drive mechanism component from a front side view according to one embodiment of the invention. FIG. 9F schematically shows the portion of the drive mechanism component of FIG. 9E from a rear side view. FIG. 9G schematically shows the portion of the drive mechanism component of FIG. 9E from a side view. FIG. 9H schematically shows the portion of the drive mechanism component of FIG. 9E from a sectional side view. FIG. 9I schematically shows an exploded side view of a gear structure according to one embodiment of the invention. FIG. 9L schematically depicts the gear structure from FIG. 9I from a rear side view. FIG. 9K schematically depicts the gear structure from FIG. 9I from a side view. FIG. 9L schematically depicts the gear structure from FIG. 9I from a front side view. FIG. 9M schematically shows an exploded side view of the drive mechanism component of FIG. 9E and the gear structure of FIG. 9I according to one embodiment of the invention. FIG. 9N schematically shows an exploded sectional side view of the drive mechanism component of FIG. 9E and the gear structure of FIG. 9I according to one embodiment of the invention. FIG. 9O schematically depicts the drive mechanism component of FIG. 9E and the gear structure of FIG. 9I from a side view. FIG. 9P schematically depicts the drive mechanism component of FIG. 9E and the gear structure of FIG. 9I from sectional side view. FIG. 9O schematically depicts an exploded side view of the rotational mechanism from FIG. 9B and the portion of the drive mechanism component of FIG. 9E according to one embodiment of the invention. FIG. 9R schematically depicts an exploded side sectional view of the rotational mechanism from FIG. 9B and the portion of the drive mechanism component of FIG. 9E according to one embodiment of the invention.

FIG. 10A schematically shows a rotary mechanism from a front side view according to one embodiment of the invention. FIG. 10B schematically shows rotational components positioned relative to one another from a cross-sectional view according to one embodiment of the invention. FIG. 10C schematically illustrates gear components of a counter-rotational mechanism operably engaging a drive mechanism component from a side view according to one embodiment of the invention. FIG. 10D schematically illustrates gear components of a counter-rotational mechanism operably engaging a drive mechanism component from a side view according to one embodiment of the invention. FIG. 10E schematically shows the gear and drive mechanism components from FIGS. 10C and D positioned relative to one another from a side view. FIG. 10F schematically shows the rotary mechanism from FIG. 10A from a side view. FIG. 10G schematically depicts the rotary mechanism from FIG. 10A from a side sectional view. FIG. 10H schematically depicts the rotary mechanism from FIG. 10G from a side sectional view with an exemplary motor. FIG. 10I schematically shows the rotary mechanism from FIG. 10H from a side view with rotational components including implements.

FIGS. 11A-C schematically illustrate a rotary mechanism or components thereof from various views according to one exemplary embodiment of the invention. FIG. 11A schematically shows portions of a rotational component prior to assembly from a side view. FIG. 11B schematically depicts a rotary mechanism that includes the rotational component from FIG. 11A prior to assembly from a front side view. FIG. 11C schematically depicts the rotary mechanism from FIG. 11B from a side view.

FIGS. 12A and B schematically show gear and drive mechanism components prior to and following assembly, respectively, according to one exemplary embodiment of the invention.

FIGS. 13A and B schematically show gear and drive mechanism components prior to and following assembly, respectively, according to one exemplary embodiment of the invention.

FIG. 14A schematically shows a detailed front side view of a shaft receiving area according to one embodiment of the invention.

FIG. 14B schematically shows a detailed front side view of a drive mechanism portion configured to be received by the one drive mechanism component area from FIG. 14A according to one embodiment of the invention.

FIG. 15 schematically shows a rotary mechanism prior to assembly from a side view according to one embodiment of the invention.

FIGS. 16A-F schematically show a rotary mechanism or components thereof from various views according to one exemplary embodiment of the invention. FIG. 16A schematically illustrates gear and drive mechanism components of a rotary mechanism prior to assembly from a side view. FIG. 16B schematically illustrates gear and drive mechanism components of a rotary mechanism from a side view. FIG. 16C schematically illustrates the gear and drive mechanism components from FIG. 16B positioned relative to rotational components from a sectional side view. FIG. 16D schematically shows the rotary mechanism from FIG. 16C from a front side view. FIG. 16E schematically shows the rotary mechanism from FIG. 16C from a side view. FIG. 16F schematically shows a drive mechanism positioning component from a front side view according to one exemplary embodiment of the invention.

FIG. 17A schematically illustrates an exploded view of a propulsion device according to one embodiment of the invention. FIG. 17B schematically shows the propulsion device of FIG. 17A from a partially exploded view. FIG. 17C schematically shows the propulsion device of FIG. 17A from a partially exploded view. FIG. 17D schematically illustrates the propulsion device of FIG. 17A from a side view. FIG. 17E schematically shows the propulsion device of FIG. 17A from a front side view. FIG. 17F schematically shows the propulsion device of FIG. 17A from a rear side view.

FIG. 18A schematically illustrates the propulsion device of FIG. 17A disposed within a housing from a front side view according to one embodiment of the invention. FIG. 18B schematically illustrates the propulsion device of FIG. 17A disposed within a housing from a rear side view according to one embodiment of the invention. FIG. 18C schematically illustrates the propulsion device of FIG. 17A disposed within a housing from a side view according to one embodiment of the invention. FIG. 18D schematically illustrates the propulsion device of FIG. 17A disposed within a housing from a partially sectional front side view according to one embodiment of the invention. FIG. 18E schematically illustrates the propulsion device of FIG. 17A disposed within a housing from a partially sectional side view according to one embodiment of the invention.

FIG. 19A schematically shows a propulsion device including rotary mechanisms from a partially exploded view according to one embodiment of the invention. FIG. 19B schematically illustrates the propulsion device of FIG. 19A from a side view. FIG. 19C schematically shows the propulsion device of FIG. 19A from a front side view. FIG. 19D schematically shows the propulsion device of FIG. 19A from a rear side view.

FIG. 20A schematically shows a boat that includes propulsion devices from a side view according to one embodiment of the invention. FIG. 20B schematically illustrates the boat of FIG. 20A from a front side view.

FIG. 21A schematically shows an aircraft that includes propulsion devices from a front side view according to one embodiment of the invention. FIG. 21B schematically illustrates the aircraft of FIG. 21A from a side view.

FIG. 25 schematically illustrates a portion of an engine from a cross-sectional side view according to one embodiment of the invention.

FIG. 26A schematically illustrates a rotational component of a rotary unit from a front side view according to one embodiment of the invention. FIG. 26B schematically depicts the rotational component of FIG. 26A from a side view. FIG. 26C schematically shows a sectional view of the rotational component of FIG. 26A. FIG. 26D schematically depicts a gear structure from a side view according to one embodiment of the invention. FIG. 26E schematically illustrates the gear structure of FIG. 26D from a top view. FIG. 26F schematically illustrates a gear structure prior to assembly with another gear structure from a side view according to one embodiment of the invention. FIG. 26G schematically shows an assembly that includes four gear structures from a side view according to one embodiment of the invention.

FIG. 27A schematically illustrates a rotary mechanism that includes the rotational component of FIG. 26A and a drive mechanism component from a sectional view prior to assembly according to one embodiment of the invention. FIG. 27B schematically depicts the rotary mechanism of FIG. 27A from a sectional view following assembly.

FIG. 29A schematically illustrates a portion of an engine from a cross-sectional side view according to one embodiment of the invention. FIG. 29B schematically shows the engine of FIG. 29A with a cover housing from a side view.

FIG. 30A schematically illustrates a portion of an engine from a sectional view with an drive motor prior to assembly according to one embodiment of the invention. FIG. 30B schematically depicts the engine and drive motor of FIG. 30A from a sectional view following assembly. FIG. 30C schematically shows the engine of FIG. 30B with a cover housing from a side view.

FIG. 31A schematically illustrates a kayak that includes an engine from a side view according to one embodiment of the invention. FIG. 31B schematically illustrates a submersible that includes engines from a side view according to one embodiment of the invention. FIG. 31C schematically illustrates a hand-held marine propulsion device that includes engines from a side view according to one embodiment of the invention. FIG. 1D schematically illustrates a boogie board that includes engines from a side view according to one embodiment of the invention. FIG. 31E schematically illustrates a paddle board that includes engines from a side view according to one embodiment of the invention. FIG. 31F schematically illustrates a personal watercraft that includes engines from a side view according to one embodiment of the invention.

DETAILED DESCRIPTION

I. Introduction

Figure 5E:
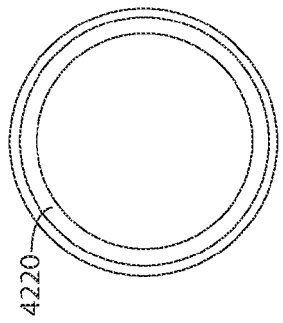
FIG. 5E schematically shows the rotational component from FIG. 5D from a front side view.

Before describing the invention in detail, it is to be understood that this invention is not limited to particular methods, rotary units, rotary mechanisms, devices, or systems, which can vary. As used in this specification and the appended claims, the singular forms "a," "an," and "the" also include plural referents unless the context clearly provides otherwise. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the invention, the following terminology, and grammatical variants thereof, will be used in accordance with the definitions set forth below.

The term "coaxially positioned" refers to objects that are positioned relative to one another such that they can rotate about a substantially coincident axis.

The term "fixed position" refers to objects that are positioned relative to one another such that they do not move separately from one another. In some embodiments, for example, gear components (e.g., sun gear components) are attached (e.g., integrally fabricated, bonded, welded, adhered, or the like) to rotational components, such that when the rotational components move in one direction, the gear components move in the same direction as the rotational components.

The term "counter-rotate" or "contra-rotate" refers to objects that rotate in opposite directions relative to one another. In some embodiments, for example, rotary mechanisms include rotational components that are configured to rotate in opposite directions.

The term "communicate" refers to the direct or indirect transfer or transmission, and/or capability of directly or indirectly transferring or transmitting, something at least from one thing to another thing. In some embodiments, for example, devices include housings having openings through which hair, finger nails, or the like can be transferred to contact implements within housing cavities of the devices.

The invention relates to rotary units and rotary mechanisms that are suitable for use in numerous applications, including as components of various types of engines. Rotary units typically include rotational components that are configured to rotate. In some embodiments, for example, multiple rotary units are assembled in rotary mechanisms such that neighboring pairs of rotational components counter-rotate or contra-rotate relative to one another during operation of the rotary mechanisms. Rotational components generally include one or more implements that are structured to perform or effect one or more types of work as the rotational components rotate relative to one another in a given rotary mechanism. In certain embodiments, implements are configured to rotate and/or to effect the movement of other components as rotational components rotate. The representative embodiments described herein are intended to illustrate, but not to limit, the invention. Essentially any combination of components or portions thereof described herein are optionally utilized or adapted for use together in certain embodiments.

II. Exemplary Rotary Units

FIGS. 1A-E schematically show components of a rotary unit according to one exemplary embodiment of the invention. As shown, the rotary unit includes rotational component 1302 and gear component 1304 (e.g., a planetary gear component or the like). Although not shown, rotational component 1302 typically includes one or more implements (e.g., gear components, propellers, fan assemblies, fans, blades, compressors, boosters, combustors, turbines, nozzles, ducts, generators, motors, components thereof, etc.). Rotational component 1302 includes gear component 1310 (e.g., a sun gear component, etc.) that is configured to operably engage or mesh with gear component 1304. Rotational mechanisms that include these components are described further herein.

FIGS. 2A-D schematically show a rotary unit or components thereof according to an exemplary embodiment of the invention. As shown, rotary unit 1400 includes rotational component 1402 that includes gear component 1410 (e.g., a sun gear component, etc.), gear component 1412 (e.g., a ring gear component, etc.), and gear structure receiving area 1413. Gear component 1410 substantially fixedly extends from first surface 1406 of rotational component 1402. Gear component 1410 is configured to operably engage or mesh with one or more other gear components of another rotary unit when gear component 1410 is disposed proximal to the other gear components. Gear component 1412 substantially fixedly extends from second surface 1408 of rotational component 1402. Gear component 1412 communicates with gear structure receiving area 1413. Gear structure receiving area 1413 is configured to receive gear structure 1415.

Gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. Rotational component 1402 is configured to rotate relative to support component 1417, which support component 1417 is substantially fixedly positioned when rotational component 1402 rotates relative to support component 1417. Gear components 1414 are configured to rotate relative to rotational component 1402. Gear structures that include support components 1417 are described further herein. Although not shown, rotary unit 1400 also typically includes one or more implements (e.g., gear components, propellers, fan assemblies, fans, blades, compressors, boosters, combustors, turbines, nozzles, ducts, generators, motors, components thereof, etc.). Exemplary implements are described further herein. Rotational mechanisms typically include one or more rotary units 1400. Exemplary rotational mechanisms are described further herein.

FIGS. 3A-D schematically illustrate a rotary unit according to one embodiment of the invention. As shown, rotary unit 1500 includes rotational component 1502 that includes first sun gear component 1504 and second sun gear component 1506 on first and second surfaces, respectively, of rotational component 1502, which substantially oppose one another. First sun gear component 1504 is configured to operably engage one or more gear components of at least a second rotational component (not shown) when rotational component 1502 is disposed proximal to the second rotational component such that when rotational component 1502 rotates in a first direction, the second rotational component rotates in a second direction. Second sun gear component 1506 is configured to operably engage one or more gear components of at least a third rotational component (not shown) when rotational component 1502 is disposed proximal to the third rotational component such that when rotational component 1502 rotates in the first direction, the third rotational component rotates in the second direction. Exemplary gears that are optionally adapted for use with the rotary units, rotational mechanisms, and related applications of the invention are also described in, e.g., Dudley, Handbook of Practical Gear Design (Mechanical Engineering Series), CRC Press, 1st Ed. (1994) and Litvin and Fuentes, Gear Geometry and Applied Theory, Cambridge University Press; 2nd Ed. (2004), which are both incorporated herein in their entirety for all purposes.

Rotary unit 1500 also includes hole 1508 disposed through rotational component 1502. Hole 1508 is configured to receive, e.g., a drive mechanism component (e.g., an axle, a shaft, a gear structure component, etc.) or a support component such that rotational component 1502 can rotate around the drive mechanism component, the support component, or the like. Rotational component 1502 also includes friction reducing materials 1510 (shown as elevated or pointed surface features) to reduce friction as rotational component 1502 rotates relative to, e.g., other rotational component. In addition, rotational component 1502 also include implements 1512 on a surface of rotational component 1502 that is configured to rotate substantially non-perpendicular to a rotational axis of rotary unit 1500. Essentially any implement (e.g., gear components, propellers, fan assemblies, fans, blades, compressors, boosters, combustors, turbines, nozzles, ducts, generators, motors, components thereof, etc.) is optionally adapted for use with rotary unit 1500, including the exemplary implements described herein. Rotary unit 1500 is typically included in a rotational mechanism, an engine, a device or the like. Exemplary rotational mechanisms that include rotary unit 1500 are described herein. In addition, representative devices that are optionally adapted to include rotary unit 1500 are also described herein.

FIGS. 4 A-Q schematically illustrate a rotary unit or components thereof according to one-embodiment of the invention. As shown, rotary unit 1600 includes rotational component 1602 that includes first ring gear component 1604 and second ring gear component 1606 on first and second surfaces, respectively, of rotational component 1602, which substantially oppose one another. First ring gear component 1604 is configured to operably engage one or more gear components of at least a second rotational component (not shown) when rotational component 1602 is disposed proximal to the second rotational component such that when rotational component 1602 rotates in a first direction, the second rotational component rotates in a second direction. Second ring gear component 1606 is configured to operably engage one or more gear components of at least a third rotational component (not shown) when rotational component 1602 is disposed proximal to the third rotational component such that when rotational component 1602 rotates in the first direction, the third rotational component rotates in the second direction.

Rotary unit 1600 also includes hole 1608 disposed through rotational component 1602. Hole 1608 is configured to receive, e.g., a drive mechanism component (e.g., an axle, a shaft, a gear structure component, etc.) or a support component such that rotational component 1602 can rotate around the drive mechanism component, the support component, or the like. Exemplary drive mechanism components and support components are described herein. Although not shown, rotational component 1602 optionally also includes friction reducing materials (e.g., elevated or pointed surface features, surface coatings, roller balls, etc.) to reduce friction as rotational component 1602 rotates relative to, e.g., other rotational component. In addition, rotational component 1602 also include implements 1510 on a surface of rotational component 1602 that is configured to rotate substantially non-perpendicular to a rotational axis of rotary unit 1600. Essentially any implement (e.g., gear components, propellers, fan assemblies, fans, blades, compressors, boosters, combustors, turbines, nozzles, ducts, generators, motors, components thereof, etc.) is optionally adapted for use with rotary unit 1600, including the exemplary implements described herein. Rotary unit 1600 is typically included in a rotational mechanism, a device or the like. Exemplary rotational mechanisms that include rotary unit 1600 are described herein. In addition, representative devices that are optionally adapted to include rotary unit 1600 are also described herein.

In some embodiments, rotary unit 1600 also includes gear structure 1612, which includes support component 1614 and first planetary gear components 1616 and second planetary gear components 1618 rotatably coupled to support component 1614. As shown, first planetary gear components 1616 are configured to operably engage or mesh with first ring gear component 1604, second planetary gear components 1618 are configured to operably engage or mesh with second ring gear component 1606, and rotational component 1602 is configured to rotate relative to support component 1614, which is substantially fixedly positioned (e.g., in an assembled rotational mechanism, device, etc.) when rotational component 1602 rotates relative to support component 1614. As also shown, for example, in FIGS. 4 A and B, respectively, first ring gear component 1604 at least partially defines first gear structure receiving area 1605 and second ring gear component 1606 at least partially defines second gear structure receiving area 1607. First gear structure receiving area 1605 and second gear structure receiving area 1607 are configured to receive first portion 1622 and second portion 1624, respectively, of support component 1614 of gear structure 1612. First portion 1622 and second portion 1624 of support component 1614 of gear structure 1612 are described, e.g., further below.

FIG. 4G schematically shows an exploded side view of gear structure 1612 according to one embodiment of the invention. As shown, threaded region 1620 of first portion 1622 of support component 1614 inserts into a threaded region receiving area (not within view in FIG. 4G) of second portion 1624 of support component 1614 during assembly of gear structure 1612. In addition, first planetary gear components 1616 are rotatably coupled to second portion 1624 of support component 1614 via pronged retaining elements 1626 and second planetary gear components 1618 are rotatably coupled to first portion 1622 of support component 1614 via pronged retaining elements 1628 during assembly of gear structure 1612. As also shown, first portion 1622 and second portion 1624 of support component 1614 include friction reducing materials 1630 (shown as elevated or pointed surface features), e.g., to minimize friction when rotational component 1602 rotates relative to support component 1614 during operation of assembled rotary unit 1600. To further illustrate, FIG. 4M schematically shows an exploded view of rotary unit 1600 with first portion 1622 and second portion 1624 of support component 1614 of gear structure 1612 prior to assembly with rotational component 1602.

To further illustrate, FIG. 4K schematically illustrates gear structure 1612 prior to assembly with another gear structure 1612 from a side view according to one embodiment of the invention. As shown, during assembly, threaded region 1632 of one support component 1614 is inserted into threaded region receiving area 1634 of another support component 1614 such that the assembled support components 1614 are substantially fixedly positioned relative to one another, e.g., when rotational components 1602 of rotary units 1600 rotate relative to support components 1614. Essentially any attachment technique is optionally utilized to attach support components 1614 of gear structures 1612 to one another or first portion 1622 and second portion 1624 of support component 1614 to one another. Some exemplary techniques include, for example, bonding, welding, adhering, or the like. In some embodiments, multiple support components 1614 are fabricated as single integral part (e.g., as a molded part or the like).

Figure 5F:
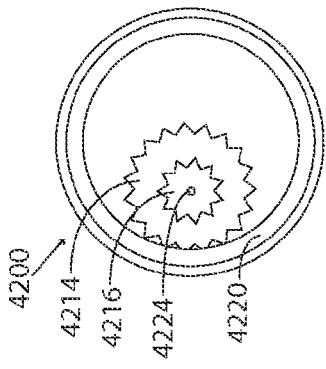
FIG. 5F schematically shows a rotary unit that includes the rotational component from FIG. 5A and first and third gear components from a front side view according to one exemplary embodiment of the invention.
Figure 5G:
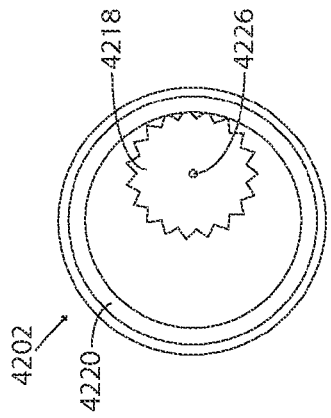
FIG. 5G schematically shows a rotary unit that includes the rotational component from FIG. 5A and a second gear component from a front side view according to one exemplary embodiment of the invention.

FIGS. 5 A-G schematically illustrate rotary units or components thereof from various views according to one exemplary embodiment of the invention. As shown, rotary unit 4200 or rotary unit 4202 each include rotational component 4204, which includes gear component 4206 (e.g., a ring gear component) and surface 4208 that includes implements (not shown). Rotational component 4204 is configured to rotate around rotational axis 4212. Surface 4208, which typically includes implements e.g., gear components, propellers, fan assemblies, fans, blades, compressors, boosters, combustors, turbines, nozzles, ducts, generators, motors, components thereof, etc.) is configured to rotate substantially non-perpendicular to rotational axis 4212. In some of these embodiments, surface 4208 is configured to rotate substantially parallel to rotational axis 4212 of rotational component 4204. Rotary unit 4200 includes first gear component 4214 and third gear component 4216. First gear component 4214 operably engages (e.g., meshes with) gear component 4206 such that when first gear component 4214 rotates in a first direction, rotational component 4204 rotates in the first direction. Rotary unit 4202 includes second gear component 4218 operably engages (e.g., meshes with) gear component 4206 of rotational component 4204. Second gear component 4218 operably engages (e.g., meshes with) third gear component 4216 when rotational component 4204 of rotary unit 4200 is disposed proximal to (e.g., operably engages) rotational component 4204 of rotary unit 4202 such that when first gear component 4214 rotates in the first direction, the rotational component 4204 of rotary unit 4200 rotates in the first direction and second gear component 4218 and rotational component 4204 of rotary unit 4202 rotate in a second direction.

Rotational component 4204 also includes alignment component 4220 and alignment component receiving area 4222. Alignment component 4220 and alignment component receiving area 4222 are configured to align rotational component 4204 relative to other rotational components when the other rotational components are disposed proximal to rotational component 4202. For example, alignment component 4220 of rotational component 4204 is configured to be received by an alignment component receiving area of another rotational component, while alignment component receiving area 4222 of rotational component 4204 is configured to receive an alignment component of another rotational component.

The drive mechanism components or portions thereof of the rotary units of the invention include various embodiments. Rotary unit 4200, for example, includes drive mechanism component or portion thereof 4224 (e.g., shown as a shaft component), which operably engages first gear component 4214 and at least one other gear component (i.e., third gear component 4216 in this embodiment). Drive mechanism component or portion thereof 4224 is configured to effect rotation of first gear component 4214 and third gear component 4216. To further illustrate, rotary unit 4202 includes drive mechanism component or portion thereof 4226 (e.g., shown as a shalt component), which operably engages second gear component 4218. Drive mechanism components or portions thereof, including drive mechanism component receiving areas are described further herein.

FIGS. 26A-E schematically show components of a rotary unit according to one exemplary embodiment of the invention. As shown, the rotary unit includes rotational component 2602 and gear structure 2604. Rotational component 2602 includes gear components 2606 (e.g., ring gear components, etc.). Although not shown, rotational component 2602 typically includes one or more implements (e.g., gear components, propellers, impellers, fan assemblies, fans, blades, compressors, boosters, combustors, turbines, nozzles, ducts, generators, motors, components thereof, etc.). Gear structure 2604 includes support component 2608 and gear components 2610 (e.g., planetary gear components or the like), which are rotatably coupled (see, directional arrows in FIG. 26D) to support component 2608. Gear components 2610 of gear structure 2604 are configured to operably engage or mesh with gear components 2606 (e.g., neighboring pairs of rotational components 2602). FIG. 26F schematically illustrates a gear structure prior to assembly with another gear structure from a side view according to one embodiment of the invention. During assembly, threaded region 2612 of one support component 2608 is inserted into a threaded region receiving area (not within view) of another support component 2608 such that the assembled support components 2608 are substantially fixedly positioned relative to one another when rotational components 2602 of the rotary units and gear components 2610 rotate relative to support components 2608 and to one another. Essentially any attachment technique is optionally utilized to attach support components 2608 to one another. Some exemplary techniques include, for example, bonding, welding, adhering, or the like. FIG. 26G schematically shows an assembly that includes four gear structures 2604 from a side view according to one embodiment of the invention. Portions of support components 2608 that include threaded regions 2612 are also configured to be disposed through holes 2614 of rotational components 2602. Rotational component 2602 are configured to rotate around those portions of support components 2608.

III. Exemplary Rotary Mechanisms

In certain embodiments, the invention provides rotary or rotational mechanisms that include two or more rotational components or rotary units (e.g., 2, 3, 4, 5, 6, 7, 8, 9, 10, 11, 12, 13, 14, 15, or more rotational components or rotary units). Rotary mechanisms also typically include at least one counter-rotational mechanism operably coupled to one or more of the rotational components. The counter-rotational mechanism is generally configured to effect substantially simultaneous counter-rotation of the rotational components relative to one another when movement of at least a portion of the counter-rotational mechanism is effected. Rotary mechanisms also typically include drive mechanisms operably coupled to the counter-rotational mechanism and/or rotational components. Drive mechanisms are typically configured to effect movement of at least the portion of the counter-rotational mechanisms such that the rotational components substantially simultaneously counter-rotate relative to one another. In some embodiments, for example, multiple rotary units are included as components (e.g., rotational components and counter-rotational mechanisms, etc.) of rotary mechanisms.

Figure 6A:
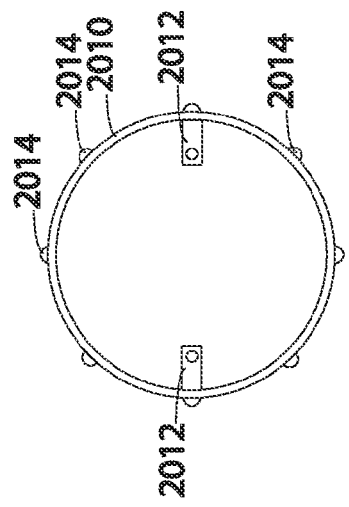
FIG. 6A schematically illustrates a positioning component of a rotary mechanism from a side view according to one embodiment of the invention.
Figure 6B:
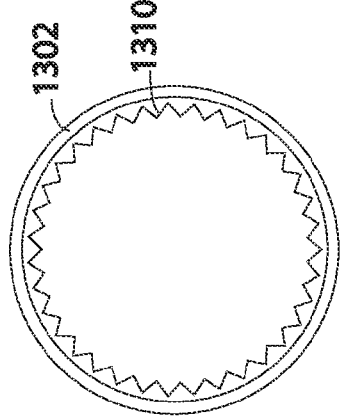
FIG. 6B schematically depicts a portion of a rotary mechanism that includes the rotational component of FIG. 1A from a side view according to one embodiment of the invention.
Figure 6C:
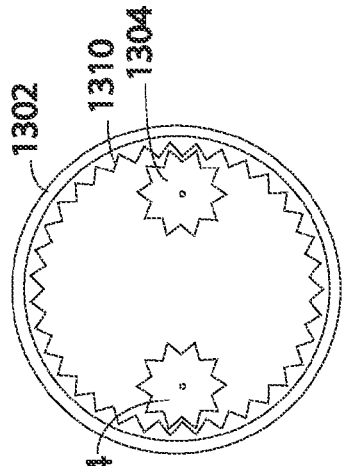
FIG. 6C schematically depicts a portion of a rotary mechanism that includes the rotational component of FIG. 1A and gear component of FIG. 1D from a side view according to one embodiment of the invention.

FIGS. 6A-O schematically show a rotary mechanism or components thereof according to exemplary embodiments of the Invention. As shown, rotary mechanism 2000 includes four rotary units that each include rotational component 1302 and gear component 1304. Rotary mechanism 2000 also includes a drive mechanism that includes shafts 2002 and motors 2004. Motors 2004 are configured to effect rotation of shafts 2002. As shown, the drive mechanism is configured to effect rotation of gear components 1304 such that rotational components 1302 of neighboring or adjacent pairs of rotary units rotate in opposite directions. See, e.g., the directional arrows in FIG. 6H, which schematically depict the counter-rotation of neighboring pairs of rotational components 1302. As shown, one shaft 2002 is operably connected to a first set of two non-neighboring gear components 1304, while the other shaft 2002 is operably connected to a second set of two non-neighboring gear components 1304 that is different from the first set of two non-neighboring of gear components 1304. The two shafts 2002 are configured to rotate in opposite directions. See, e.g., the directional arrows associated with shafts 2002 in FIGS. 6 H and I. As also shown, surfaces 1305 of rotational components 1302 are configured to rotate substantially non-perpendicular to a rotational axis of rotational components 1302.

Any suitable drive mechanism is optionally utilized with these rotary mechanisms. For example, FIG. 6L schematically depicts a portion of a drive mechanism from a side view. As shown, the drive mechanism includes motor 2004 (depicted as a dual shaft motor) that is configured to effect rotation of shafts 2002 in opposite directions via meshing pairs of gear components 2006. To further illustrate, FIGS. 6M-O schematically depict portions of a drive mechanism. As shown, motor 2004 is configured to effect rotation of shafts 2002 in opposite directions via a gear train that includes gear components 2008.

In addition, rotary mechanism 2000 also includes positioning component 2010 (shown as a frame structure) that is configured to position rotary units relative to one another. As shown, shafts 2002 are positioned relative to positioning component 2010 via mount brackets 2012, which permit rotation of shafts 2002. As also shown, positioning component 2010 also includes a plurality of friction reducing materials 2014 (shown as roller balls) disposed on a surface of positioning component 2010 to reduce friction as rotational components 1302 rotates relative to positioning component 2010. In the embodiments in which friction reducing materials are utilized, essentially any friction reducing material is optionally adapted for use with the rotary mechanisms of the invention. Other exemplary embodiments include, for example, coatings (e.g., TEFLON®, etc.), lubricants, surface features, and/or the like. FIG. 6G schematically depicts positioning component 2016 according to another exemplary embodiment.

FIGS. 7A-E schematically show rotary mechanisms or components thereof according to exemplary embodiments of the invention. As shown, rotary mechanism 2100 includes drive mechanism component 2102, which includes ring gear component 2104 and a gear structure. The gear structure includes support component 2106 and planetary gear component 2108 rotatably coupled to support component 2106. Planetary gear component 2108 is configured to operably engage ring gear component 2104 of drive mechanism component 2102 and gear component 1410 of rotary unit 1400. Drive mechanism component 2102 also includes motor 2110, which is configured to effect rotation of ring gear component 2104 via shaft 2112. Shaft 2112 is fixedly connected to ring gear component 2104. When ring gear component 2104 rotates, it effects the counter-rotation of neighboring pairs of rotary units 1400 relative to one another. See, e.g., the directional arrows associated with FIGS. 7 B and C, which schematically depict the counter-rotation of neighboring pairs of rotary units 1400. As also shown, in assembled rotary mechanism 2100, support component 2106 is operably connected to support components 1417 of rotary units 1400 such that support component 2106 and support components 1417 are substantially fixedly positioned relative to one another when ring gear component 2104 effects the counter-rotation of neighboring pairs of rotary units 1400 relative to one another. Gear structures that include support components 1417 are described further herein. To further illustrate, FIG. 7D schematically depicts rotary mechanism 2114, which includes rotary units 1400. In addition, FIG. 7E schematically illustrates rotary mechanism 2116, which includes rotary units 1400 and dual shaft motor 2118. Although not shown, rotary units 1400 typically include one or more implements (e.g., gear components, propellers, fan assemblies, fans, blades, compressors, boosters, combustors, turbines, nozzles, ducts, generators, motors, components thereof, etc.). Exemplary implements are described further herein.

The gear structures of the invention include various embodiments. To illustrate, FIG. 8A schematically illustrates gear structure 1415 prior to assembly with another gear structure 1415 from a side view according to one embodiment of the invention. As shown, gear structure 1415 includes support component 1417 and gear components 1414 (e.g., planetary gear components or the like), which are rotatably coupled to support component 1417. Gear components 1414 are configured to operably engage or mesh with one or more other gear components when gear components 1414 are disposed proximal to the other gear components. During assembly, threaded region 1429 of one support component 1417 is inserted into threaded region receiving area 1427 of another support component 1417 such that the assembled support components 1417 are substantially fixedly positioned relative to one another when rotational components 1402 of rotary units 1400 rotate relative to support components 1417 and to one another. Essentially any attachment technique is optionally utilized to attach support components 1417 to one another. Some exemplary techniques include, for example, bonding, welding, adhering, or the like. In some embodiments, multiple support components 1417 are fabricated as single integral part (e.g., as a molded part or the like). FIG. 8B schematically shows an assembly of four gear structure 1415 from a side view. FIG. 8C schematically depicts the gear structure assembly of FIG. 8B from a rear side view, while FIG. 8D schematically depicts the gear structure assembly of FIG. 8B from a front side view.

To further illustrate, FIG. 8E schematically shows rotary mechanism 2200 that includes the gear structure assembly of FIG. 8B from a sectional view according to one embodiment of the invention. As shown, rotary mechanism 2200 includes four rotary units 1400. Counter-rotation of neighboring rotational components 1402 in rotary mechanism 2200 is effected by drive mechanism component 2202, which includes shaft component 2204 and gear component 2206. FIG. 8F schematically shows rotary mechanism 2200 from a side view. Rotational components 1402 of rotary units 1400 of rotation mechanism 2200 are configured to rotate relative to support components 1417, which support components 1417 are substantially fixedly positioned when rotational components 1402 rotates relative to support components 1417. Gear components 1414 are configured to rotate relative to rotational components 1402.

Figure 9S:
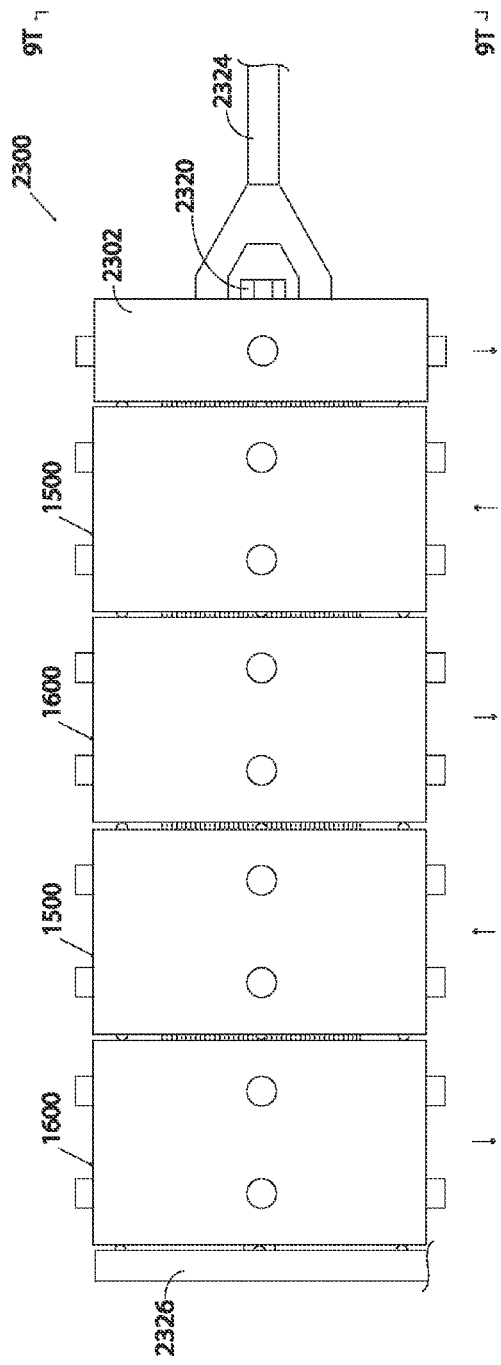
FIG. 9S schematically depicts a side view of the rotational mechanism from FIG. 9B and the portion of the drive mechanism component of FIG. 9E according to one embodiment of the invention.
Figure 9T:
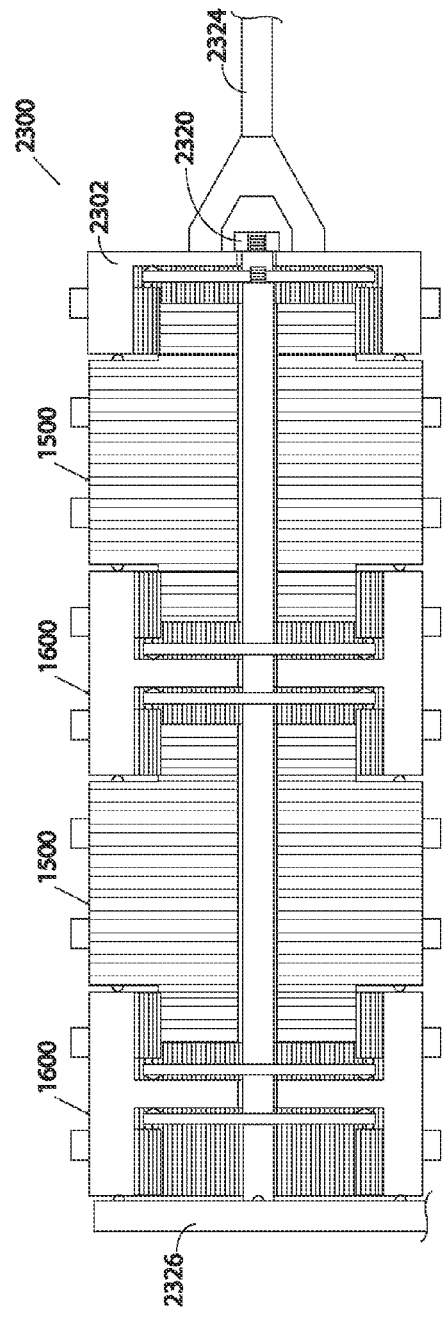
FIG. 9T schematically depicts a sectional side view of the rotational mechanism from FIG. 9B and the portion of the drive mechanism component of FIG. 9E according to one embodiment of the invention.
Figure 10A:
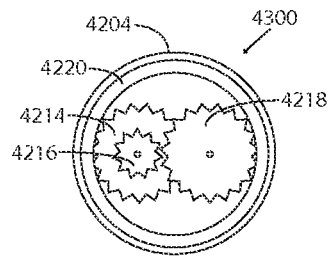
FIGS. 10A-I schematically illustrate a rotary mechanism or components thereof from various views according to one exemplary embodiment of the invention.
Figure 10B:
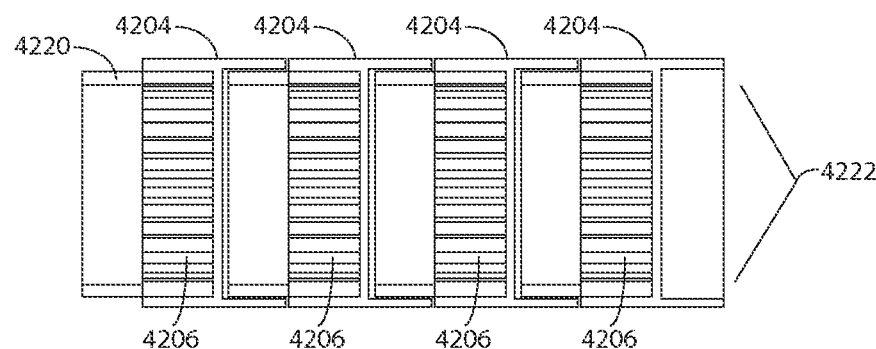
Figure 10C:
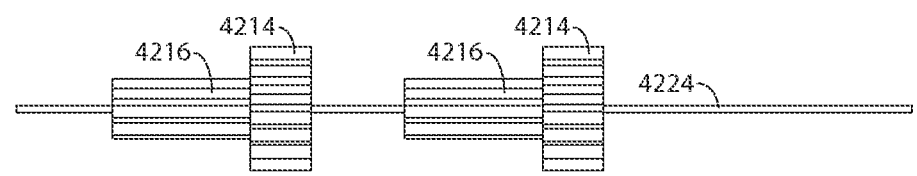
Figure 10D:
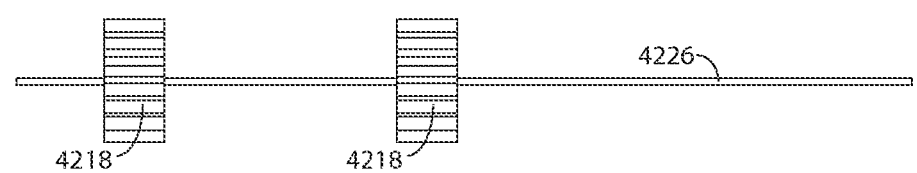
Figure 10E:
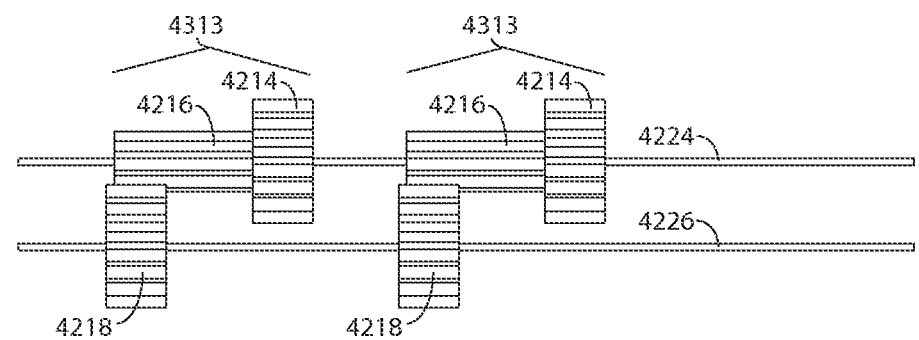
Figure 10F:
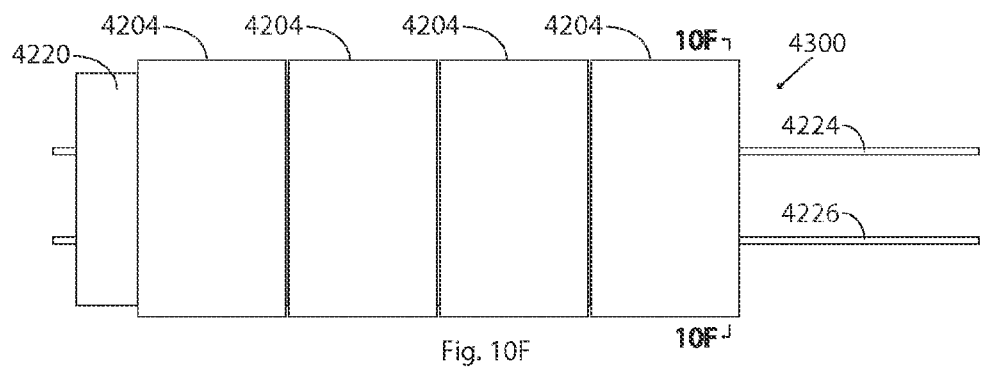
Figure 10G:
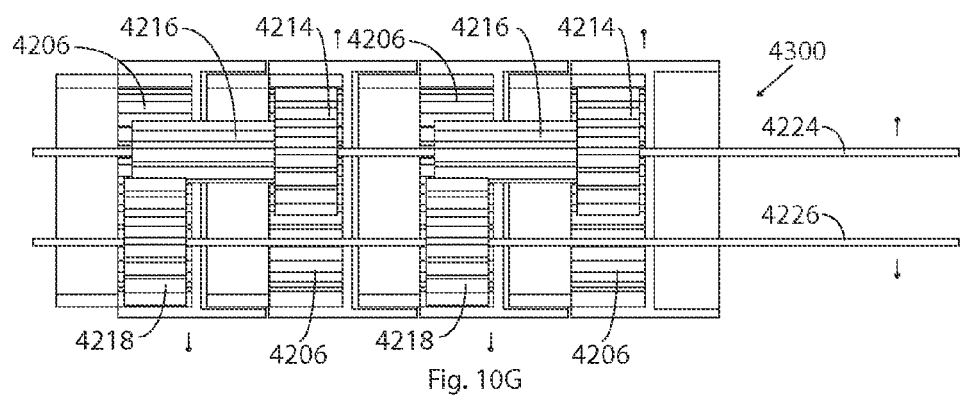
Figure 10H:
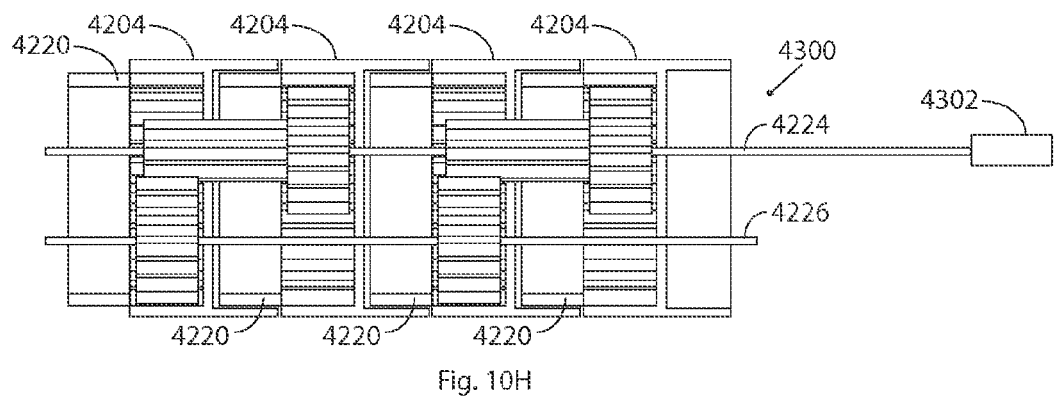
Figure 10I:
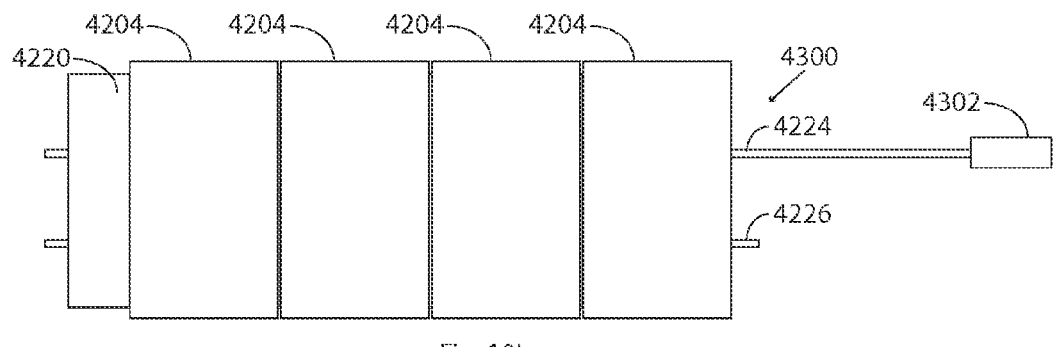

FIGS. 9A-T schematically depict a rotational mechanism or components thereof according to one embodiment of the invention. To illustrate, FIGS. 9A and C, for example, schematically depicts a portion of rotational mechanism 2300 from an exploded side and exploded side sectional views, respectively. During assembly of rotational mechanism 2300, support component 1614 of one rotary unit 1600 is inserted through hole 1508 of rotary unit 1500 and threaded region 1632 of that support component 1614 is received and retained in threaded region receiving area of another rotary unit 1600.

FIGS. 9E-P schematically show a portion of a drive mechanism component that is utilized to effect counter-rotation of neighboring pairs of rotary unit 1500 and rotary unit 1600 of rotational mechanism 2300. As shown, the portion of the drive mechanism component includes rotational component 2302, which includes ring gear component 2304, hole 2306, and implements 2308. Essentially any implement is optionally adapted for use with rotational mechanism 2300 or the other rotational or rotary mechanism described herein, such as gear components, propellers, fan assemblies, fans, blades, compressors, boosters, combustors, turbines, nozzles, ducts, generators, motors, components thereof, and the like. Exemplary implements are described further herein. The portion of the drive mechanism component also includes gear structure 2310, which includes support structure 2312 and planetary gear components 2314 rotatably coupled to support structure 2312. Support structure 2312 also includes friction reducing materials 2316 (shown as elevated or pointed surface features) to, e.g., reduce friction between support structure 2312 and rotational component 2302 when rotational component 2302 rotates relative to support structure 2312. Support structure 2312 also includes threaded region 2318, which is received by a corresponding threaded region receiving area of fastener 2320 (e.g., a nut or the like) through hole 2306 to hold gear structure 2310 in position relative rotational component 2302, yet permit rotational component 2302 to rotate relative to support structure 2312 and planetary gear components 2314. In addition, support structure 2312 also includes threaded region receiving area 2322, which is configured to receiving thread region 1632 of a rotary unit 1600, e.g., in assembled rotational mechanism 2300.

As also shown, a shaft 2324 is also fixedly connected to rotational component 2302. Although not shown, a motor or the like is typically operably connected to shaft 2324, which effects the rotation of shaft 2324 and the counter-rotation of neighboring pairs of rotary unit 1500 and rotary unit 1600 of rotational mechanism 2300 (e.g., as schematically depicted by the directional arrows shown, e.g., in FIG. 9S) during operation. In addition, a rotary unit 1600 also operably connects to support component 2326 via threaded region receiving area 1634 of support structure 1614, e.g., such that support structures 1614 of rotary units 1600 and support structure 2312 of gear structure 2310 are substantially fixedly positioned when rotary units 1500, rotary units 1600, and rotational component 2302 rotate relative to one another in rotational mechanism 2300. Essentially any support component is optionally used. In some embodiments, support components are included in or as part of devices, apparatus, or other applications of the rotational mechanisms of the invention. Exemplary support components and applications are described herein.

FIGS. 10 A-I schematically illustrate a rotary mechanism or components thereof from various views according to one exemplary embodiment of the invention. As shown, rotary mechanism 4300 includes rotational components 4204, which include gear components 4206 (e.g., ring gear components). Rotary mechanism 4300 also includes counter-rotational mechanism 4313 that includes first gear components 4214 that operably engage (e.g., mesh with) a ring gear component 4206 of a first rotational component 4204 of a neighboring pair of rotational components. Counter-rotational mechanism 4313 also includes second gear components 4218 that operably engage (e.g., mesh with) a ring gear component 4206 of a second rotational component 4204 of a neighboring pair of rotational components. Counter-rotational mechanism 4313 also includes third gear components 4216 that operably engage (e.g., mesh with second gear components 4218 such that when first gear components 4214 rotate in a first direction, first rotational components 4204 of neighboring pairs of rotational components rotate in the first direction and second gear components 4218 and second rotational components 4204 of neighboring pairs of rotational components rotate in a second direction (e.g., substantially opposite the first direction).

Rotational components 4204 include alignment components 4220 and alignment component receiving areas 4222 that are configured to align rotational components 4204 relative to one another, e.g., when rotational components 4204 rotate. As shown, an alignment component receiving area 4222 of a given rotational component 4204 is configured to receive at least a portion of an alignment component 4220 of another rotational component 4204. In this exemplary embodiment, alignment components 4220 are shown as circular ridge structures. Other alignment components or mechanisms are also optionally used to align rotational components relative to one another in the rotary mechanisms of the invention. In some embodiments, friction reducing materials are disposed between neighboring pairs of rotational components in a rotary mechanism to reduce friction between the rotational components when the rotational components rotate relative to one another. In some embodiments, for example, one or more lubricants are disposed between at least one neighboring pair of rotational components 4204 before and/or after the alignment component 4220 of one rotational component 4204 is inserted into the alignment component receiving area 4222 of another rotational component 4204. Other exemplary friction reducing materials that are optionally used or adapted for use with the rotary mechanisms of the invention are described herein or otherwise known to those of skill in the art.

Rotary mechanism 4300 also includes drive mechanism components or portions thereof 4224 and 4226 (e.g., shown as shaft components in this exemplary embodiment). As shown, shaft component 4224 operably engages first gear components 4214 and third gear components 4216, while shaft component 4226 operably engages second gear components 4218. As also shown, rotary mechanism 4300 also includes drive mechanism components or portions thereof 4302 (e.g., shown as motor in this exemplary embodiment) operably connected to shaft component 4224. Motor 4302 is configured to effect rotation of shaft component 4224 and thereby first gear components 4214 and third gear components 4216 as well as shaft component 4226 and second gear components 4218 such that when first gear components 4214 rotate in a first direction, first rotational components 4204 of neighboring pairs of rotational components rotate in the first direction and second gear components 4218 and second rotational components 4204 of neighboring pairs of rotational components rotate in a second direction (e.g., substantially opposite the first direction). Rotary mechanism 4300 is typically operably incorporated into, or otherwise operably associated with, a device, vehicle, or the like. Exemplary devices, vehicles, or other applications that are optionally used or adapted for use with rotary mechanism 4300 or the like are, e.g., described further herein.

Rotary mechanisms or components thereof are fabricated or assembled using various techniques. In some embodiments, rotary mechanisms are assembled using rotational components that include multiple portions. As shown in FIGS. 44 A-C, for example, a rotary mechanism is optionally assembled using rotational components 4400, which each include rotational component portion 4402 and rotational component portion 4404. Rotational component portions 4402 and rotational component portions 4404 include portions of the ring gear components, alignment components, and alignment component receiving areas described herein, e.g., with respect to rotational components 4204. Rotational component portions 4402 also include alignment features 4406 and rotational component portions 4404 also include corresponding alignment feature receiving areas (not within view) that are configured to receive alignment features 4406. As shown, during assembly, rotational component portions 4402 and rotational component portions 4404 are joined (e.g., adhered, bonded, welded, etc.) with one another and positioned in operable engagement with first gear components 4214 and second gear components 4218 to form rotary mechanisms.

In certain embodiments, rotary mechanisms are assembled using shaft components that include multiple portions. FIGS. 12 A and B, 13 A and B, 14 A and B, and 15 show aspects of one of these exemplary embodiments. As shown, shaft component portion 4500 includes drive mechanism component receiving area 4700 and shaft component portion 4502 includes notched portion 4702 that is configured to be received by drive mechanism component receiving area 4700 of shaft component portion 4500. Shaft component portion 4500 and shaft component portion 4502 are each operably connected to a first gear component 4214. In addition, shaft component portion 4504 includes drive mechanism component receiving area 4700 and shaft component portion 4506 includes notched portion 4702 that is configured to be received by drive mechanism component receiving area 4700 of shaft component portion 4504. Shaft component portion 4504 and shaft component portion 4506 are each operably connected to a second gear component 4218. As shown, for example, in FIG. 15 rotational components 4204 are positioned relative to first gear components 4214 operably connected to shaft component portion 4500 or shaft component portion 4502 or second gear components 4218 operably connected to shaft component portion 4504 or shaft component portion 4506 and corresponding drive mechanism component receiving areas 4700 and notched portions 4702 are joined together during the assembly of a rotary mechanism in this exemplary embodiment. In some embodiments, multiple shaft portions and multiple rotational component portions are used together in the assembly of rotary mechanisms. Other exemplary rotary mechanism or component fabrication and assembly techniques are described herein.

Although not shown, rotational components 4204 of rotary mechanism 4300 also typically include implements (e.g., gear components, propellers, fan assemblies, fans, blades, compressors, boosters, combustors, turbines, nozzles, ducts, generators, motors, components thereof, etc.). Exemplary implements that are optionally used or adapted for use with rotational components 4204 are described further herein. In some embodiments, for example, implements are rotatably coupled to rotational components. In some of these embodiments, implements are configured to operably engage one or more gear components of one or more other rotational components.

FIGS. 16 A-F schematically show a rotary mechanism or components thereof from various views according to one exemplary embodiment of the invention. As shown, rotary mechanism 5100 includes rotary units that include rotational components 4204. Rotational components 4204 include gear components 4206 (e.g., ring gear components). Additional details about rotational components (e.g., rotational components 4204) are described further herein. The rotary units also include second gear components 4218, which are configured to operably engage gear components 4206 of rotational components 4204. Rotary mechanism 5100 also includes a drive mechanism component or portion thereof that operably engages second gear components 4218. The drive mechanism component or portion thereof is configured to effect rotation of second gear components 4218 such that rotational component 4204 of one rotary unit of a neighboring pair of rotary units rotates in a first direction and rotational component 4204 of the other rotary unit of the neighboring pair of rotary units rotates in a second direction. As shown, the drive mechanism component or portion thereof includes shaft component 5102 and shaft component 5104. Shaft component 5102 operably engages second gear components 4218 of one rotary unit of each neighboring pair of rotary units, while shaft component 5104 operably engages second gear components 4218 of the other rotary unit of each neighboring pair of rotary units. Shaft component 5102 and shaft component 5104 are also operably connected to drive gear components 5106 and 5108, respectively. In assembled rotary mechanism 5100, drive gear components 5106 and 5108 mesh with one another. As shown, shaft component 5102 is also operably connected to motor 5110. Motor 5110 is configured to effect rotation of shaft component 5102 and thereby second gear components 4218 and corresponding rotational components 4204 of one rotary unit of each neighboring pair of rotary units in a first direction and second gear components 4218 and corresponding rotational components 4204 of the other rotary unit of each neighboring pair of rotary units via drive gear components 5106 and 5108 and shaft component 5104 in a second direction. In some embodiments, rotary mechanisms also include drive mechanism positioning components that are configured to position drive mechanism components or portions thereof relative to one another. To illustrate, rotary mechanism 5100 includes drive mechanism positioning component 5112, which includes holes 5114. Shaft component 5102 and shaft component 5104 are configured to fit and rotate within holes 5114 such that shaft component 5102 and shaft component 5104 are positioned relative to one another at least during rotation. Rotary mechanism 5100 is typically operably incorporated into, or otherwise operably associated with, a device, vehicle, or the like. Exemplary devices, engines, vehicles, aircraft, or other applications that are optionally used or adapted for use with rotary mechanism 5100 or the like are, e.g., described further herein.

To further illustrate, FIG. 27A schematically illustrates rotary mechanism 2700 that includes rotational components 2602 and gear structure 2604 of FIGS. 26A-G from a sectional view prior to assembly according to one embodiment of the invention. As shown, FIG. 27A also schematically depicts a portion of a drive mechanism component that is utilized to effect counter-rotation of neighboring pairs of rotational components 2602 (see, e.g., directional arrows in FIG. 27B). As shown, the portion of the drive mechanism component includes rotational component 2601, which includes gear component 2603 and hole 2605. In some embodiments, rotational component 2601 also includes one or more implements. Exemplary implements are described further herein. A threaded region 2612 of one support component 2608 is inserted through hole 2605 and received by a corresponding threaded region receiving area of fastener 2607 (e.g., a nut or the like) to hold the gear structure in position relative rotational components 2602, yet permit rotational components 2602 to rotate relative to support components 2608 and gear components 2610.

As also shown, a shaft 2609 is also fixedly connected to rotational component 2601. In this exemplary embodiment, motor 2611 is operably connected to shaft 2609, which effects the rotation of shaft 2609 and the counter-rotation of neighboring pairs of rotational components 2602 of rotary mechanism 2700 (e.g., as schematically depicted by the directional arrows shown, e.g., in FIG. 27B) during operation. In addition, a support component 2608 also operably connects to support component 2613 via a threaded region receiving area 2608 (not within view) of support structure 2608, e.g., such that support components 2608 and support component 2613 are substantially fixedly positioned when rotational components 2602 of rotary mechanism 2700 rotate relative to one another in rotary mechanism 2700. Support component 2613 also includes gear component 2615 that operably engages or meshes with a pair of gear components 2610 in this exemplary embodiment. Essentially any support component is optionally used. In some embodiments, support components are included in or as part of devices, apparatus, or other applications of the rotational mechanisms of the invention. Exemplary support components and applications are described herein. FIG. 27B schematically depicts rotary mechanism 2700 of FIG. 27A from a sectional view following assembly.

IV. Exemplary Applications

To further illustrate representative embodiments, rotary units and rotary mechanisms are optionally used or adapted for use in various types of engines and other propulsion devices or systems. For example, FIGS. 17 A-F, 18 A-E, and 19 A-D schematically illustrate propulsion devices or components thereof according to certain embodiments of the invention. As shown, propulsion device 3000 includes two rotary mechanisms 3002 and propeller component 3004. Rotary mechanisms 3002 include a plurality of rotary units 300. Any rotary unit or rotary mechanism described herein is optionally adapted for use in propulsion device 3000, e.g., instead of rotary units 300. Rotary units 300 are operably coupled to one another via shaft 3006, which includes gear component 3008. Shaft 3006 operably connects to motor 3010 and rotary mechanism cap 3012. Gear component 3008 operably engages third gear components 312 of gear structure 310 of a rotary unit 300 such that when motor 3010 effects the rotation of gear component 3008, gear component 3008 effects the counter rotation of neighboring pairs of rotary units 300. Gear components 324 of rotary units 300 operably engage corresponding gear components of propeller units 3014 (e.g., rotational units or the like) to effect the counter rotation of neighboring pairs of propeller units 3014 of propeller component 3004, and thereby propulsion. Rotary mechanism cap 3012 aligns and maintains the position of rotary units 300 relative to one another. Although two rotary mechanisms 3002 are depicted in this propulsion device embodiment, fewer or more that two rotary mechanisms are optionally used.

FIGS. 19 A-D schematically illustrate a propulsion device or components thereof according to one embodiment of the invention. As shown, propulsion device 3200 includes two rotary mechanisms 3202 and propeller component 3004. Rotary mechanisms 3202 include a plurality of rotational components 3204. Rotational components 3204 are fixedly coupled to one another via shaft 3206. Shaft 3206 operably connects to motor 3010 and rotary mechanism cap 3012. As shown, one shaft 3206 is fixedly coupled to a first set of four non-neighboring gear components 3204, while the other shaft 3206 is fixedly coupled to a second set of four non-neighboring gear components 3204 that is different from the first set of four non-neighboring of gear components 3204. The two shafts 3206 are configured to rotate in opposite directions. See, e.g., the directional arrows associated with the two rotary mechanisms 202 in FIG. 19B. As shown, in an assembled propulsion device 3200, gear components 3204 of the first and second sets of four non-neighboring of gear components 3204 mesh with corresponding gear components of different propeller units 3014 (e.g., rotational units or the like) of propeller component 3004 such that when the first and second sets of four non-neighboring of gear components 3204 rotate in opposite directions to one another, neighboring pairs of propeller units 3014 of propeller component 3004 counter-rotate relative to one another, and thereby effect propulsion.

Propeller component 3004 of propulsion device 3000 and 3200 includes a plurality of propeller units 3014 (e.g., rotational units or the like), which in this embodiment each include a plurality of propellers 3016. Many different types of propellers are optionally used or adapted for use in the engines or propulsion devices of the invention. In some embodiments, for example, individual propeller components 3004 may have propellers 3016 that differ in size from the propellers of other propeller components in a given propulsion device 3000 or propulsion device 3200. Propeller units 3014 are operably coupled together in propeller component 3004 via propeller component shaft 3018 and propeller component cap 3020. As also shown, certain propeller units 3014 include rotational alignment components 3022, which are positioned and rotate in corresponding rotational positioning components 3107 of propulsion component housing 3100 (e.g., a positioning component or the like), e.g., to prevent propeller units 3014 from contacting propulsion component housing 3100 during operation. See, e.g., FIGS. 18 D and E.

The engine and propulsion devices have many different uses. For example, they are optionally used or adapted for use with watercraft (e.g., boats, submarines, surfboards, personal watercraft, diving or scuba propulsion aides, and the like), aircraft, and other vehicles and devices. To illustrate, FIGS. 20 A and B schematically depict boat 3300, which includes several housed propulsion devices 3302. To further illustrate, FIGS. 21A and B schematically depict aircraft 3400, which includes housed propulsion devices 3402.

Figure 22:
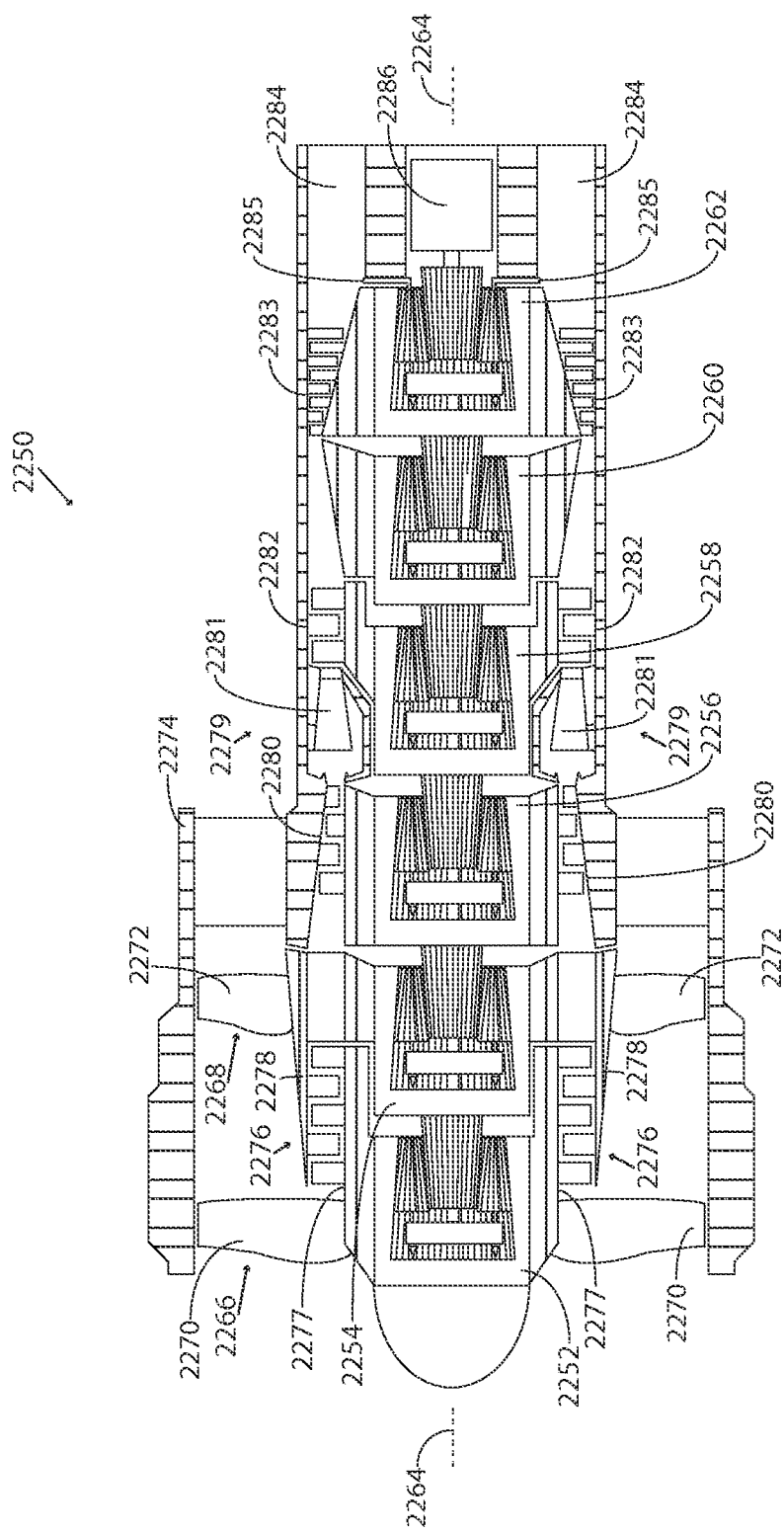
FIG. 22 schematically illustrates a portion of a turbofan engine from a cross-sectional side view according to one embodiment of the invention.
Figure 23A:
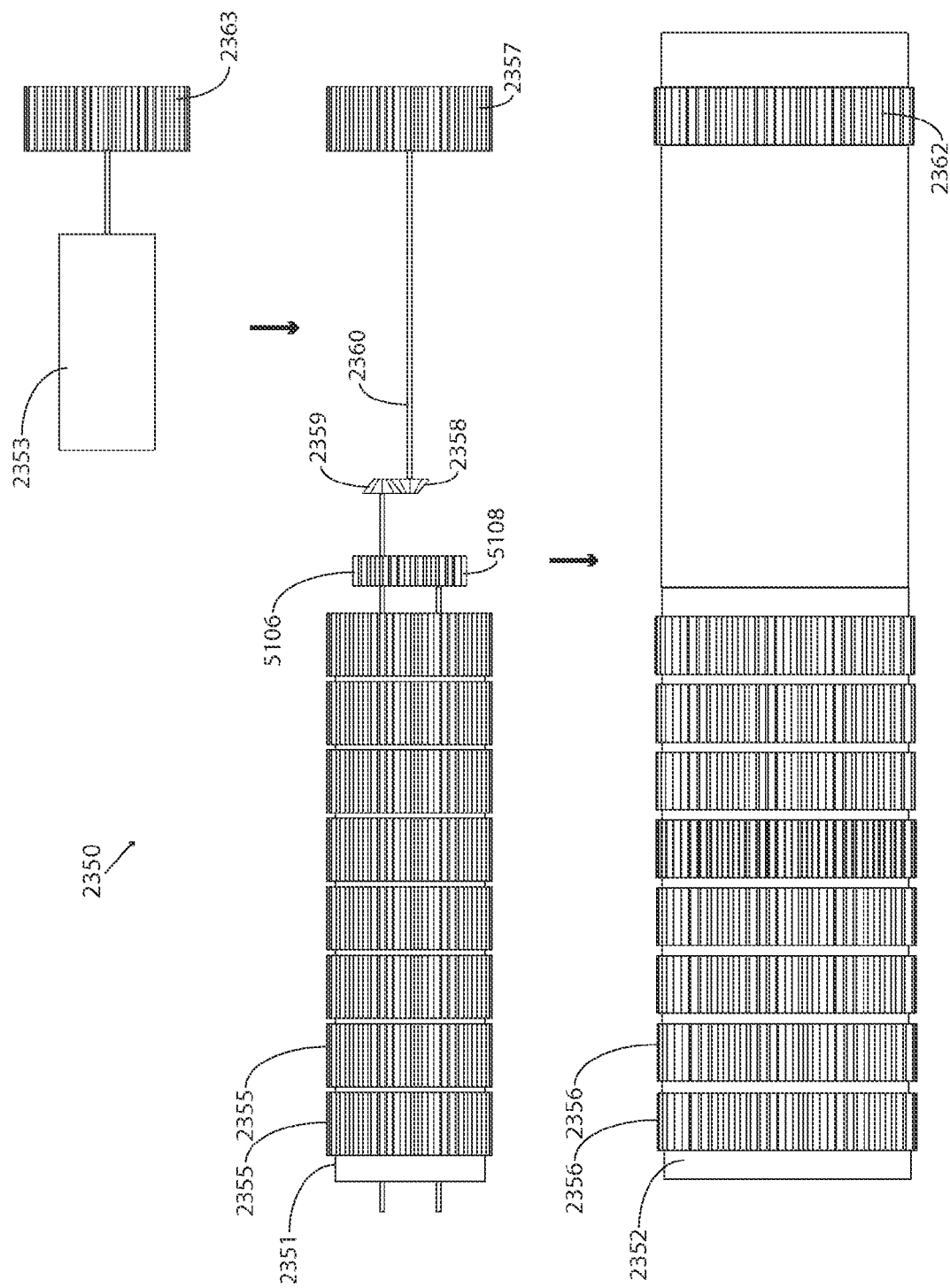
FIG. 23A schematically depicts a portion of a gas turbine engine prior to positioning rotary and propulsion mechanisms relative to one another from a side view according to one embodiment of the invention.
Figure 23B:
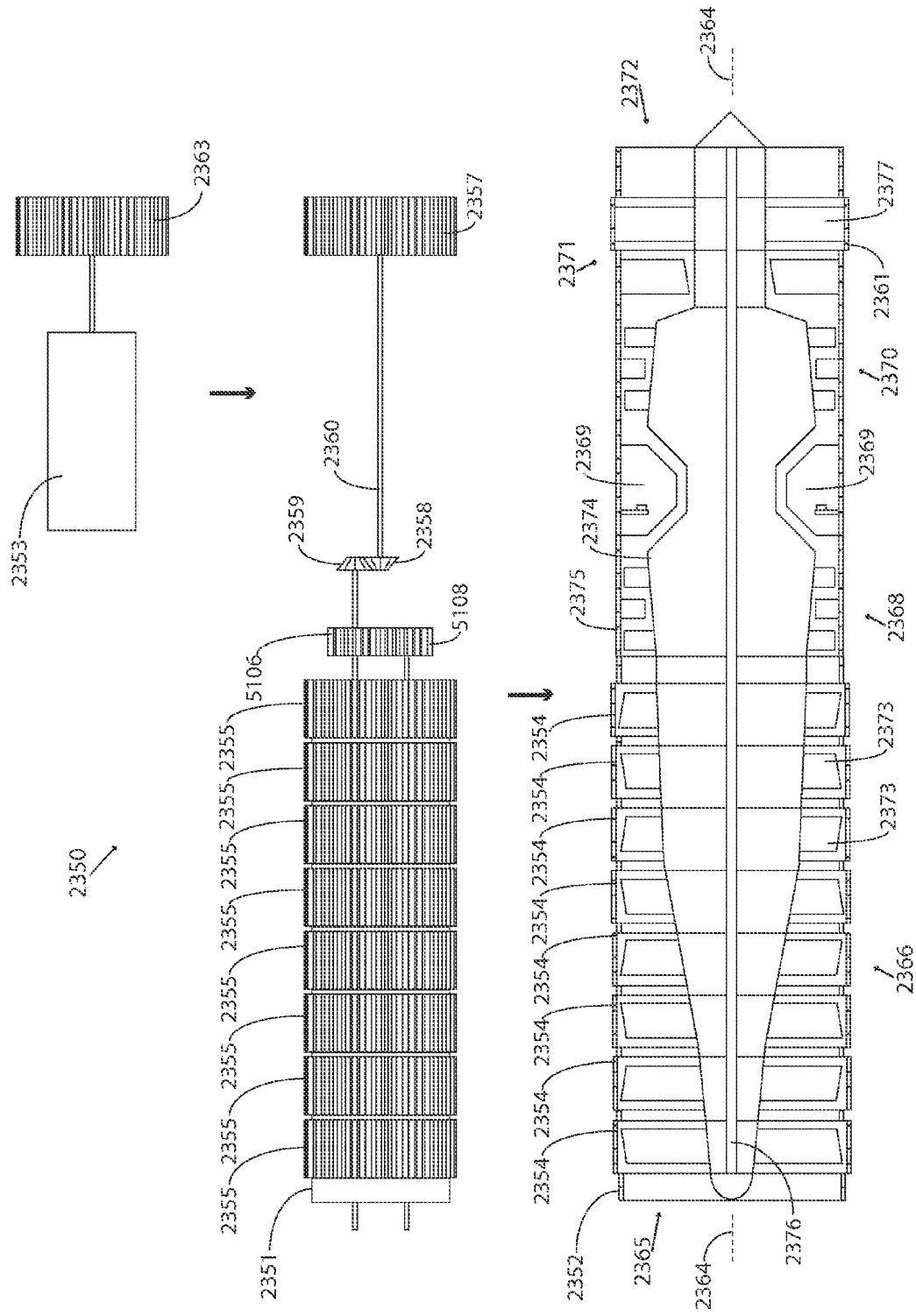
FIG. 23B schematically shows the gas turbine engine portion from FIG. 23A with a cross-sectional side view of the propulsion mechanism.
Figure 23C:
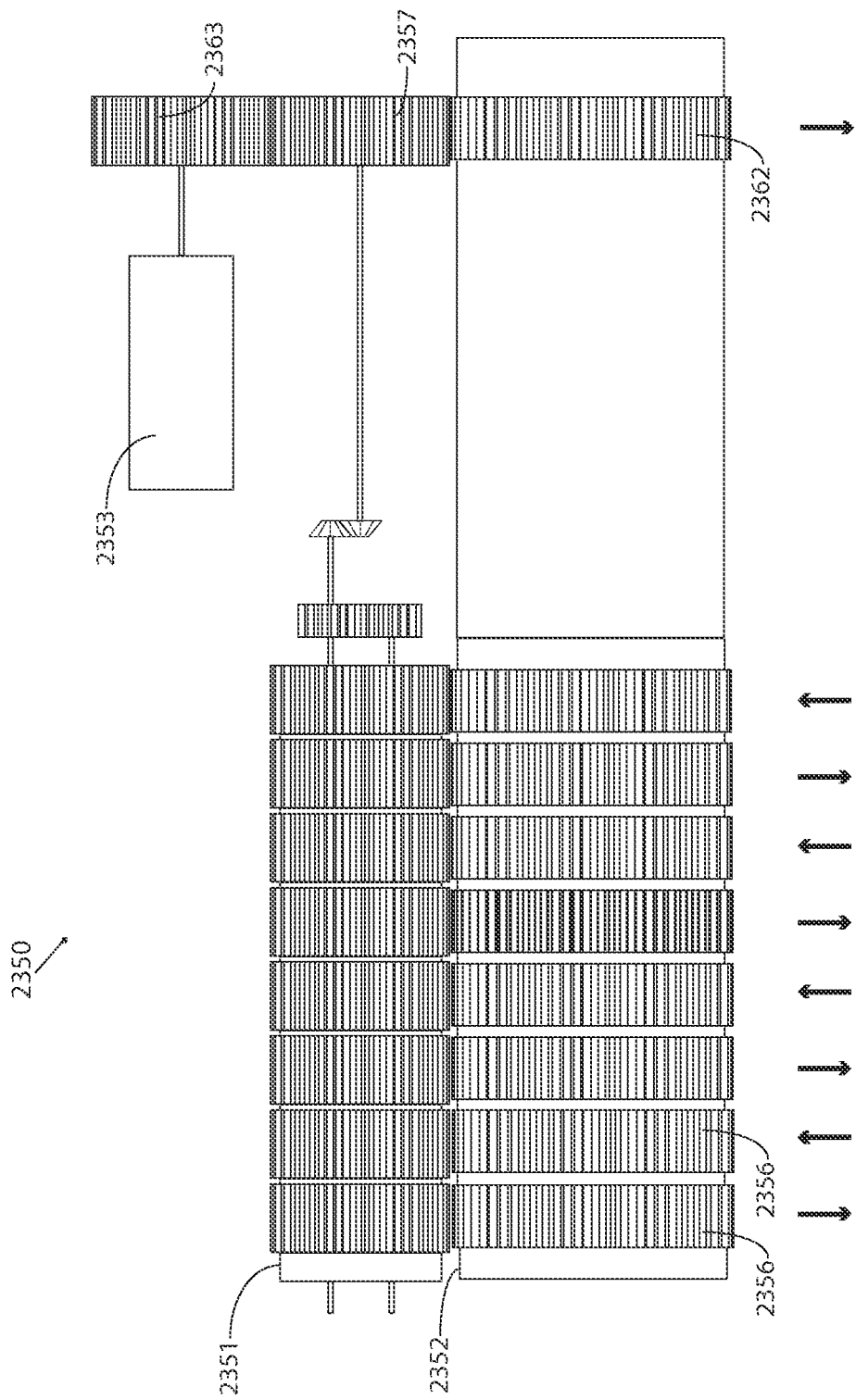
FIG. 23C schematically shows the gas turbine engine portion from FIG. 23A with the rotary and propulsion mechanisms positioned relative to one another from a side view.
Figure 23D:
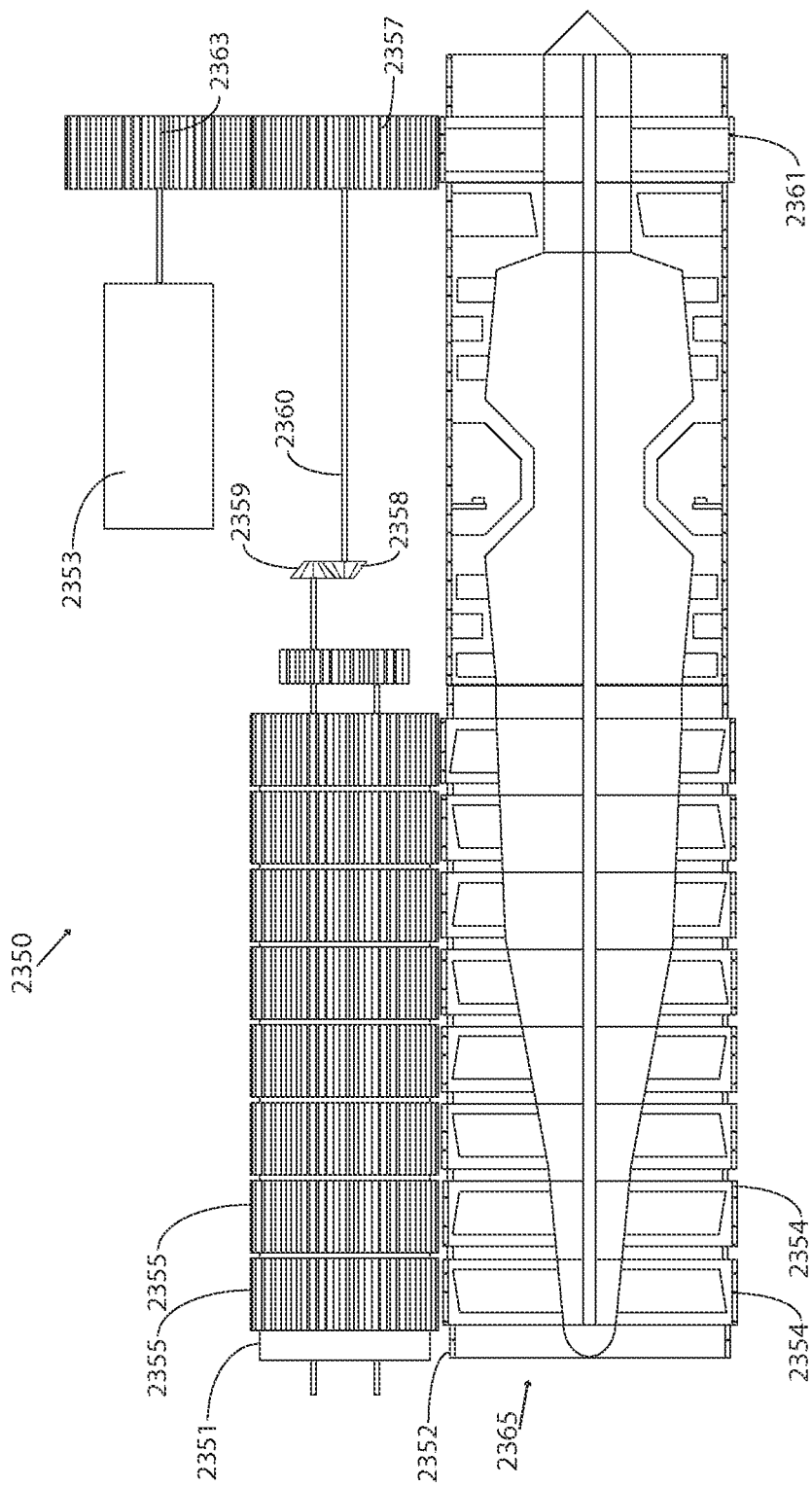
FIG. 23D schematically illustrates the gas turbine engine portion from FIG. 23C with a cross-sectional side view of the propulsion mechanism.

FIG. 22 schematically illustrates a portion of a turbofan engine from a cross-sectional side view according to one embodiment of the invention. As shown, turbofan engine assembly 2250 includes a rotary mechanism that includes rotary units 2252, 2254, 2256, 2258, 2260, and 2262, respectively, which are configured similar to rotary units 1400, as described herein. Neighboring pairs of rotational components of rotary units in the rotary mechanism are configured to counter-rotate relative to one another around rotational axis 2264. Each rotary unit in this exemplary embodiment includes one or more implements or portions thereof. Rotary unit 2252 includes forward fan assembly 2266 and rotary unit 2254 includes aft fan assembly 2268 positioned downstream from forward fan assembly 2266 along rotational axis 2264. In the illustrated exemplary embodiment, fan assemblies 2266 and 2268 are positioned at a forward end of turbofan engine 2250. In other embodiments, fan assemblies 2266 and 2268 are positioned in other locations, such as proximal to an aft end of turbofan engine 2250. Fan assemblies 2266 and 2268 each include a plurality of fan blades 2270 and 2272 that are coupled to respective rotational components of rotary unit 2252 and rotary unit 2254. Fan assemblies 2266 and 2268 are positioned within nacelle 2274. Turbofan engine 2250 also includes booster compressor 2276. In the exemplary embodiment shown, booster compressor 2276 includes radially inner rotor section 2277 that includes a plurality of rows of blades. Rotor section 2277 is coupled to rotary unit 2252 and rotates in the same rotational direction and at the same rotational speed as forward fan assembly 2266. Outer rotor section 2278 is coupled to aft fan assembly 2268 and rotary unit 2254, and rotates in the same rotational direction and at the same rotational speed as aft fan assembly 2268. Outer rotor section 2278 includes a plurality of rows of blades, and counter-rotates relative to inner rotor section 2277. In the exemplary illustrated embodiment, booster compressor 2276 is positioned axially downstream from forward fan assembly 2266 such that booster compressor 2276 is disposed between forward fan assembly 2266 and aft fan assembly 2268.

Turbofan engine 2250 also includes core gas turbine engine 2279 that is downstream from forward fan assembly 2266 and aft fan assembly 2268. Core gas turbine engine 2279 includes high-pressure compressor 2280, combustors 2281, and high-pressure turbine 2282. High-pressure compressor 2280 includes a plurality of rows of blades that are alternatingly coupled in an axially inter-digitated configuration to rotary unit 2256 and nacelle 2274. The blades of high-pressure compressor 2280 that are coupled to rotary unit 2256 (structured as an inner rotor section) rotate in the same rotational direction as the rotational component of rotary unit 2256. Combustors 2281 are coupled to nacelle 2274. High-pressure turbine 2282 includes a plurality of rows of blades that are alternatingly coupled in an axially inter-digitated configuration to rotary unit 2258 and nacelle 2274. The blades of high-pressure turbine 2282 that are coupled to rotary unit 2258 (structured as an inner rotor section) rotate in the same rotational direction as the rotational component of rotary unit 2258. In operation, core gas turbine engine 2279 generates combustion gases that are channeled downstream to high-pressure turbine 2282 and low-pressure turbine 2283, which extracts energy from the gases for powering forward fan assembly 2266 and aft fan assembly 2268 through the rotary mechanism of turbofan engine 2250. Low-pressure turbine 2283 includes a plurality of rows of blades that are alternatingly coupled in an axially inter-digitated configuration to rotary unit 2262 and nacelle 2274. The blades of low-pressure turbine 2283 that are coupled to rotary unit 2262 (structured as an inner rotor section) rotate in the same rotational direction as the rotational component of rotary unit 2262. Various numbers of rotor disks are optionally used in the rotor sections of the engines and other devices described herein. Turbofan engine 2250 also includes exhaust nozzle 2284. As also shown, the support component of the gear structure of rotary unit 2262 is coupled to nacelle 2274 via brackets 2285, e.g., to fixedly position the support components of the gear structures of the rotary mechanism of turbofan engine 2250 during operation. Turbofan engine 2250 also includes motor/generator 2286 operably connected to rotary unit 2262. Motor/generator 2286 is configured to selectively operate as a motor (e.g., to provide mechanical power to the rotary mechanism of turbofan engine 2250 during engine start-up, etc.) and as a generator (e.g., to provide electrical power to accessory electrical aircraft components, etc.).

FIGS. 23A-D schematically depict gas turbine engine assembly or components thereof from various views according to one embodiment of the invention. As shown, gas turbine engine 2350 includes rotary mechanism 2351, propulsion mechanism 2352, and motor/generator 2353. Rotary mechanism 2351 is configured similar to rotary mechanism 5100 as described herein. The implements of the rotational components of rotary mechanism 2351 are gear components 2355 that mesh with corresponding gear components 2356 of propulsion units 2354 of propulsion mechanism 2352. Rotary mechanism 2351 is operably coupled to gear component 2357 via gear components 2358 and 2359 and shaft component 2360. Gear component 2357 meshes with corresponding gear component 2362 of propulsion unit 2361 of propulsion mechanism 2352. Gear component 2357 also meshes with corresponding gear component 2363 of motor/generator 2353. Motor/generator 2353 is configured to selectively operate as a motor (e.g., to provide mechanical power to rotary mechanism 2351 during engine start-up, etc.) and as a generator (e.g., to provide electrical power to accessory electrical aircraft components, etc.).

Propulsion mechanism 2352 of gas turbine engine 2350 includes a plurality of propulsion units 2354 that are configured to rotate around rotational axis 2364. In axial flow series, propulsion mechanism 2352 includes air intake 2365, low-pressure compressor 2366, high-pressure compressor 2368, combustors 2369, high-pressure turbine 2370, low-pressure turbine 2371, and exhaust nozzle 2372 that are coupled to one another via interconnecting shafts component 2376. Propulsion units 2354 and 2361 each include a plurality of blades 2373 and 2377, respectively. During operation, blades 2373 of neighboring pairs of propulsion units 2354 counter-rotate relative to one another. Air enters air intake 2365 and flows into low-pressure compressor 2366, which compresses the air flow directed into it before delivering that air to high-pressure compressor 2368 where further compression takes place. The compressed air exhausted from high-pressure compressor 2368 is directed into combustors 2369 where it is mixed with fuel and the mixture combusted. The resultant hot combustion products then expand through, and thereby drive high-pressure turbine 2370 and low-pressure turbine 2371 before being exhausted through exhaust nozzle 2372 to provide propulsive thrust. Low-pressure turbine 2371 effects the rotation of gear component 2357 and the rotational components of rotary mechanism 2351, which effects the rotation of blades 2373 of propulsion units 2354 of propulsion mechanism 2352. Low-pressure turbine 2371 effects the rotation of core engine component 2374 within nacelle 2275 via suitable interconnecting shafts. High-pressure compressor 2368 and high-pressure turbine 2370 each include a plurality of rows of blades that are alternatingly coupled in an axially inter-digitated configuration to core engine component 2374 and nacelle 2275.

Figure 24:
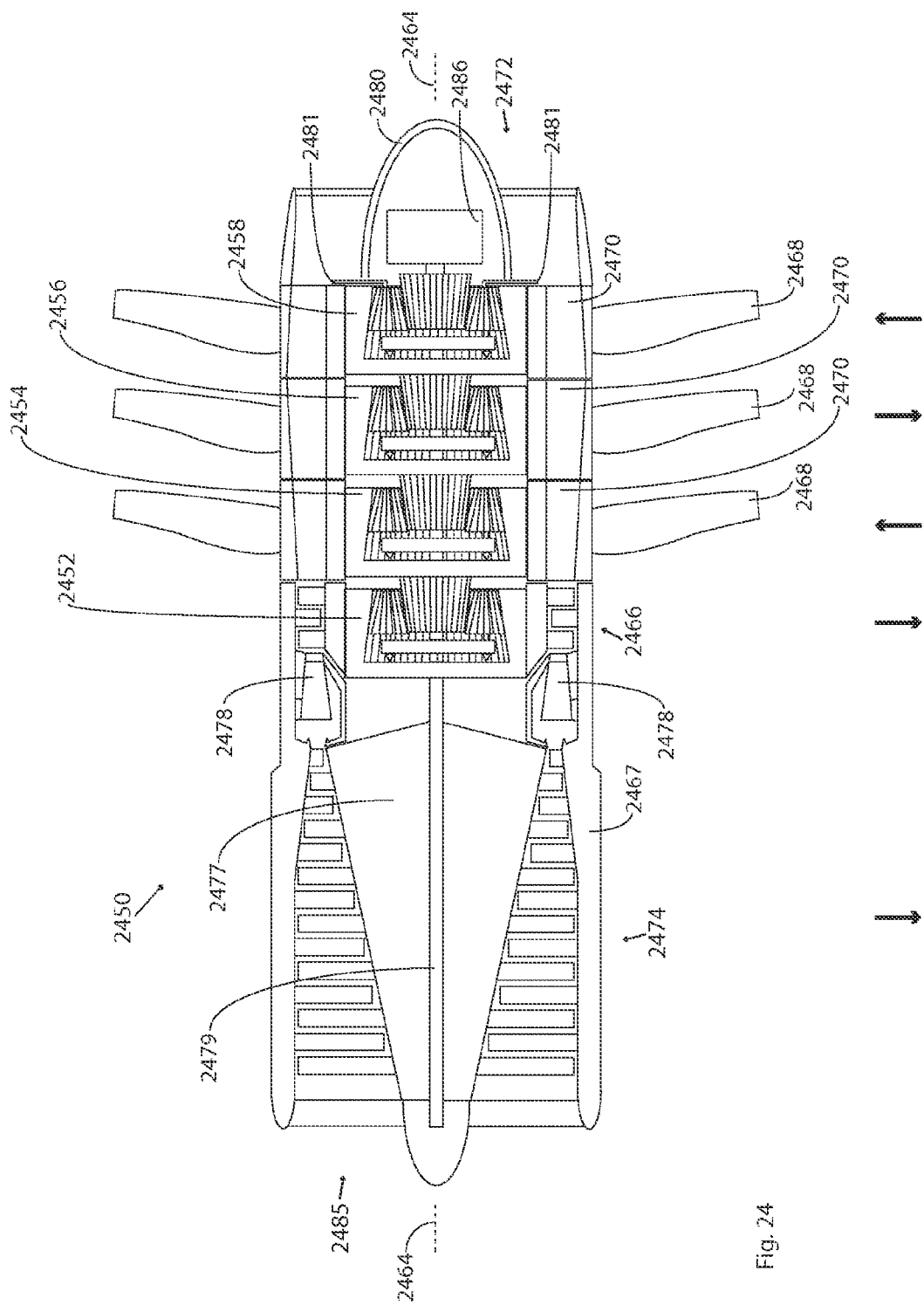
FIG. 24 schematically illustrates a portion of a propfan engine from a cross-sectional side view according to one embodiment of the invention.

FIG. 24 schematically illustrates a portion of a propfan engine from a cross-sectional side view according to one embodiment of the invention. As shown, propfan engine 2450 includes a rotary mechanism that includes rotary units 2452, 2454, 2456, and 2458, respectively, which are configured similar to rotary units 1400, as described herein. Neighboring pairs of rotational components of rotary units in the rotary mechanism are configured to counter-rotate relative to one another around rotational axis 2464 (see, e.g., the directional arrows included in FIG. 24). Each rotary unit in this exemplary embodiment includes one or more implements or portions thereof (e.g., radially inner rotor section of rotary unit 2452, and propeller components 2468 and blade components 2470 of rotary units 2454, 2456, and 2458) that are configured to rotate with the rotational components of the rotary units. Rotary unit 2452 includes radially inner rotor section that includes a plurality of rows of blades and forms a portion of high-pressure turbine 2466. Rotary units 2454, 2456, and 2458 each include a plurality of propeller components 2468 that extend from a segment of nacelle 2467 and rows of blade components 2470 disposed between high-pressure turbine 2466 and exhaust nozzle 2472 within the segments of nacelle 2467. Together blade components 2470 form a low-pressure turbine. In the illustrated embodiment, rotary units with propeller components 2468 are positioned toward an aft end of propfan engine 2450. In other embodiments, rotary units with propeller components 2468 are positioned elsewhere, such as proximal to a forward end of a propfan engine. Propfan engine 2450 also includes air intake 2485 and compressor 2474. In the exemplary embodiment shown, compressor 2474 includes radially inner rotor section 2477 that includes a plurality of rows of blades. Rotor section 2477 is coupled via shaft component 2479 to the rotational component of rotary unit 2452 and rotates within and relative to nacelle 2467, which includes a plurality of rows of blades and forms an outer rotor section of compressor 2474. The rows of blades of the inner and outer rotor sections of compressor 2474 are oriented relative to one another in an axially inter-digitated configuration.

Propfan engine 2450 also includes combustors 2478 disposed between compressor 2474 and high-pressure turbine 2466. Combustors 2478 are coupled to nacelle 2467. High-pressure turbine 2466 includes a plurality of rows of blades that are alternatingly coupled in an axially inter-digitated configuration to rotary unit 2452 and nacelle 2467. The blades of high-pressure turbine 2466 that are coupled to rotary unit 2452 (structured as an inner rotor section) rotate in the same rotational direction as the rotational component of rotary unit 2452. In operation, combustors 2478 generate combustion gases that are channeled downstream to high-pressure turbine 2466 and the low-pressure turbine, which extracts energy from the gases for powering the rotation of inner rotor section 2477 through the rotary mechanism of propfan engine 2450.

As also shown, the support component of the gear structure of rotary unit 2458 is coupled to exhaust cone 2480 via brackets 2481, e.g., to fixedly position the support components of the gear structures of the rotary mechanism of propfan engine 2450 during operation. Propfan engine 2450 also includes motor/generator 2486 operably connected to rotary unit 2458. Motor/generator 2486 is configured to selectively operate as a motor (e.g., to provide mechanical power to the rotary mechanism of propfan engine 2450 during engine start-up, etc.) and as a generator (e.g., to provide electrical power to accessory electrical aircraft components, etc.).

FIG. 25 schematically illustrates a portion of an engine from a cross-sectional side view according to one embodiment of the invention. As shown, engine 2550 includes a rotary mechanism that includes rotary units 2552, which are configured similar to rotary units 1400, as described herein. Neighboring pairs of rotational components of rotary units in the rotary mechanism are configured to counter-rotate relative to one another around rotational axis 2564 (see, e.g., the directional arrows included in FIG. 25). Each rotary unit 2552 is structured as a rotational disk with a plurality of implements shown as propellers 2554) extending from a surface of the rotational component of rotary unit 2552 to and coupled with outer ring 2556 of rotary unit 2552. Rotary units 2552 are configured to rotate within nacelle 2558. Engine 2550 also includes air intake 2560 and nozzle 2562. Engine 2550 also includes motor 2568 (shown as a dual shaft motor in this exemplary embodiment) operably connected to the rotary mechanism and which effects the rotation of rotary units 2552 within nacelle 2558. In some embodiments, multiple single shaft motors are used instead of a dual shaft motor. As also shown, the support components of the gear structures of rotary units 2552 are coupled to nacelle 2558 or exhaust cone 2570 via brackets 2572 and 2574, respectively, e.g., to fixedly position the support components of the gear structures of the rotary mechanism of engine 2550 during operation. In operation, air flows into engine 2550 through air intake 2560 and is accelerated out of nozzle 2562 by rotating propellers 2554 of rotary units 2552.

Figure 28:
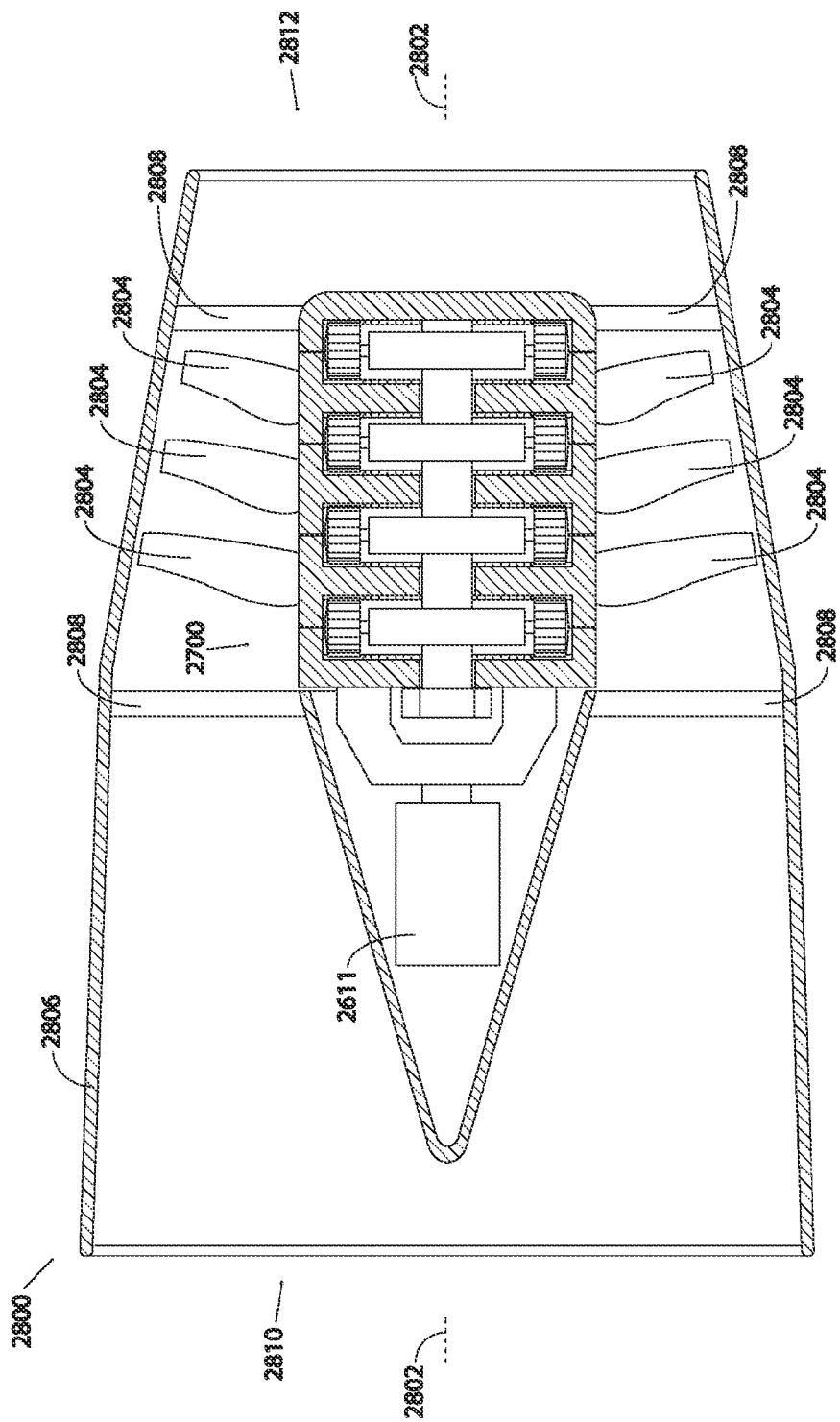
FIG. 28 schematically illustrates a portion of an engine from a cross-sectional side view according to one embodiment of the invention.

FIG. 28 schematically illustrates a portion of an engine from a cross-sectional side view according to one embodiment of the invention. As shown, engine 2800 includes rotary mechanism 2700, as described herein. Neighboring pairs of rotational components 2602 in rotary mechanism 2700 are configured to counter-rotate relative to one another around rotational axis 2802. Each rotational component 2602 is structured as a rotational disk with a plurality of implements (shown as propellers 2804) extending from a surface of rotational components 2602. Rotary mechanism 2700 is positioned relative to nacelle 2806 via spaced mounting brackets 2808, which permit air flow through engine 2800. Rotational components 2602 are configured to rotate within nacelle 2806. Engine 2800 also includes air intake 2810 and nozzle 2812. Motor 2611 effects the rotation of rotational components 2602 and propellers 2804 within nacelle 2806. In operation, air flows into engine 2800 through air intake 2810 and is accelerated out of nozzle 2812 by rotating propellers 2804.

FIG. 29A schematically illustrates a portion of an engine from a cross-sectional side view according to one embodiment of the invention. As shown, engine 2900 includes a rotary mechanism that includes rotary units 2552, which are configured similar to rotary units 1400, as described herein. Neighboring pairs of rotational components of rotary units in the rotary mechanism are configured to counter-rotate relative to one another around rotational axis 2902. Each rotary unit 2552 is structured as a rotational disk with a plurality of implements (shown as propellers 2554) extending from a surface of the rotational component of rotary unit 2552 to and coupled with outer ring 2556 of rotary unit 2552. Rotary units 2552 are configured to rotate within nacelle 2904. Engine 2900 also includes air intake 2906 and nozzle 2908. Engine 2900 also includes motor 2910 operably connected to the rotary mechanism and which effects the rotation of rotary units 2552 within nacelle 2904. As also shown, the support components of the gear structures of rotary units 2552 are coupled to exhaust cone 2912 via brackets 2914, e.g., to fixedly position the support components of the gear structures of the rotary mechanism of engine 2900 during operation. In operation, air flows into engine 2900 through air intake 2906 and is accelerated out of nozzle 2908 by rotating propellers 2554 of rotary units 2552. Typically, one or more components (e.g., rotary units, rotary mechanisms, etc.) of the engines, devices, and other applications described herein are configured to be substantially watertight, e.g., for use in marine environments, inclement weather environments, etc. FIG. 29B schematically shows engine 2900 of FIG. 29A with a cover housing (nacelle 2904) from a side view.

FIGS. 30A-C schematically illustrate a portion of an engine from various views according to one embodiment of the invention. As shown, engine 3050 is configured similar to engine 2900, as described herein, except instead of motor 2910, engine 3050 includes motor 3052. Motor 3052 is operably connected to gear component 3054, which is configured to mesh with a corresponding gear component 3056. Gear component 3056 is disposed around outer ring 2556 of one rotary unit 2552 in this exemplary embodiment. Motor 3052 effects the rotation of rotary units 2552 within nacelle 2904 via meshed gear components 3054 and 3056.

FIG. 31A schematically illustrates kayak 3150 that includes engine 3151 from a side view according to one embodiment of the invention. In some embodiments, kayak 3150 includes foot controls and/or hand controls (e.g., embedded in the body of kayak 3150 or in a paddle). FIG. 31B schematically illustrates submersible 3152 that includes engines 151 from a side view according to one embodiment of the invention. FIG. 31C schematically illustrates hand-held marine propulsion device 3154 that includes engines 3151 from a side view according to one embodiment of the invention. Hand-held marine propulsion device 3154 includes handles 3153 (e.g., to control engine speed, direction, etc.) and is optionally used for water surface and/or sub-surface propulsion. Batteries, engine controllers, and/or the like are typically housed within body 3155. FIG. 31D schematically illustrates boogie board 3156 that includes engines 3151 from a side view according to one embodiment of the invention. As shown, boogie board 3156 also includes hand controllers 3157 disposed in body 3159. Hand controllers 3157 are typically used to regulate the speed of engines 3151 and/or the direction of boogie board 3156 during operation. FIG. 31E schematically illustrates paddle board 3158 that includes engine 3151 from a side view according to one embodiment of the invention. FIG. 31F schematically illustrates personal watercraft 3160 that includes engine 3151 from a side view according to one embodiment of the invention. Many of the engines or propulsion devices (e.g., engine 2550, engine 2900, engine 3050, propulsion devices 3302, etc.) of the invention are optionally adapted for use as engines 3101 with these exemplary marine applications. Other exemplary marine vehicles that are optionally adapted for use with the propulsion devices of the invention include, e.g., boats, ships, submarines, surf boards, wind surfing boards, water skis, wake boards, and the like includes.

Device components (e.g., rotary units, rotary mechanisms, drive mechanism components, gear components, shafts, rotational components, device housings, doors, support structures, etc.) are optionally formed by various fabrication techniques or combinations of such techniques including, e.g., cast molding, stamping, machining, embossing, extrusion, engraving, injection molding, etching (e.g., electrochemical etching, etc.), or other techniques. These and other suitable fabrication techniques are generally known in the art and described in, e.g., Molinari et al. (Eds.), Metal Cutting and High Speed Machining, Kluwer Academic Publishers (2002), Altintas, Manufacturing Automation: Metal Cutting Mechanics, Machine Tool Vibrations, and CNC Design, Cambridge University Press (2000), Stephenson et al., Metal Cutting Theory and Practice, Marcel Dekker (1997), Fundamentals of Injection Molding, W. J. T. Associates (2000), Whelan, Injection Molding of Thermoplastics Materials, Vol. 2, Chapman & Hall (1991), Rosato, Injection Molding Handbook, 3.sup.rd Ed., Kluwer Academic Publishers (2000), Fisher, Extrusion of Plastics, Halsted Press (1976), and Chung, Extrusion of Polymers: Theory and Practice, Hanser-Gardner Publications (2000), which are each incorporated by reference. Exemplary materials optionally used to fabricate device components include, e.g., metal, glass, wood, polymethylmethacrylate, polyethylene, polydimethylsiloxane, polyetheretherketone, polytetrafluoroethylene, polystyrene, polyvinylchloride, polypropylene, polysulfone, polymethylpentene, and polycarbonate, among many others. In certain embodiments, following fabrication, device components are optionally further processed, e.g., by painting, coating surfaces with a hydrophilic coating, a hydrophobic coating, or the like.

Exemplary rotary units, rotational mechanisms, related applications, and other aspects, which are optionally adapted, e.g., for use with the rotary units, rotational mechanisms, engines, aircraft, vehicles, and devices described herein are also described in, e.g., U.S. patent application Ser. No. 12/577,326, entitled "ROTARY UNITS, MECHANISMS, AND RELATED DEVICES", filed on Oct. 12, 2009 (now U.S. Pat. No. 8,152,679, issued Apr. 10, 2012), U.S. Provisional Patent Application No. 61/104,748, entitled "ROTARY UNITS, MECHANISMS, AND RELATED DEVICES", filed on Oct. 12, 2008, International Application No. PCT/US2009/060386, entitled "ROTARY UNITS, MECHANISMS, AND RELATED DEVICES", filed on Oct. 12, 2009, U.S. Provisional Patent Application No. 61/365,290, entitled "ROTARY UNITS, MECHANISMS, AND RELATED DEVICES", filed on Jul. 16, 2010, U.S. Provisional Patent Application No. 61/640,530, entitled "ELECTRICAL APPARATUS AND RELATED METHODS", filed on Apr. 30, 2012, U.S. patent application Ser. No. 13/184,332, entitled "ROTARY UNITS, MECHANISMS, AND RELATED DEVICES", filed on Jul. 15, 2011, U.S. patent application Ser. No. 13/218,145, entitled "ROTARY UNITS, MECHANISMS, AND RELATED DEVICES", filed on Aug. 25, 2011, U.S. patent application Ser. No. 13/219,683, entitled "ROTARY UNITS, MECHANISMS, AND RELATED DEVICES", filed on Aug. 28, 2011, U.S. patent application Ser. No. 13/221,890, entitled "ROTARY UNITS, MECHANISMS, AND RELATED DEVICES", filed on Aug. 30, 2011, and U.S. patent application Ser. No. 13/423,413, entitled "ROTARY UNITS, MECHANISMS, AND RELATED DEVICES", filed on Mar. 19, 2012, U.S. Pat. No. 8,016,561, entitled "GAS TURBINE ENGINE FAN ASSEMBLY AND METHOD FOR ASSEMBLING TO SAME", issued Sep. 13, 2011, U.S. Pat. No. 7,418,821, entitled "AIRCRAFT GAS TURBINE ENGINES", issued Sep. 2, 2008, U.S. Pat. No. 8,127,732, entitled "LASER IGNITION SYSTEM AND METHOD FOR INTERNAL COMBUSTION ENGINE", issued Mar. 6, 2012, U.S. Pat. No. 7,997,085, entitled "GAS TURBINE ENGINE ASSEMBLY AND METHOD OF ASSEMBLING SAME", issued Aug. 16, 2011, U.S. Pat. No. 8,074,592, entitled "SUBMARINE WITH A PROPULSION DRIVE WITH AN ELECTRIC MOTOR RING", issued Dec. 13, 2011, U.S. Pat. No. 4,274,357, entitled "POWER OPERATED SURFBOARD", issued Jun. 23, 1981, U.S. Pat. No. 7,874,883, entitled "SYSTEM FOR STEERING AND MANEUVERING A WATERCRAFT PROPELLED BY A WATER JET", issued Jan. 25, 2011, and U.S. Pat. No. 8,172,629, entitled "PERSONAL WATERCRAFT", issued May 8, 2012, which are each incorporated herein by reference in their entirety for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An engine, comprising:
   at least one rotary mechanism that comprises at least first and second rotational components and at least a first counter-rotational mechanism that operably engages at least the first and second rotational components, wherein the first and second rotational components are configured to rotate substantially non-concentrically relative to one another around a first rotational axis, and wherein one or more of the rotational components comprise at least one compressor, at least one turbine, and/or at least a portion thereof;
   at least one drive mechanism component or portion thereof that operably engages one or more of the rotational components and/or the first counter-rotational mechanism such that when the first rotational component rotates in a first direction, the second rotational component rotates in a second direction; and,
   at least one combustor in communication with the compressor and/or the turbine.

2. The engine of claim 1, comprising at least one nacelle component that contains at least a portion of the rotary mechanism, the drive mechanism component or portion thereof, and/or the combustor.

3. The engine of claim 1, wherein one or more of the rotational components comprise the combustor or a portion thereof.

4. The engine of claim 1, comprising a propeller, an impeller, a fan assembly, a fan, a blade, a booster, a nozzle, a duct, a generator, a motor, a gear component, and/or a component thereof.

5. The engine of claim 1, wherein one or more of the rotational components comprise a propeller, an impeller, a fan assembly, a fan, a blade, a rotor, a booster, a nozzle, a duct, a generator, a motor, a gear component, and/or a component thereof.

6. A ground vehicle, a marine vehicle, an aircraft, or a device comprising the engine of claim 1.

7. The engine of claim 1, wherein:
   the first rotational component comprises at least first and second sun gear components;
   the second rotational component comprises at least first and second ring gear components; and,
   the first counter-rotational mechanism comprises at least a first planetary gear component that is configured to operably engage the second sun gear component of the first rotational component and the first ring gear component of the second rotational component such that when the first rotational component rotates in the first direction, the second rotational component rotates in the second direction.

8. The engine of claim 1, comprising at least two rotary units that each comprises:
   at least one rotational component that comprises at least one ring gear component; and
   at least one second gear component configured to operably engage the ring gear component.

9. The engine of claim 1, wherein:
   the first and second rotational components each comprise at least one ring gear component; and,
   the first counter-rotational mechanism comprises at least a first gear component that operably engages the ring gear component of at least the first rotational component, at least a second gear component that operably engages the ring gear component of at least the second rotational component, and at least a third gear component that operably engages at least the second gear component such that when the first gear component rotates in the first direction, the first rotational component rotates in the first direction and the second gear component and the second rotational component rotate in the second direction.

10. The engine of claim 1, wherein:
   the first and second rotational components each comprise at least two ring gear components; and,
   the first counter-rotational mechanism comprises at least a first planetary gear component that is configured to operably engage at least one of the ring gear components of the first rotational component and at least one of the ring gear components of the second rotational component such that when the first rotational component rotates in the first direction, the second rotational component rotates in the second direction.

11. The engine of claim 1, comprising at least two rotary units that each comprises:
   at least one rotational component that comprises at least one sun gear component and at least one ring gear component, and
   at least one gear structure that comprises at least one support component and at least one planetary gear component rotatably coupled to the support component, and wherein the planetary gear component is configured to operably engage the ring gear component, wherein the sun gear component of at least a first rotary unit operably engages the planetary gear component of at least a second rotary unit such that when the rotational component of the first rotary unit rotates in the first direction, the rotational component of the second rotary unit rotates in the second direction.

12. The engine of claim 11, wherein the gear structure of the first rotary unit is operably connected to the gear structure of the second rotary unit such that the support components are substantially fixedly positioned relative to one another at least when the rotational component of the first rotary unit rotates in the first direction, the rotational component of the second rotary unit rotates in the second direction.

13. A rotary unit, comprising at least a first rotational component that comprises at least one surface that comprises at least a first implement selected from the group consisting of: a first propeller, a first impeller, a first fan assembly, a first fan, a first blade, a first compressor, a first rotor, a first booster, a first combustor, a first turbine, a first nozzle, a first duct, a first generator, a first motor, a first gear component, and a first component thereof, and at least a second gear component that is configured to operably engage one or more other gear components of at least second and third rotational components when the first rotational component is disposed proximal to the second and third rotational components such that when the first rotational component rotates in a first direction, the second and third rotational components rotate in a second direction.

14. The rotary unit of claim 13, wherein the surface of the first rotational component that comprises the first implement is configured to rotate substantially non-concentrically relative to the second and/or third rotational component.

15. A rotary mechanism comprising the rotary unit of claim 13.

16. An engine comprising the rotary unit of claim 13.

17. A ground vehicle, a marine vehicle, an aircraft, or a device comprising the rotary mechanism of claim 13.

18. A method of rotating rotational components, the method comprising:
(a) providing at least one rotary mechanism that comprises:
at least first, second, and third rotational components, wherein at least one of the rotational components comprises at least one implement selected from the group consisting of: a propeller, an impeller, a fan assembly, a fan, a blade, a compressor, a booster, a combustor, a rotor, a turbine, a nozzle, a duct, a generator, a motor, a gear component, and a component thereof; and
at least first and second counter-rotational mechanisms, wherein the first counter-rotational mechanism operably engages at least the first and second rotational components, and wherein the second counter-rotational mechanism operably engages at least the second and third rotational components; and,
(b) rotating the rotational components and the counter-rotational mechanisms such that the first and third rotational components rotate in a first direction and the second rotational component rotates in a second direction, thereby rotating rotational components.

19. The method of claim 18, wherein the rotary mechanism comprises at least one drive mechanism component or a portion thereof that operably engages one or more of the rotational components and/or one or more of the counter-rotational mechanisms, and wherein (b) comprises using the drive mechanism component or portion thereof to effect rotation of the rotational components and the counter-rotational mechanisms.

20. The method of claim 18, wherein one or more of the rotational components comprises at least one gear component that operably engages at least one gear component of at least one propulsion component and wherein (b) comprises rotating the propulsion component.

* * * * *